US011992287B2

(12) United States Patent
Duque et al.

(10) Patent No.: US 11,992,287 B2
(45) Date of Patent: May 28, 2024

(54) ARTICULABLE MEDICAL DEVICES HAVING FLEXIBLE WIRE ROUTING

(71) Applicant: Intuitive Surgical Operations, Inc., Sunnyvale, CA (US)

(72) Inventors: Grant Duque, San Jose, CA (US); Lawrence Kerver, San Jose, CA (US); David I. Moreira Ridsdale, Saratoga, CA (US); Harsukhdeep Singh Ratia, Foster City, CA (US); Joseph P. Orban, III, Norwalk, CT (US); Zhou Ye, Santa Clara, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 837 days.

(21) Appl. No.: 17/045,679

(22) PCT Filed: Apr. 9, 2019

(86) PCT No.: PCT/US2019/026581
§ 371 (c)(1),
(2) Date: Oct. 6, 2020

(87) PCT Pub. No.: WO2019/199827
PCT Pub. Date: Oct. 17, 2019

(65) Prior Publication Data
US 2021/0022819 A1 Jan. 28, 2021

Related U.S. Application Data

(60) Provisional application No. 62/655,496, filed on Apr. 10, 2018.

(51) Int. Cl.
*A61B 18/12* (2006.01)
*A61B 18/14* (2006.01)
(Continued)

(52) U.S. Cl.
CPC .......... *A61B 34/71* (2016.02); *A61B 18/1445* (2013.01); *A61B 34/35* (2016.02);
(Continued)

(58) Field of Classification Search
CPC combination set(s) only.
See application file for complete search history.

(56) References Cited

U.S. PATENT DOCUMENTS

| 5,052,402 A | 10/1991 | Bencini et al. |
| 5,325,845 A | 7/1994 | Adair |

(Continued)

FOREIGN PATENT DOCUMENTS

| CN | 101677817 A | 3/2010 |
| CN | 105012023 A | 11/2015 |

(Continued)

OTHER PUBLICATIONS

International Search Report and Written Opinion for Application No. PCT/US2019/026581, dated Jul. 18, 2019, 9 pages.

(Continued)

*Primary Examiner* — Daniel W Fowler

(57) ABSTRACT

An articulable medical device includes a link, a transfer member, a tool member, and a non-drive wire. The tool member has a base portion movably coupled to the transfer member, and a contact portion configured to engage a target tissue. The transfer member is rotatably coupled to the link to rotate with the tool member relative to the link from a first orientation to a second orientation. The non-drive wire has a first end portion coupled to an energy source, a second end portion coupled to the tool member contact portion, and a central portion between the first and second end portions that includes a transition portion disposed within a cavity defined within the base portion of the tool member, a distal portion of the link, or the transfer member, which has a compact first (Continued)

configuration in the first orientation and an expanded second configuration in the second orientation.

17 Claims, 29 Drawing Sheets

(51) Int. Cl.
  *A61B 34/00* (2016.01)
  *A61B 34/35* (2016.01)
  *A61B 17/00* (2006.01)
  *A61B 17/29* (2006.01)
  *A61B 17/32* (2006.01)
  *A61B 18/00* (2006.01)
  *A61B 34/30* (2016.01)

(52) U.S. Cl.
  CPC .............. *A61B 2017/00323* (2013.01); *A61B 2017/2903* (2013.01); *A61B 2017/2908* (2013.01); *A61B 17/320016* (2013.01); *A61B 2018/00595* (2013.01); *A61B 2034/301* (2016.02); *A61B 2034/715* (2016.02)

(56) References Cited

U.S. PATENT DOCUMENTS

| | | |
|---|---|---|
| 5,395,369 A | 3/1995 | Mcbrayer et al. |
| 5,396,900 A | 3/1995 | Slater et al. |
| 5,482,054 A | 1/1996 | Slater et al. |
| 5,496,317 A | 3/1996 | Goble et al. |
| 5,496,347 A | 3/1996 | Hashiguchi et al. |
| 5,688,269 A | 11/1997 | Newton et al. |
| 5,792,135 A | 8/1998 | Madhani et al. |
| 5,792,165 A | 8/1998 | Klieman et al. |
| 5,807,377 A | 9/1998 | Madhani et al. |
| 5,810,876 A | 9/1998 | Kelleher |
| 5,899,914 A | 5/1999 | Zirps et al. |
| 5,916,146 A | 6/1999 | Allotta et al. |
| 6,206,903 B1 | 3/2001 | Ramans |
| 6,273,860 B1 | 8/2001 | Kostylev et al. |
| 6,331,181 B1 | 12/2001 | Tierney et al. |
| 6,371,956 B1 | 4/2002 | Wilson et al. |
| 6,394,998 B1 | 5/2002 | Wallace et al. |
| 6,464,701 B1 | 10/2002 | Hooven et al. |
| 6,491,691 B1 | 12/2002 | Morley et al. |
| 6,491,701 B2 | 12/2002 | Tierney et al. |
| 6,554,844 B2 | 4/2003 | Lee et al. |
| 6,623,482 B2 | 9/2003 | Pendekanti et al. |
| 6,685,698 B2 | 2/2004 | Morley et al. |
| 6,767,349 B2 | 7/2004 | Ouchi |
| 6,817,974 B2 | 11/2004 | Cooper et al. |
| 6,840,938 B1 | 1/2005 | Morley et al. |
| 6,964,662 B2 | 11/2005 | Kidooka |
| 6,969,385 B2 | 11/2005 | Moreyra |
| 6,994,708 B2 | 2/2006 | Manzo |
| 7,354,439 B2 | 4/2008 | Kidooka |
| 7,648,519 B2 | 1/2010 | Lee et al. |
| 7,824,401 B2 | 11/2010 | Manzo et al. |
| 7,935,130 B2 | 5/2011 | Williams |
| 8,257,371 B2 | 9/2012 | Hamilton et al. |
| 8,479,969 B2 | 7/2013 | Shelton, IV |
| 8,758,392 B2 | 6/2014 | Crainich |
| 8,771,270 B2 | 7/2014 | Burbank |
| 8,800,838 B2 | 8/2014 | Shelton, IV |
| 9,028,494 B2 | 5/2015 | Shelton, IV et al. |
| 9,055,961 B2 | 6/2015 | Manzo et al. |
| 9,078,684 B2 | 7/2015 | Williams |
| 9,204,923 B2 | 12/2015 | Manzo et al. |
| 9,232,979 B2 | 1/2016 | Parihar et al. |
| 9,259,275 B2 | 2/2016 | Burbank |
| 9,339,341 B2 | 5/2016 | Cooper |
| 9,358,031 B2 | 6/2016 | Manzo |
| 9,456,839 B2 | 10/2016 | Cooper |
| 9,782,214 B2 | 10/2017 | Houser et al. |
| 9,918,731 B2 | 3/2018 | Cooper et al. |
| 10,130,366 B2 | 11/2018 | Shelton, IV et al. |
| 10,201,365 B2 | 2/2019 | Boudreaux et al. |
| 10,667,873 B2 | 6/2020 | Wallace |
| 2002/0072742 A1* | 6/2002 | Schaefer .......... A61B 18/1477 606/41 |
| 2004/0019352 A1 | 1/2004 | Kidooka |
| 2004/0116924 A1* | 6/2004 | Dycus ............... A61B 18/1445 606/171 |
| 2004/0162557 A1 | 8/2004 | Tetzlaff et al. |
| 2005/0187547 A1 | 8/2005 | Sugi |
| 2005/0240178 A1 | 10/2005 | Morley et al. |
| 2006/0074415 A1* | 4/2006 | Scott ................... A61B 34/71 606/45 |
| 2006/0190034 A1 | 8/2006 | Nishizawa et al. |
| 2007/0208375 A1 | 9/2007 | Nishizawa et al. |
| 2007/0246508 A1 | 10/2007 | Green |
| 2007/0282256 A1* | 12/2007 | Hu ..................... A61M 29/02 604/96.01 |
| 2008/0046122 A1 | 2/2008 | Manzo et al. |
| 2008/0065102 A1 | 3/2008 | Cooper |
| 2008/0065105 A1 | 3/2008 | Larkin et al. |
| 2008/0132893 A1 | 6/2008 | D'Amelio et al. |
| 2008/0167651 A1 | 7/2008 | Tetzlaff et al. |
| 2008/0196533 A1 | 8/2008 | Bergamasco et al. |
| 2009/0088774 A1 | 4/2009 | Swarup et al. |
| 2009/0131975 A1 | 5/2009 | Ahlberg et al. |
| 2009/0198272 A1 | 8/2009 | Kerver et al. |
| 2009/0209960 A1 | 8/2009 | Chojin |
| 2009/0326530 A1 | 12/2009 | Orban, III et al. |
| 2010/0168721 A1 | 7/2010 | Rogers et al. |
| 2010/0198218 A1 | 8/2010 | Manzo |
| 2010/0198231 A1 | 8/2010 | Scott |
| 2010/0198253 A1 | 8/2010 | Jinno et al. |
| 2011/0071543 A1 | 3/2011 | Prisco et al. |
| 2011/0106073 A1* | 5/2011 | Mueller ............ A61B 18/1445 606/41 |
| 2011/0106145 A1* | 5/2011 | Jeong ................. A61B 34/77 606/205 |
| 2011/0295269 A1 | 12/2011 | Swensgard et al. |
| 2011/0295270 A1 | 12/2011 | Giordano et al. |
| 2011/0301599 A1 | 12/2011 | Roy et al. |
| 2012/0010611 A1 | 1/2012 | Krom et al. |
| 2012/0010615 A1* | 1/2012 | Cummings ........ A61B 18/1445 606/51 |
| 2012/0116433 A1 | 5/2012 | Houser et al. |
| 2012/0197253 A1 | 8/2012 | Nishimura et al. |
| 2012/0330287 A1 | 12/2012 | Yim |
| 2013/0123783 A1 | 5/2013 | Marczyk et al. |
| 2013/0144395 A1 | 6/2013 | Stefanchik et al. |
| 2013/0239735 A1 | 9/2013 | Solomon et al. |
| 2014/0005662 A1 | 1/2014 | Shelton, IV |
| 2014/0005678 A1 | 1/2014 | Shelton, IV et al. |
| 2014/0005708 A1 | 1/2014 | Shelton, IV |
| 2014/0073856 A1 | 3/2014 | Stein et al. |
| 2014/0100558 A1 | 4/2014 | Schmitz et al. |
| 2014/0187895 A1* | 7/2014 | Mody ................ A61B 18/1492 607/116 |
| 2014/0257333 A1 | 9/2014 | Blumenkranz |
| 2014/0276956 A1 | 9/2014 | Crainich et al. |
| 2015/0157355 A1 | 6/2015 | Price et al. |
| 2015/0257816 A1 | 9/2015 | Ineson |
| 2015/0280384 A1 | 10/2015 | Leimbach et al. |
| 2015/0313676 A1 | 11/2015 | Deodhar |
| 2016/0058443 A1 | 3/2016 | Yates et al. |
| 2016/0143688 A1 | 5/2016 | Orban, III et al. |
| 2016/0296219 A1 | 10/2016 | Srivastava et al. |
| 2016/0302819 A1 | 10/2016 | Stulen et al. |
| 2017/0007242 A1 | 1/2017 | Shelton, IV et al. |
| 2017/0165017 A1 | 6/2017 | Chaplin et al. |
| 2017/0215944 A1 | 8/2017 | Keffeler |
| 2017/0252096 A1 | 9/2017 | Felder et al. |
| 2018/0080533 A1 | 3/2018 | Awtar |
| 2018/0116708 A1 | 5/2018 | Manzo et al. |
| 2018/0206904 A1 | 7/2018 | Felder et al. |
| 2019/0069966 A1 | 3/2019 | Petersen et al. |
| 2019/0090940 A1 | 3/2019 | Manzo et al. |
| 2019/0201018 A1 | 7/2019 | Shelton, IV et al. |

(56) References Cited

U.S. PATENT DOCUMENTS

| | | |
|---|---|---|
| 2019/0223960 A1 | 7/2019 | Chaplin et al. |
| 2019/0290310 A1 | 9/2019 | Klein |
| 2019/0374297 A1 | 12/2019 | Wallace et al. |
| 2019/0380800 A1 | 12/2019 | Jogasaki et al. |
| 2020/0015807 A1 | 1/2020 | Limon et al. |
| 2020/0022765 A1 | 1/2020 | Limon et al. |
| 2020/0054405 A1 | 2/2020 | Schuh et al. |
| 2020/0054408 A1 | 2/2020 | Schuh et al. |
| 2020/0138531 A1 | 5/2020 | Chaplin |
| 2020/0155136 A1 | 5/2020 | Shuh et al. |
| 2020/0155253 A1 | 5/2020 | Shuh et al. |
| 2021/0401487 A1 | 12/2021 | Apostolopoulos et al. |
| 2021/0401513 A1 | 12/2021 | Apostolopoulos et al. |
| 2022/0226060 A1 | 7/2022 | Wang et al. |

FOREIGN PATENT DOCUMENTS

| | | |
|---|---|---|
| CN | 105816239 A | 8/2016 |
| EP | 1151723 A2 | 11/2001 |
| EP | 2548529 A1 | 1/2013 |
| EP | 2783643 A1 | 10/2014 |
| JP | 2010022696 A | 2/2010 |
| JP | 2013017542 A | 1/2013 |
| WO | WO-02080783 A1 | 10/2002 |
| WO | WO-2010088588 A1 | 8/2010 |
| WO | WO-2011060031 A1 | 5/2011 |
| WO | WO-2012006306 A2 | 1/2012 |
| WO | WO-2014025204 A1 | 2/2014 |
| WO | WO-2016025132 A1 | 2/2016 |
| WO | WO-2016045041 A1 | 3/2016 |
| WO | WO-2017064303 A1 | 4/2017 |
| WO | WO-2017136710 A2 | 8/2017 |
| WO | WO-2018069679 A1 | 4/2018 |
| WO | WO-2018123024 A1 | 7/2018 |
| WO | WO-2018179140 A1 | 10/2018 |
| WO | WO-2018222899 A1 | 12/2018 |
| WO | WO-2018234795 A1 | 12/2018 |
| WO | WO-2018234814 A1 | 12/2018 |
| WO | WO-2019199827 A1 | 10/2019 |
| WO | WO-2023129448 A1 | 7/2023 |
| WO | WO-2023177556 A1 | 9/2023 |

OTHER PUBLICATIONS

Non-Final Office Action dated Feb. 5, 2018 for U.S. Appl. No. 14/933,875, filed Nov. 5, 2015, 9 pages (ISRG01580D1/US).

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Office Action for CN Application No. 201980024514.1, dated Jul. 20, 2023, 27 pages.

Extended European Search Report for Application No. EP19784413.7, dated Dec. 8, 2021, 9 pages.

Office Action for CN Application No. 201980024514.1, mailed Feb. 27, 2024, 13 pages.

\* cited by examiner

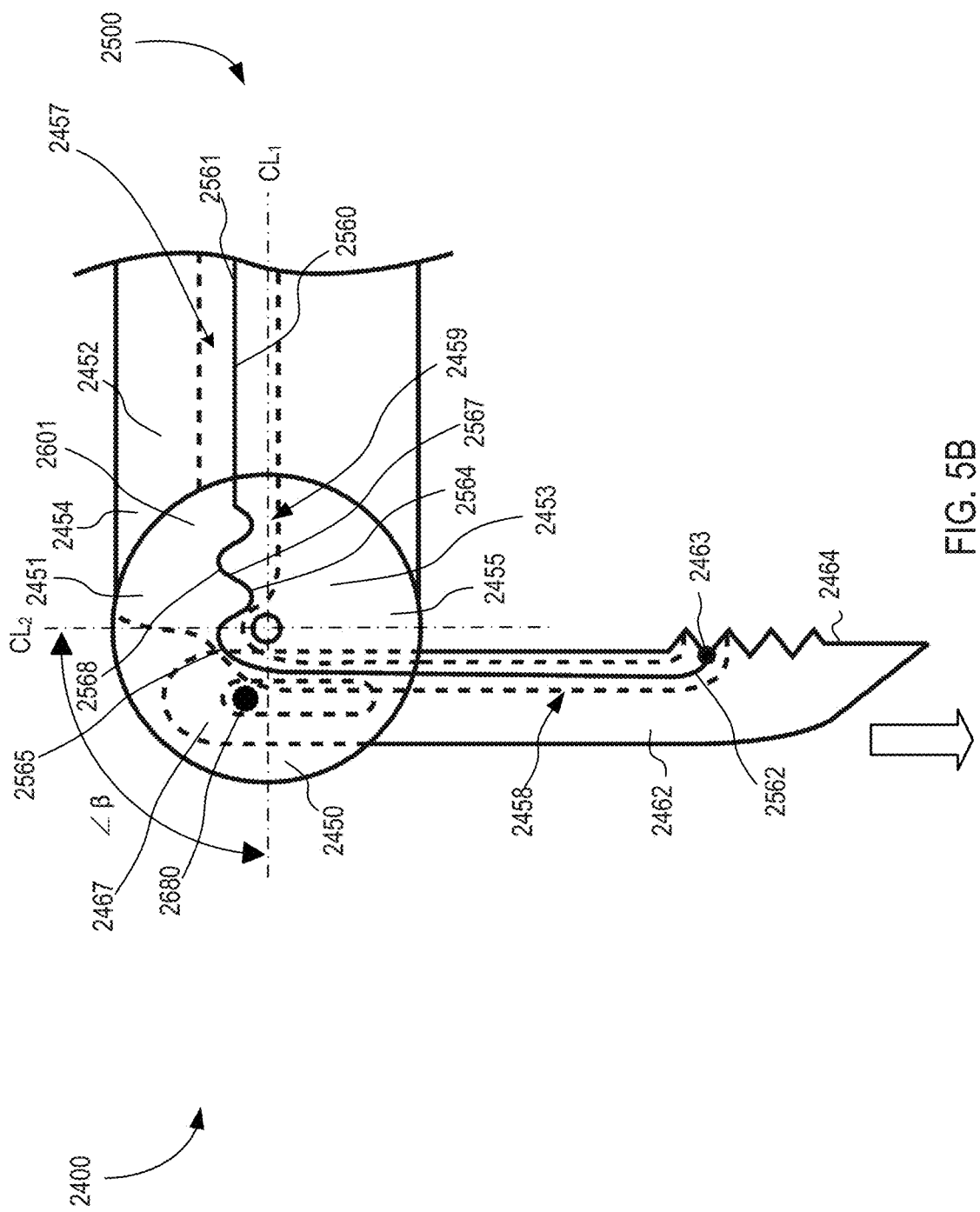

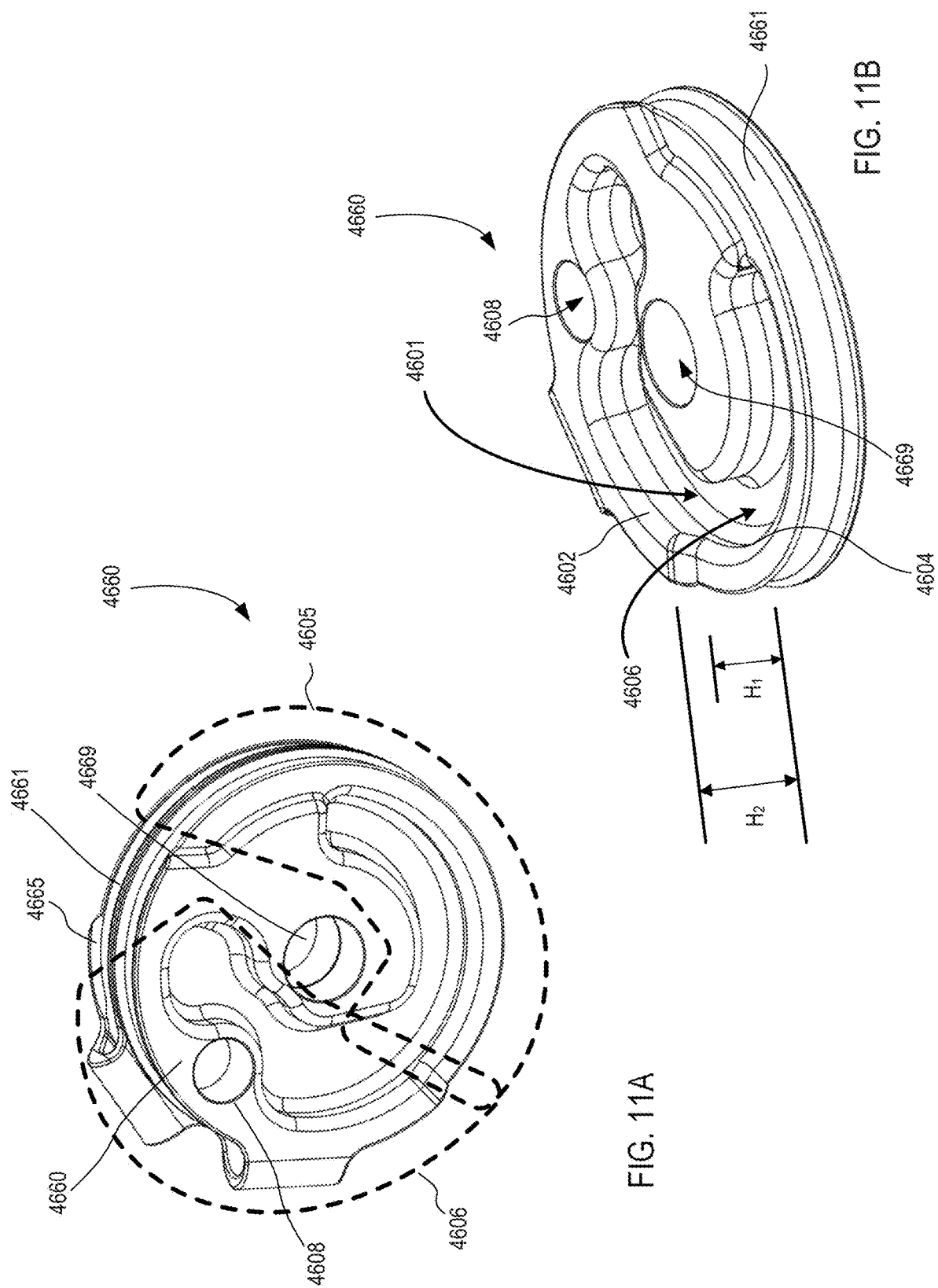

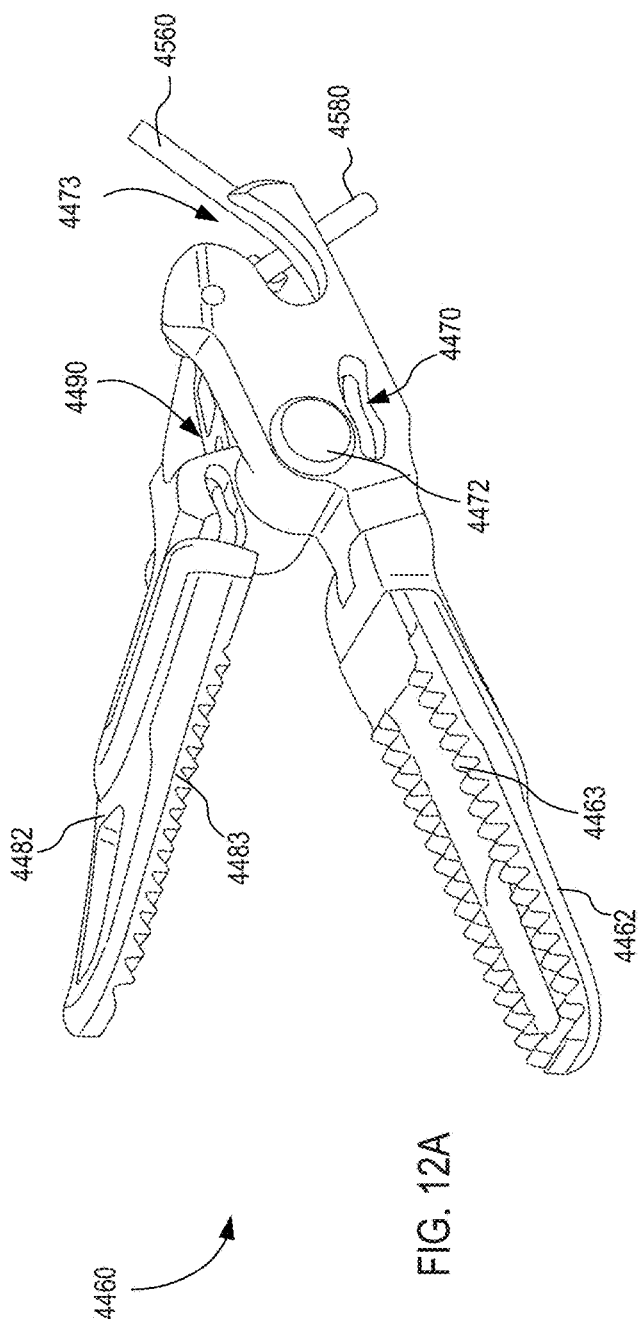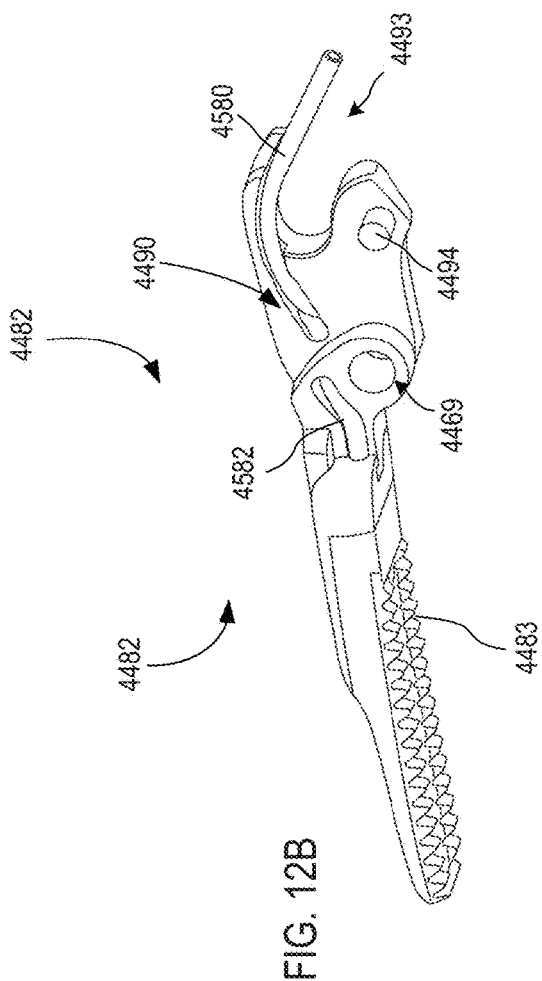
FIG. 12A
FIG. 12B

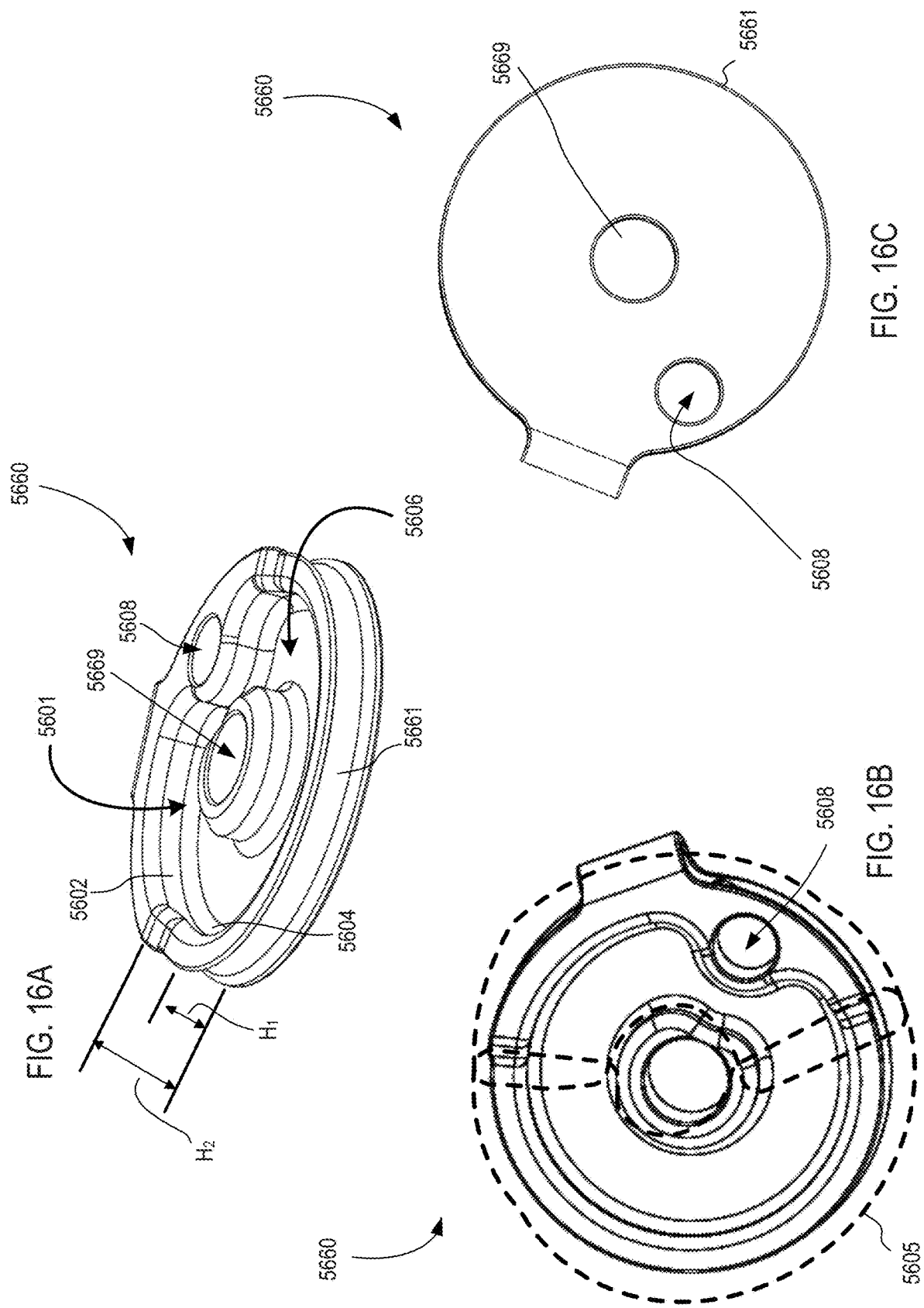

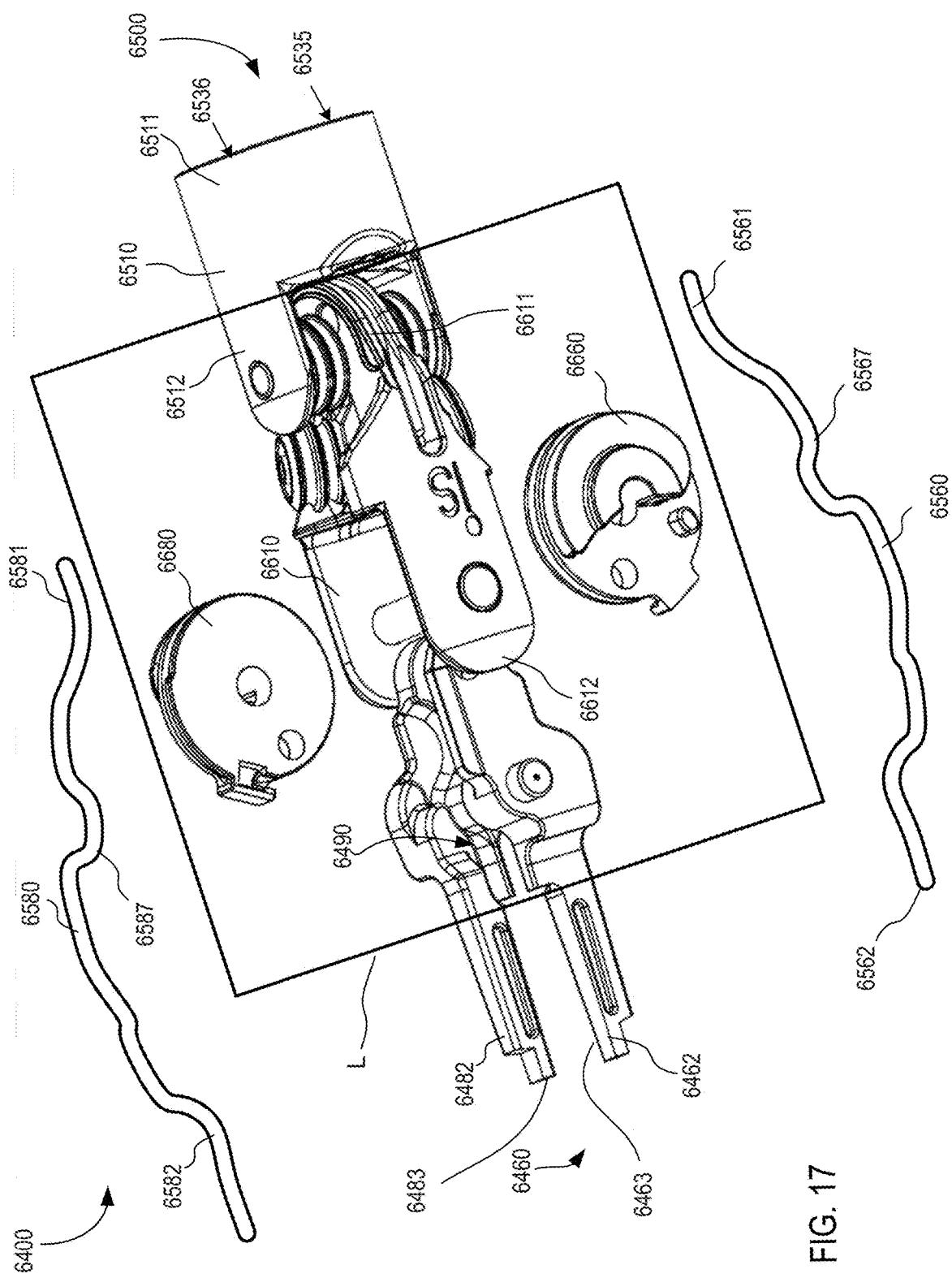

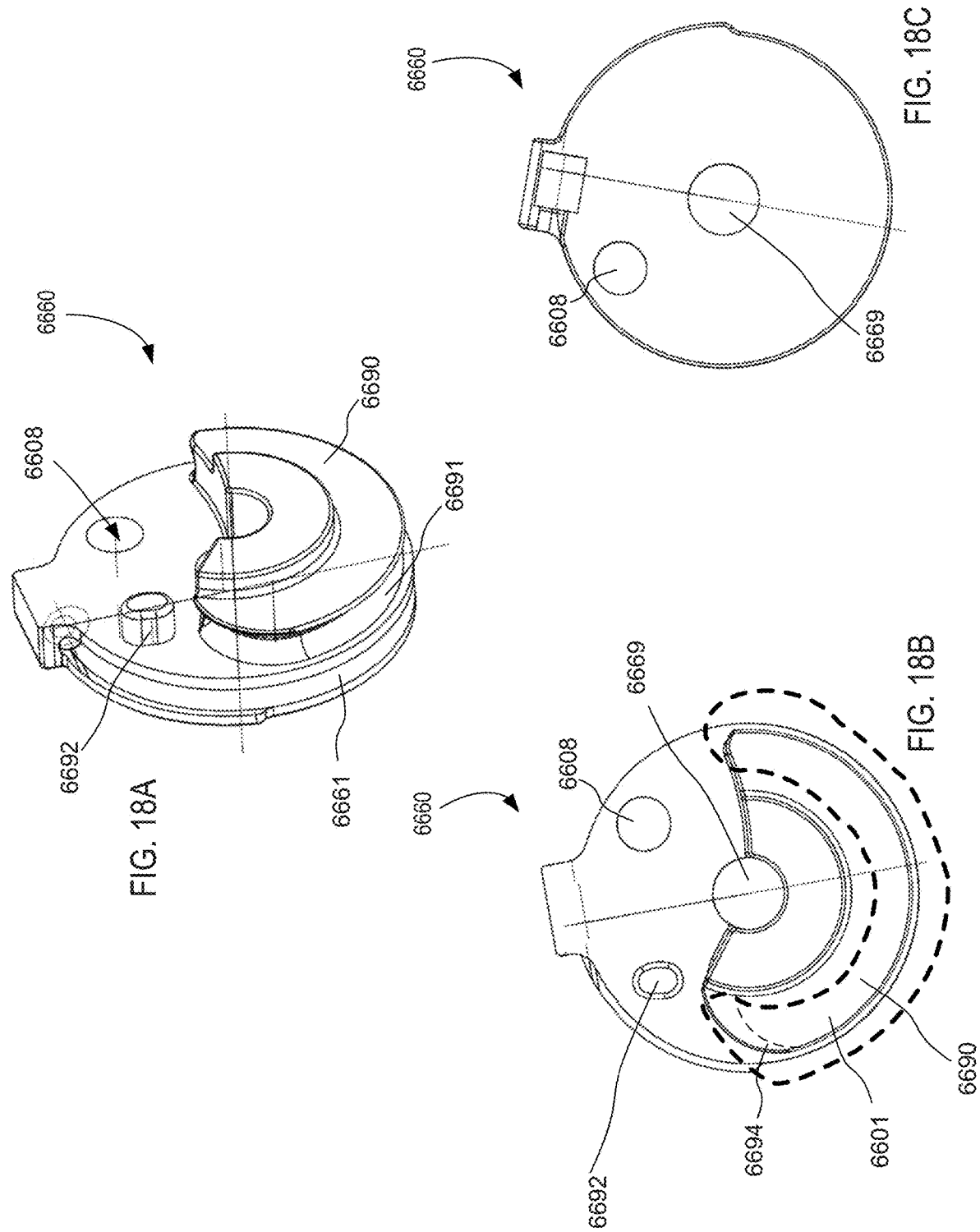

ARTICULABLE MEDICAL DEVICES HAVING FLEXIBLE WIRE ROUTING

CROSS-REFERENCE TO RELATED APPLICATIONS

This application is a U.S. national stage filing under 35 U.S.C. § 371 of International Application No. PCT/US2019/026581 (filed Apr. 9, 2019)(entitled "ARTICULABLE MEDICAL DEVICES HAVING FLEXIBLE WIRE ROUTING"), which claims priority to and the filing date benefit of U.S. Provisional Patent Application Ser. No. 62/655,496 (filed Apr. 10, 2018)(entitled "ARTICULABLE MEDICAL DEVICES HAVING FLEXIBLE WIRE ROUTING"), which is incorporated herein by reference herein in its entirety.

BACKGROUND

The embodiments described herein relate to grasping tools, more specifically to medical devices, and still more specifically to endoscopic tools. More particularly, the embodiments described herein relate to articulable medical devices that include one or more non-drive wires flexibly routed in the articulable device that can be used, for example, in surgical applications.

Known techniques for Minimally Invasive Surgery (MIS) employ instruments to manipulate tissue that can be either manually controlled or controlled via computer-assisted teleoperation. Many known MIS instruments include a therapeutic or diagnostic end effector (e.g., forceps, a cutting tool, or a cauterizing tool) mounted on a wrist mechanism at the distal end of an extension (also referred to herein as the main tube or shaft). During an MIS procedure, the end effector, wrist mechanism, and the distal end of the main tube can be inserted into a small incision or a natural orifice of a patient to position the end effector at a work site within the patient's body. The optional wrist mechanism can be used to change the end effector's orientation with respect to the main tube to perform the desired procedure at the work site. Known wrist mechanisms generally provide the desired degrees of freedom (DOFs) for movement of the end effector. For example, for forceps or other grasping tools, known wrist mechanisms are often able to change the pitch and yaw of the end effector with reference to the main tube. A wrist may optionally provide a roll DOF for the end effector, or the roll DOF may be implemented by rolling the main tube. An end effector may optionally have additional mechanical DOFs, such as grip or knife blade motion. In some instances, wrist and end effector mechanical DOFs may be combined. For example, U.S. Pat. No. 5,792,135 (filed May 16, 1997) discloses a mechanism in which wrist and end effector grip DOFs are combined.

To enable the desired movement of the wrist mechanism and end effector, known instruments include tension members (e.g., cables, cable/hypotube combinations, tension bands) that extend through the main tube of the instrument and that connect the wrist mechanism to a transmission or actuator (also referred to herein as a backend mechanism). The backend mechanism moves the cables to operate the wrist mechanism. For computer-assisted systems, the backend mechanism is motor driven and can be operably coupled to a processing system to provide a user interface for a clinical user (e.g., a surgeon) to control the instrument.

Patients benefit from continual efforts to improve the effectiveness of MIS methods and tools. For example, reducing the size and/or the operating footprint of the main tube and wrist mechanism can allow for smaller entry incisions and reduced need for space at the surgical site, thereby reducing the negative effects of surgery, such as pain, scarring, and undesirable healing time. But, producing small medical instruments that implement the clinically desired functions for minimally invasive procedures can be challenging. Specifically, simply reducing the size of known wrist mechanisms by "scaling down" the components will not result in an effective solution because required component and material properties do not scale. For example, efficient implementation of a wrist mechanism can be complicated because the cables must be carefully routed through the wrist mechanism to maintain cable tension throughout the range of motion of the wrist mechanism and to minimize the interactions (or coupling effects) of one rotation axis upon another. Further, pulleys and/or contoured surfaces are generally needed to reduce cable friction, which extends instrument life and permits operation without excessive forces being applied to the cables or other structures in the wrist mechanism. Increased localized forces that may result from smaller structures (including the cables and other components of the wrist mechanism) can result in undesirable lengthening (e.g., "stretch" or "creep") of the cables during storage and use, reduced cable life, and the like.

Further, some medical instruments have end effectors that require electrical energy and optionally data communications for clinical functions such as desiccation, hemostasis, cutting, dissection, fulguration, incisions, tissue destruction, cauterizing, vessel sealing, and imaging. Accordingly, known instruments include one more non-drive wires (which function as conductors) routed through the wrist mechanism to the portion of an end effector to be energized and optionally controlled. Routing these non-drive wires through articulable members including wrist mechanisms and end effectors such that their movements are not limited can be challenging. In addition, routing these non-drive wires s through such articulable members without also increasing the risk of excess portions of the conductors being pinched or otherwise interfering with movements can be even more challenging. Further, fitting all the components of the wrist mechanism, drive cables, and conductors a small diameter, for example, less than about 10 mm, while providing sufficient flexibility for movements and while preserving the necessary strength and function of these components can also be difficult.

Another design requirement for medical instruments is the strength that opposing jaws can be closed against one another (e.g., for surgical clip application, etc.) or opened apart from one another (e.g., for blunt dissection, etc). For some instruments, a simple scissors design provides sufficient leverage to produce desired grip strength. For small instrument sizes, however, increased leverage is required to achieve high grip force. In some designs the necessary leverage is achieved by establishing a lever relationship between a jaw member and a rotating pulley that controls the jaw member's motion. For example, U.S. Pat. No. 6,206,903 B1 (filed Oct. 8, 1999) discloses an example of an instrument design that provides high grip strength in a compact design suitable for surgery. A limitation of this design is that it places additional components between the distal end of the instrument shaft and the gripping ends of the jaws. If the jaws' gripping surfaces are to receive electrosurgical energy, then these additional components block a path for an electrically conductive wire from the instrument shaft, through the grip mechanism components, to the electrically conductive jaw. One solution is to route an electrically conductive wire outside the leveraged instrument grip mechanism. But, this solution would require a wire loop that extends outside the outer diameter of the instrument, because a loop is required to accommodate wrist motion. Such a loop can be caught on a cannula during instrument insertion and withdrawal through the cannula, interfere with another instrument at the surgical site, be subject to cuts in insulation, etc.

Thus, a need exists for improved endoscopic tools. Improvements may include wrist mechanisms, especially wrist mechanisms with enhanced mechanical advantage, having one or more non-drive wires, such as electrically conductive wires, flexibly routed within the outer diameter boundaries of the wrist mechanisms to avoid adversely impacting movements of the wrist mechanisms. Further, improvements may also include efficiently routed non-drive wires within the wrist mechanisms to avoid increasing the likelihood of conductor material being pinched or otherwise interfering with moving components and their operations in the wrist mechanisms.

SUMMARY

This summary introduces certain aspects of the embodiments described herein to provide a basic understanding. This summary is not an extensive overview of the inventive subject matter, and it is not intended to identify key or critical elements or to delineate the scope of the inventive subject matter.

In some embodiments, an articulable medical device includes a link, a transfer member, a tool member, and a non-drive wire. The transfer member is coupled to a distal portion of the link. Further, the transfer member is coupled to a tension member such that the transfer member rotates relative to the link when the tension member is moved. The tool member has a base portion movably coupled to the transfer member, and a contact portion configured to engage a target tissue. The tool member is configured to move relative to the link between a first orientation and a second orientation when the tension member is moved. The non-drive wire has a first end portion, a second end portion, and a central portion between the first end portion and the second end portion. The first end portion is coupled to an energy source. The second end portion is coupled to the contact portion of the tool member. The central portion includes a transition portion disposed within a cavity defined within one of the base portion of the tool member, the distal portion of the link, or the transfer member. The transition portion has a compact first configuration when the tool member is in the first orientation and an expanded second configuration when the tool member is in the second orientation.

In some embodiments, the transition portion can be biased toward the compact first configuration and can be configured to expand against the bias when the tool member rotates from the first orientation to the second orientation. In some embodiments, the contact portion of the tool member can be electrically conductive and can be configured to contact the target tissue.

In some embodiments, the cavity is defined within the transfer member. In addition, the transfer member can include a rotatable pulley, and the cavity can be defined within a portion of the rotatable pulley. The rotatable pulley can include an outer surface about which the tension member is at least partially wrapped such that the pulley rotates relative to the link when the tension member is moved, and the cavity is defined by an inner surface of the pulley. Further, the rotatable pulley can be coupled to the link by a first pin that defines a first rotation axis, the pulley can be configured to rotate relative to the link about the first pin, and the tool member can be rotatably coupled to the pulley by a second pin that defines a second rotation axis, such that the tool member is configured to rotate relative to the pulley about the second pin, and the transition portion of the non-drive wire at least partially surrounds the first pin.

In some embodiments, the transition portion includes a pre-set non-linear arrangement of the non-drive wire when in the compact first configuration, and the transition portion is configured to return to the pre-set non-linear arrangement in the absence of tension in the longitudinal direction of the non-drive wire. Further, the pre-set non-linear arrangement can include a convoluted path. In addition, the pre-set non-linear arrangement can include a bight formed in the non-drive wire. The bight can include a coil, a loop, a fold or a bend formed in the non-drive wire.

In some embodiments, an articulable medical device includes a link, a first tool member, a non-drive wire, and a tension member. The first tool member is coupled to the link and has a contact portion and a pulley portion. The contact portion is electrically conductive and is configured to contact a target tissue. The pulley portion is rotatably coupled to the link and is rotatable relative to the link between a first orientation and a second orientation. A cavity is defined within the pulley portion. The non-drive wire has a first end portion, a second end portion, and a central portion between the first end portion and the second end portion. The first end portion is coupled to an energy source. The second end portion is coupled to the contact portion of the tool member. The central portion includes a transition portion and a feed portion. The transition portion is disposed within the cavity of the pulley portion. The transition portion expands from a relaxed first state to an extended second state when the first tool member rotates from the first orientation to the second orientation. The tension member is coupled to rotate at least one of the first tool member or a second tool member when the tension member is moved. The non-drive wire is coupled to the tension member such that movement of the tension member causes the feed portion to move from a first position outside of the cavity to a second position inside the cavity when the tension member moves to rotate at least one of the first tool member or the second tool member.

In some embodiments, the articulable medical device can further include a second tool member and a second tension member. The second tool member can be coupled to the link, and the second tool member can have a second contact portion and a second pulley portion. In addition, the second contact portion can be electrically conductive and to contact the target tissue, the second pulley portion can be rotatably coupled to the link, and the second tool member can be rotatable relative to the link. In addition, the first tension member can be coupled to the second pulley portion, and the second tool member can be configured to rotate relative to the link when the first tension member is moved. The second tension member can be coupled to the first pulley portion, and the first tool member can be configured to rotate relative to the link when the second tension member is moved.

In some embodiments, an articulable medical device includes a link, a first tool member, a second tool member, a non-drive wire, and a tension member. The first tool member is coupled to the link and has a first contact portion and a first pulley portion. The first contact portion is electrically conductive and is configured to contact a target tissue. The first pulley portion is rotatably coupled to the link and is rotatable relative to the link between a first orientation and a second orientation. The second tool member is coupled to the link and has a second contact portion and a second pulley portion. The second contact portion is electrically conductive and is configured to contact a target tissue. The second pulley portion is rotatably coupled to the link and is rotatable relative to the link. The non-drive wire has a first end portion, a second end portion, and a central portion between the first end portion and the second end portion. The first end portion is coupled to an energy source. The second end portion is coupled to the first contact portion. The central portion is configured to transition between a compact first configuration and an expanded second configuration. The central portion is in the compact first configuration when the first tool member is in the first orientation, and is in the expanded second configuration when the tool member is in the second orientation. The tension member is coupled to one of the first pulley portion or the second pulley portion. One of the first tool member or the second tool member is configured to rotate relative to the link when the tension member is moved. The non-drive wire is coupled to the tension member such that movement of the tension member causes a feed portion of the non-drive wire to be conveyed between the shaft and the first guide path.

Other medical devices, related components, medical device systems, and/or methods according to embodiments will be or become apparent to one with skill in the art upon review of the following drawings and detailed description. It is intended that all such additional medical devices, related components, medical device systems, and/or methods included within this description be within the scope of this disclosure.

BRIEF DESCRIPTION OF THE DRAWINGS

FIG. 5B is a diagrammatic side view of the portion of the instrument of FIG. 5A shown in a second orientation.

FIG. 5C is a diagrammatic side view of the portion of the instrument of FIG. 5A shown in a third orientation.

FIGS. 11A and 11B are perspective views of a first pulley of the instrument of FIG. 8.

FIG. 12A is a front perspective view of an end effector of the instrument of FIG. 8, shown in an open orientation.

FIG. 12B is a side perspective view of a second tool member of the end effector of FIG. 12A.

FIG. 16A is a perspective view of a first pulley of the instrument of FIG. 14.

FIGS. 16B and 16C are front and rear side views of the first pulley of FIG. 16A.

FIG. 17 is an enlarged perspective view of a distal end portion of an instrument in a first orientation, according to an embodiment, shown in a partial exploded view.

FIG. 18A is a perspective view of a first pulley of the instrument of FIG. 17.

FIGS. 18B and 18C are front and rear side views of the first pulley of FIG. 18A.

DETAILED DESCRIPTION

Figure 1:
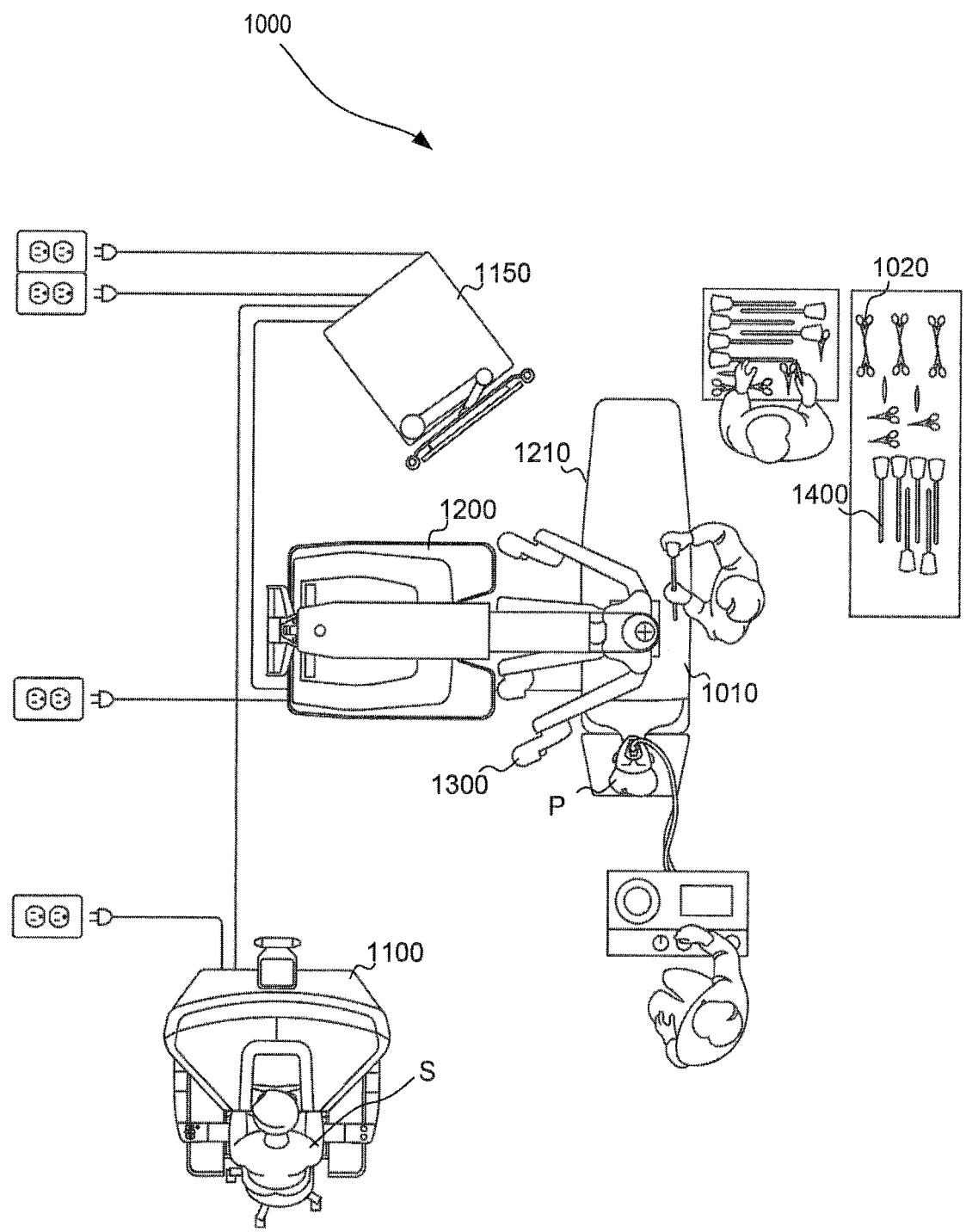
FIG. 1 is a plan view of a minimally invasive teleoperated medical system according to an embodiment, being used to perform a medical procedure such as surgery.

The embodiments described herein can advantageously be used in a wide variety of grasping, cutting, and manipulating operations associated with minimally invasive surgery. In particular, the instruments described herein can be low-cost, disposable instruments that facilitate being used for only one procedure. As described herein, the instruments include one or more cables (which act as tension members) that can be moved to actuate the end effector with multiple degrees of freedom. Moreover, the instruments include one or more non-drive wires routed through portions of the end effector.

As used herein, the term "about" when used in connection with a referenced numeric indication means the referenced numeric indication plus or minus up to 10 percent of that referenced numeric indication. For example, the language "about 50" covers the range of 45 to 55. Similarly, the language "about 5" covers the range of 4.5 to 5.5.

The term "flexible" in association with a part, such as a mechanical structure, component, or component assembly, should be broadly construed. In essence, the term means the part can be repeatedly bent and restored to an original shape without harm to the part. Certain flexible components can also be resilient. For example, a component (e.g., a flexure) is said to be resilient if possesses the ability to absorb energy when it is deformed elastically, and then release the stored energy upon unloading (i.e., returning to its original state). Many "rigid" objects have a slight inherent resilient "bendiness" due to material properties, although such objects are not considered "flexible" as the term is used herein.

A flexible part may have infinite degrees of freedom (DOF's). Flexibility is an extensive property of the object being described, and thus is dependent upon the material from which the object is formed as well as certain physical characteristics of the object (e.g., cross-sectional shape, length, boundary conditions, etc.). For example, the flexibility of an object can be increased or decreased by selectively including in the object a material having a desired modulus of elasticity, flexural modulus, and/or hardness. The modulus of elasticity is an intensive property of (i.e., is intrinsic to) the constituent material and describes an object's tendency to elastically (i.e., non-permanently) deform in response to an applied force. A material having a high modulus of elasticity will not deflect as much as a material having a low modulus of elasticity in the presence of an equally applied stress. Thus, the flexibility of the object can be decreased, for example, by introducing into the object and/or constructing the object of a material having a relatively high modulus of elasticity. Examples of such parts include closed, bendable tubes (made from, e.g., NITINOL®, polymer, soft rubber, and the like), helical coil springs, etc. that can be bent into various simple or compound curves, often without significant cross-sectional deformation.

Other flexible parts may approximate such an infinite-DOF part by using a series of closely spaced components that are similar to a serial arrangement of short, connected links as snake-like "vertebrae." In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOFs of relative movement between the links. A short, flexible part may serve as, and be modeled as, a single mechanical constraint (a joint) that provides one or more DOF's between two links in a kinematic chain, even though the flexible part itself may be a kinematic chain made of several coupled links having multiple DOFs, or an infinite-DOF link.

As used in this specification and the appended claims, the term "transfer member" refers to one or more components, linkages, parts and portions thereof coupled at a distal end to a tool member and at a proximal end to a link including one or more articulable portions through which a non-drive wire between the link and the tool member is transferred. In some embodiments, a transfer member can receive a force from the link and transfer at least a portion of the force to the tool member. In some embodiments, the term transfer member can refer to one or more portions of a series of components coupled to one another including a first link member (or portion(s) thereof) coupled to a shaft, a tool member (or portion(s) thereof), and a second link member (or portion(s) thereof located between the first link member and the tool member. In some embodiments, a transfer member can include a portion of a wrist mechanism coupled at a proximal end to a link coupled to a manipulator unit, and coupled to a tool member at a distal end. In some embodiments, the term transfer member can refer to a second link member coupled at a proximal end to a first link that is coupled to a manipulator unit, and coupled to a tool member at a distal end. In some embodiments, the term transfer member can further refer to one or more connectors such as pins, discs, and/or joints. In addition, the term transfer member can refer to one or more, fixed or movable, guide members such as guide paths, pulleys and/or guide surfaces. Further, a transfer member can define one or more cavities, such as a cavity formed by and/or within a pulley, a guide surface, a link, and/or a tool member.

As used in this specification and the appended claims, the word "bight" refers to a slack portion of an extended elongate member that is disposed between the ends of the extended elongate member and is configured to form at least one, or a series, of a bend, a loop, or a curve. As used in this specification and the appended claims, the word "slack" with respect to a portion of an elongate member refers to a portion that is one of expandable or extendable.

As used in this specification and the appended claims, the word "distal" refers to direction towards a work site, and the word "proximal" refers to a direction away from the work site. Thus, for example, the end of a tool that is closest to the target tissue would be the distal end of the tool, and the end opposite the distal end (i.e., the end manipulated by the user or coupled to the actuation shaft) would be the proximal end of the tool.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures were turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various spatial device positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

In addition, the singular forms "a", "an", and "the" are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups.

Unless indicated otherwise, the terms apparatus, medical device, instrument, and variants thereof, can be interchangeably used.

Aspects of the invention are described primarily in terms of an implementation using a da Vinci® Surgical System, commercialized by Intuitive Surgical, Inc. of Sunnyvale, California Examples of such surgical systems are the da Vinci Xi® Surgical System (Model IS4000) and the da Vinci Si® Surgical System (Model IS3000). Knowledgeable persons will understand, however, that inventive aspects disclosed herein may be embodied and implemented in various ways, including computer-assisted, non-computer-assisted, and hybrid combinations of manual and computer-assisted embodiments and implementations. Implementations on da Vinci® Surgical Systems (e.g., the Model IS4000, the Model IS3000, the Model IS2000, the Model IS1200) are merely presented as examples, and they are not to be considered as limiting the scope of the inventive aspects disclosed herein. As applicable, inventive aspects may be embodied and implemented in both relatively smaller, hand-held, hand-operated devices and relatively larger systems that have additional mechanical support.

FIG. 1 is a plan view illustration of a computer-assisted teleoperation system. Shown is a medical device, which is a Minimally Invasive Robotic Surgical (MIRS) system 1000 (also referred to herein as a minimally invasive teleoperated surgery system), used for performing a minimally invasive diagnostic or surgical procedure on a Patient P who is lying on an Operating table 1010. The system can have any number of components, such as a user control unit 1100 for use by a surgeon or other skilled clinician S during the procedure. The MIRS system 1000 can further include a manipulator unit 1200 (popularly referred to as a surgical robot), and an optional auxiliary equipment unit 1150. The manipulator unit 1200 can include an arm assembly 1300 and a tool assembly removably coupled to the arm assembly. The manipulator unit 1200 can manipulate at least one removably coupled tool assembly 1400 (also referred to herein as a "tool") through a minimally invasive incision in the body or natural orifice of the patient P while the surgeon S views the surgical site and controls movement of the tool 1400 through control unit 1100.

An image of the surgical site is obtained by an endoscope (not shown), such as a stereoscopic endoscope, which can be manipulated by the manipulator unit 1200 to orient the endoscope. The auxiliary equipment unit 1150 can be used to process the images of the surgical site for subsequent display to the Surgeon S through the user control unit 1100. The number of tools 1400 used at one time will generally depend on the diagnostic or surgical procedure and the space constraints within the operating room, among other factors. If it is necessary to change one or more of the instruments 1400 being used during a procedure, an assistant removes the instrument 1400 from the manipulator unit 1200 and replaces it with another instrument 1400 from a tray 1020 in the operating room. Although shown as being used with the instruments 1400, any of the instruments described herein can be used with the MIRS 1000.

Figure 2:
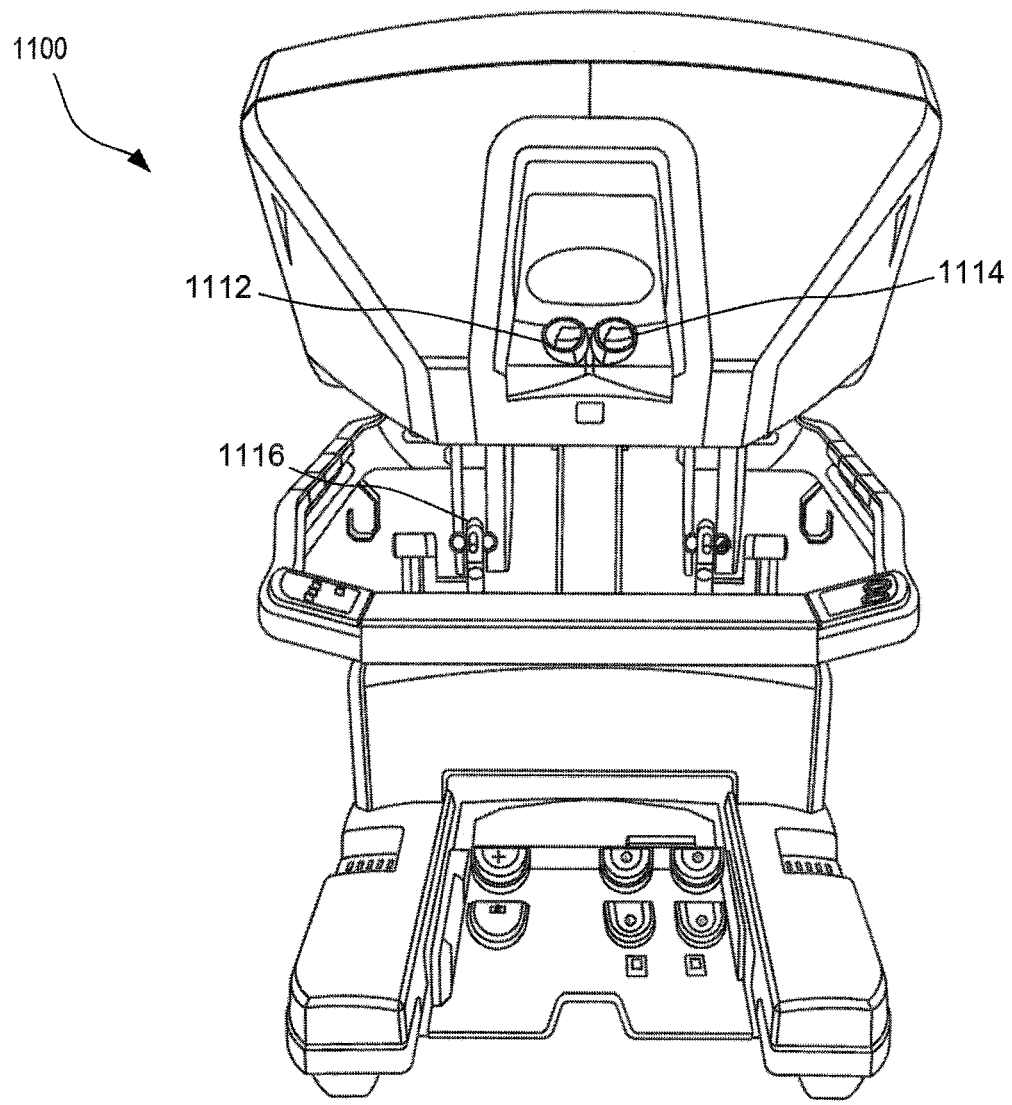
FIG. 2 is a perspective view of an optional auxiliary unit of the minimally invasive tele-operated surgery system shown in FIG. 1.

FIG. 2 is a perspective view of the control unit 1100. The user control unit 1100 includes a left eye display 1112 and a right eye display 1114 for presenting the surgeon S with a coordinated stereo view of the surgical site that enables depth perception. The user control unit 1100 further includes one or more input control devices 1116, which in turn cause the manipulator unit 1200 (shown in FIG. 1) to manipulate one or more tools. The input control devices 1116 provide at least the same degrees of freedom as instruments 1400 with which they are associated to provide the surgeon S with telepresence, or the perception that the input control devices 1116 are integral with (or are directly connected to) the instruments 1400. In this manner, the user control unit 1100 provides the surgeon S with a strong sense of directly controlling the instruments 1400. To this end, position, force, and tactile feedback sensors (not shown) may be employed to transmit position, force, and tactile sensations from the instruments 1400 back to the surgeon's hands through the input control devices 1116.

The user control unit 1100 is shown in FIG. 1 as being in the same room as the patient so that the surgeon S can directly monitor the procedure, be physically present if necessary, and speak to an assistant directly rather than over the telephone or other communication medium. In other embodiments however, the user control unit 1100 and the surgeon S can be in a different room, a completely different building, or other remote location from the patient allowing for remote surgical procedures.

Figure 3:
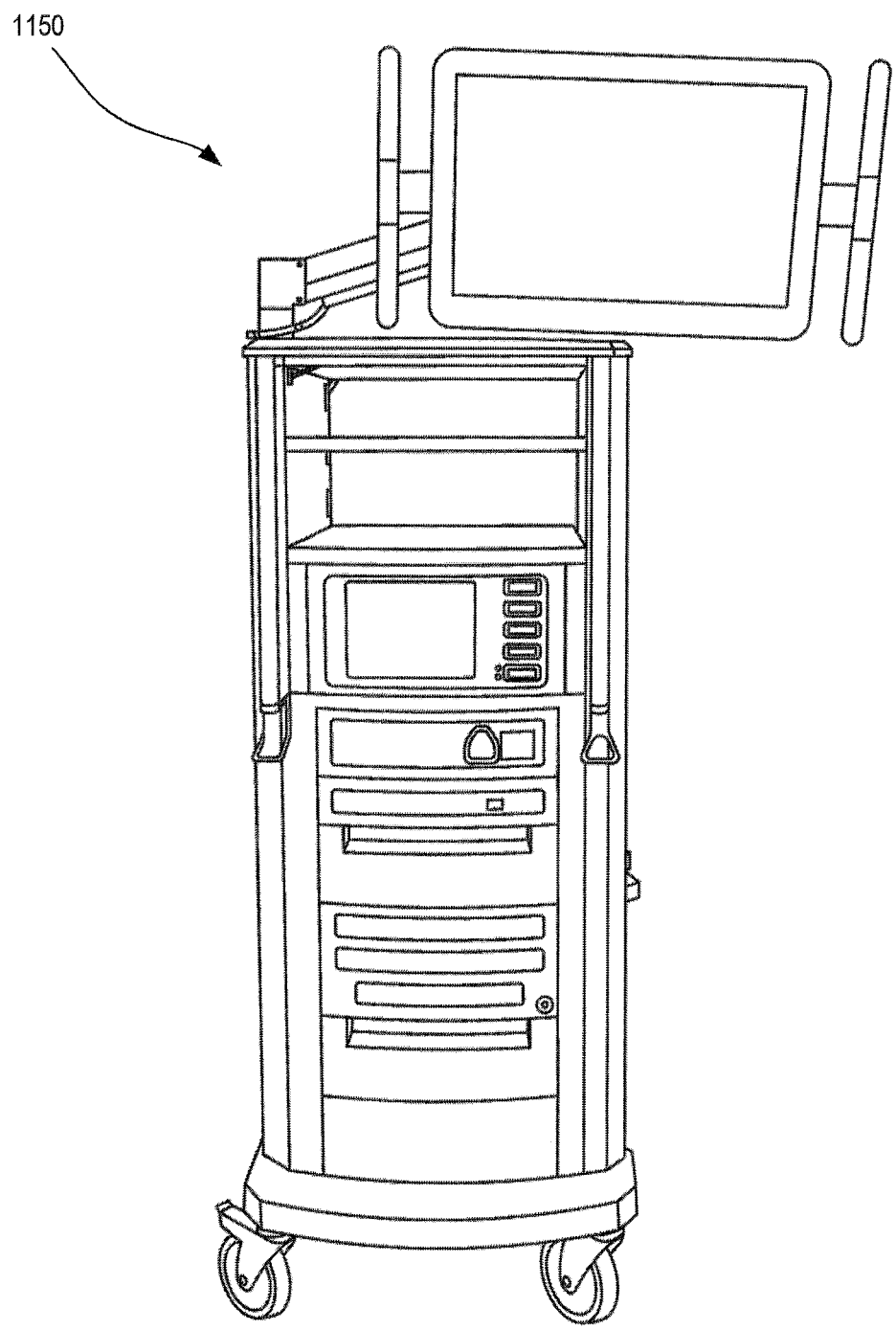
FIG. 3 is a perspective view of a user control console of the minimally invasive tele-operated surgery system shown in FIG. 1.

FIG. 3 is a perspective view of the auxiliary equipment unit 1150. The auxiliary equipment unit 1150 can be coupled with the endoscope (not shown) and can include one or more processors to process captured images for subsequent display, such as via the user control unit 1100, or on another suitable display located locally and/or remotely. For example, where a stereoscopic endoscope is used, the auxiliary equipment unit 1150 can process the captured images to present the surgeon S with coordinated stereo images of the surgical site via the left eye display 1112 and the right eye display 1114. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
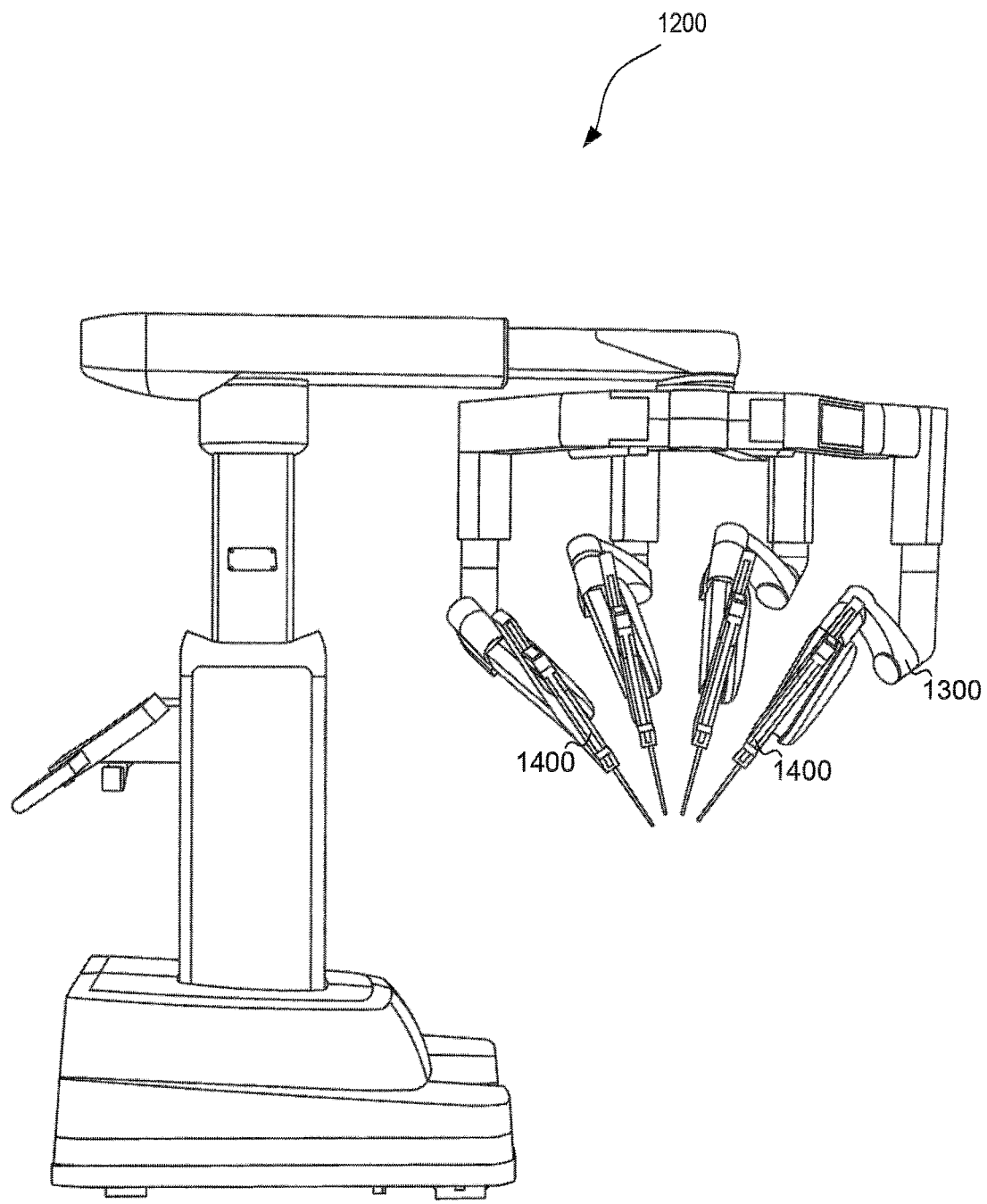
FIG. 4 is a front view of a manipulator unit, including a plurality of instruments, of the minimally invasive tele-operated surgery system shown in FIG. 1.

FIG. 4 shows a front perspective view of the manipulator unit 1200. The manipulator unit 1200 includes the components (e.g., arms, linkages, motors, sensors, and the like) to provide for the manipulation of the instruments 1400 and an imaging device (not shown), such as a stereoscopic endoscope, used for the capture of images of the site of the procedure. Specifically, the instruments 1400 and the imaging device can be manipulated by teleoperated mechanisms having a number of joints. Moreover, the instruments 1400 and the imaging device are positioned and manipulated through incisions or natural orifices in the patient P in a manner such that a kinematic remote center of motion is maintained at the incision or orifice. In this manner, the incision size can be minimized.

Figure 5A:
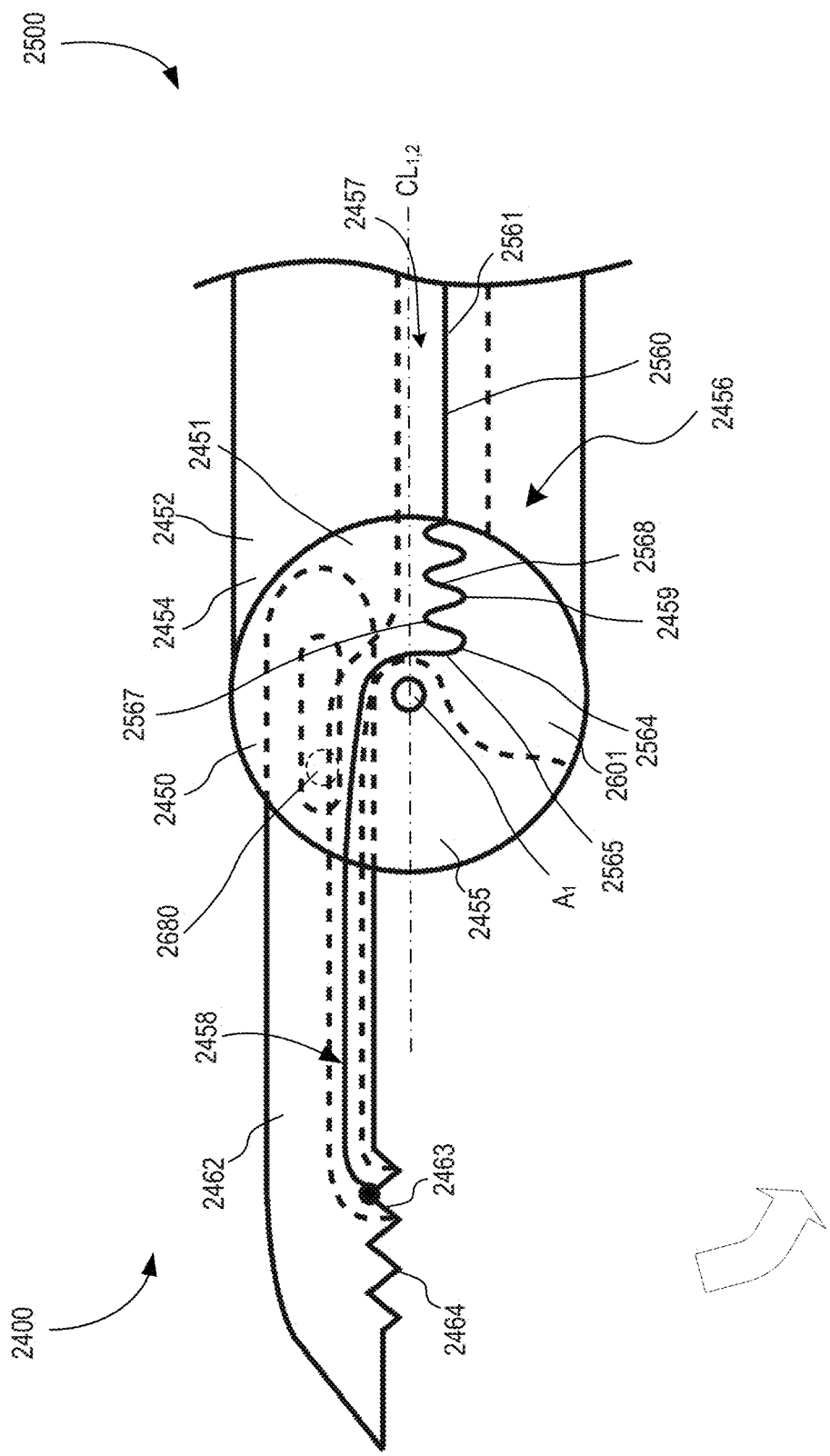
FIG. 5A is a diagrammatic side view of a portion of an instrument of a surgery system shown in a first orientation, according to an embodiment.

FIGS. 5A-5C are diagrammatic illustrations of various portions of an instrument 2400, according to an embodiment. In some embodiments, the instrument 2400 or any of the components therein are optionally parts of a surgical system that performs minimally invasive surgical procedures and which can include a manipulator unit, a series of kinematic linkages, a series of cannulas, or the like. The instrument 2400 (and any of the instruments described herein) can be used in any suitable surgical system, such as the MIRS system 1000 shown and described above. The instrument 2400 includes a link 2452, a transfer member 2450, a tool member 2462, and a non-drive wire 2560. The link 2452, the transfer member 2450, and the tool member 2462 together define a guide path 2456 through the instrument for the non-drive wire 2560. The instrument 2400 is intended to illustrate by way of example various aspects and features described herein. As such, it is understood that other components, parts, and connections (not shown) can be included in instrument 2400 and form portions of a wrist assembly or other articulable assembly. Moreover, the transfer member 2450 can be configured, for example, as one or more portions of components of an articulable portion of the instrument, rather than as a primary component or link member as is illustrated in the schematic example of instrument 2400. The simplified schematic drawings of FIGS. 5A-5C, as well as FIGS. 6A-6B, do not imply the existence or lack of additional components or any arrangements and connections there between, other than as described herein. The transfer member 2450 is configured to include appropriate components and portions of components that can cooperate to transfer effectively and flexibly the non-drive wire 2560 through an articulable portion of the instrument as described in greater detail below.

As discussed in greater detail below, the non-drive wire 2560 has a proximal end portion 2561, a distal end portion 2562, and a central portion 2564 disposed there between. The proximal end portion 2561 is coupled to an energy source (not shown), the distal end portion 2562 is coupled to the tool member 2462, and the central portion 2564 extends from the proximal end portion 2561 to the distal end portion 2562. Although only one non-drive wire 2560 is shown, one or more additional non-drive wires 2560 can be included. The non-drive wire 2560 can be coupled to any suitable energy source (not shown) of a surgical system, such as the MIRS system 1000 shown and described above. As such, non-drive wire 2560 acts as a powered conductor to convey electrical energy and optionally data communications from the surgical system to an end effector coupled to the transfer member 2450 to perform clinical functions, such as desiccation, hemostasis, cutting, dissection, fulguration, incisions, tissue destruction, cauterizing, vessel sealing, and imaging. As described herein, the instrument 2400 is configured for controlled movement in response to movements by one or more drive members (not shown) controlled by the surgical system, such as tension members, cables, pulley, guide members and the like.

The link 2452 has a distal end portion 2454, and a proximal end portion (not shown) that is coupled to a manipulator unit (not shown), such as manipulator unit 1200 shown in FIG. 4. The distal end portion 2454 of the link 2452 is articulably coupled to the transfer member 2450, such as rotatably coupled via one or more connectors. For example, the distal end portion 2454 can be connected to the transfer member 2450 via one or more rotatable joints, pins, hinges, discs, universal joints, as well as via flexible connectors such as multi-segmented serpentine links, flexible hinges including living hinges and polymeric connections, and the like. The link 2452 can include a link member, such as a metal fastener, connector, clevis, or other member, which can be fixedly attached to shaft (not shown) or other member coupled, for example, to the manipulator unit.

The transfer member 2450 includes a proximal end 2451, a distal end 2455, and a central portion 2453 located between the proximal and distal ends. The proximal end 2451 of the transfer member is coupled to the distal end 2454 of the link 2452 as described above. The distal end 2455 of the transfer member 2450 is coupled to a proximal portion 2467 of the tool member 2462 via a connector 2680. As discussed in greater detail below, the tool member 2462 is articulably coupled to the transfer member 2450. The transfer member 2450 can include a wide variety of components including connector components that can provide for various types of articulation movements between portions of the transfer member and/or portions of other members, such as between the distal end 2454 of the link 2452 and/or the proximal end portion 2467 of the tool member 2462. The connector components can further include, for example, one or more rotatable joints, pins, hinges, discs, universal joints, multi-segmented serpentine links, and flexible hinges including living hinges and polymeric connections, and the like. The transfer member 2450 can further include guide path components, such as guide path surfaces, fixed or rotatable guides for the one or more tension members (not shown) including pulleys and guide slots. In addition, the transfer member 2450 can define one or more guide paths including portions of the non-drive wire guide path 2456, one or more guide surfaces for the non-drive wire and/or tension members, and one or more guide pathways or channels for other movable components. The transfer member 2450 can also define or include other components and features as appropriate for supporting, articulating, moving, routing connections to, controlling, and/or communicating with the tool member 2462 for the tool member to perform its intended functions. In particular, the transfer member 2450 defines other features or includes additional components as appropriate for transferring effectively and flexibly the non-drive wire 2560 through the transfer member 2450 to the tool member 2462.

Referring now to FIGS. 5A and 5B, the instrument 2400 is configured such that the tool member 2462 can be controlled to articulate through at least two motions with respect to the link 2452 via the transfer member 2450. In particular, the proximal end 2451 of the transfer member 2450 is rotatably coupled to the distal end 2454 of the link 2452 to form a wrist joint that can rotate the tool member 2462 from a first orientation shown in FIG. 5A to a second orientation shown in FIG. 5B about an axis of rotation, $A_1$. In a first orientation shown in FIG. 5A, the centerline $CL_1$ of the link 2452, and the centerline $CL_2$ of the transfer member 2450 are collinear. In a second orientation shown in FIG. 5B, the centerline $CL_1$ of the link 2452 forms an angle $\angle \beta$ with the centerline $CL_2$ of the transfer member 2450. Thus, the transfer member 2450 rotates with the tool member 2462, but rotates relative to the link 2452, when moving from the first orientation shown in FIG. 5A to the second orientation shown in FIG. 5B. The transfer member 2450 can be rotated relative to the link 2452, for example, by movement of a tension member (not shown) coupled to the transfer member 2450. The tension member can be any tension member shown and described herein, such as the tension member 3420 described below. Thus, the transfer member 2450 can receive a force applied by the moving tension member and move the tool member 2462 in response to the force.

The slotted connector 2680 of the transfer member 2450 is coupled to a slot of the tool member 2462 such that the tool member 2462 can translate relative to the transfer member 2450, but also rotates along with the transfer member 2450 about axis $A_1$. The slotted connector 2680 can be any suitable connector to translatably couple the tool member 2462 to the transfer member 2450 and form a sliding tool member joint. As shown in FIGS. 5A and 5C, the tool member 2462 is configured to translate distally and proximally in a direction toward and away from the transfer member 2450. Although shown as being a slotted connector 2680 that facilitates translation, in other embodiments, the transfer member 2450 can include any suitable connector to movably couple the tool member 2462 to the transfer member 2450.

The tool member 2462 includes a proximal portion 2467 and an opposite distal contact portion 2463. As described above along with the transfer member 2450, the proximal portion 2467 is movably coupled to the transfer member to articulate proximally and distally with respect to the transfer member. The contact portion 2463 is configured to contact, and optionally to engage, a target tissue (not shown). As described further below, the contact portion 2463 is electrically connected to an end of the non-drive wire 2560. The tool member 2462 can optionally include an electrically conductive engagement surface 2464 that is electrically connected to the contact portion 2463 and is configured to engage the target tissue, such as to cut, clamp, press against, or otherwise engage the target tissue in addition to making contact with the target tissue. In some embodiments, the tool member 2462 can include a scalpel or other cutting device having an electrically conductive engagement surface 2464, such as a cutting edge 2464, wherein distal and proximal movements of the tool member 2462 can occur as part of cutting operations that engage the target tissue.

A guide path 2456 for the non-drive wire 2560 is defined at least by the link 2452, the transfer member 2450, and the tool member 2462. A proximal end portion 2457 of the guide path 2456 provides a path for the non-drive wire 2560 as it extends from its connection to the energy source (not shown) through the link 2452. As such, link 2452 defines at least a portion of the proximal end portion 2457 of the guide path. A central portion 2459 of the guide path extends distally from the proximal end portion 2457 of the guide path 2456, through an articulation portion of the instrument 2400, to a distal end portion 2458 of the guide path located proximate the contact portion 2463 of the tool member 2462. As such, the transfer member 2450 defines a portion of the central portion 2459 of the guide path 2456. The distal end portion 2458 of the guide path 2456 extends to the contact portion 2463 of the tool member 2462. As such, the tool member defines a portion of the distal end portion 2458 of the guide path 2456.

The transfer member 2450 further defines a cavity 2601 within the central portion 2459 of the guide path 2456, which can be formed as an enlarged portion of the guide path 2456 that is located within the transfer member 2450. As discussed in greater detail below, the cavity 2601 can be configured to retain a transition portion 2567 of the non-drive wire 2560. In some embodiments, the cavity 2601 is located proximate the rotatable joint formed along the axis of rotation $A_1$ without including the joint, but in other embodiments the cavity can also include the joint and a corresponding axis (see e.g., FIGS. 14-16C, 17-19B and 23-25). As shown in FIGS. 5A-5C, the cavity can extend distally inward from the proximal end 2451 of the transfer member to the central portion 2453 of the transfer member. However, it is understood that the cavity can be configured, located and shaped in various arrangements as appropriate for the instrument, for the routing of the non-drive wire 2560 therein, for the amount, type and location of articulable movements, and based on other factors, such as are discussed herein. For example, in some embodiments, the cavity 2601 can be defined by the tool member 2462, the link 2452, or any combination of the transfer member 2450, the tool member 2462, and the link 2452. The cavity 2601 as shown in FIGS. 5A-5C is located at the proximal end 2451 of the transfer member 2450 at a proximal end of the cavity, and extends distally toward the central portion 2453 such that its distal end is proximate the joint located at axis $A_1$. The cavity 2601 is configured to be aligned with a distal end portion of the guide path 2456 at the distal end 2454 of the link 2452 throughout the range of rotation of the transfer member 2450, including as it moves from the first orientation (FIG. 5A) to the second orientation (FIG. 5B). Thus, the cavity 2601 is configured to have a general arc shape corresponding with rotation of the transfer member from the first orientation to the second orientation.

The non-drive wire 2560 includes a proximal end portion 2561, a distal end portion 2562, and a central portion 2564 located between the proximal and distal end portions. The non-drive wire 2560 can be configured as an insulated conductor having an insulated outer jacket (not shown) and one or more conductive wires (not shown) located within the outer jacket. The proximal end portion 2561 is coupled to, and is electrically connected to, an energy source (not shown) of the surgical system, such as the MIRS system 1000 shown and described above. The distal end portion 2562 is coupled to, and electrically connected to, the contact portion 2463 of the tool member, such that the contact portion 2463 is electrically connected to the power source (not shown) of the surgical system. The non-drive wire 2560 is routed through the guide path 2456, as described above.

The central portion 2564 of the non-drive wire 2560 includes a transition portion 2567 located within the cavity 2601 within the transfer member 2450. As shown in FIG. 5A, the transition portion 2567 has a compact first configuration that is configured to store a slack portion of the non-drive wire 2560 in an expandable, compact arrangement when the transfer member 2450 and the tool member 2462 are in the first orientation. The transition portion 2567 includes the non-drive wire 2560 forming a convoluted path including one or more bends, loops, curves, coils, or other curvilinear shapes 2568, or serial arrangements or combinations of the same. In some embodiments, the transition portion 2567 includes a bight when in the compact first configuration. In some embodiments, the transition portion can be in a relaxed state when in the compact first configuration. Further, in some embodiments, the transition portion 2567 can be biased toward the compact first configuration.

The instrument 2400 is configured to route the non-drive wire 2560 in an efficient curvilinear manner that closely follows its designated route through the instrument via the guide path 2456. The instrument does so without having slack portions that form bends extending outside of the transition portion 2567. The transition portion 2567 is located proximate an articulable connection along the instrument 2400 including at the rotatable connection between the link 2452 and the transfer member 2450, and near the translatable connector 2680 that slidably connects the transfer member to the tool member 2462. In such an arrangement, the formation of excess bends or other regions of slack material of the non-drive wire 2560 are avoided. Such excess slack material is undesirable because it can be caught by portions of the articulable instrument 2400 during movements of the wrist assembly 2500. Further, in such an arrangement, sufficient flexibility is also provided by the transition portion 2567 located proximate the one or more articulation locations such that the non-drive wire 2560 does not limit the range of motions of the articulable instrument 2400. Examples of these benefits are illustrated in the movements shown in FIGS. 5A-5C. Although the non-drive wire 2560 is shown as including one transition portion 2567, in other embodiments a non-drive wire can include any suitable number of transition portions.

Referring to FIGS. 5A and 5B, articulable instrument 2400 is shown when in the non-rotated first orientation (FIG. 5A) and in the rotated second orientation (FIG. 5B), in which the transfer member 2450 rotates counterclockwise by $\angle\beta$ about axis $A_1$ with respect to the link 2452 (e.g., about 90 degrees). When in the first orientation of FIG. 5A, the transition portion 2567 is in the first compact configuration within the cavity 2601 and is located proximate to axis $A_1$. Further, the transition portion 2567 includes a plurality of bends 2568 arranged in series when in the first orientation. The first compact configuration of FIG. 5A is a relaxed state, and in some embodiments, the transition portion 2567 can be biased to return when there is a lack of tension in the longitudinal direction of the non-drive wire. Such bias toward the first compact configuration of FIG. 5A can be provided by the bends 2568 having been formed as bends that exceed the elastic limit of the conductive wire that have been induced in the non-drive wire 2560 at the transition portion, such that the conductive wire is deformed to retain the bends when in the relaxed state. It is understood that such a bias can be provided by any appropriate mechanism including by having different configurations of expandable folds or loops formed therein (see e.g., FIGS. 10, 19A, 19B and 23-25), and/or via the use of a biasing mechanism (not shown). For example, a biasing member can include an elastic band formed around at least part of the transition portion, a shaped elastomeric jacket formed around the non-drive wire within the transition portion, or an elastic compressive member integrated with the non-drive wire within the transition portion. When in the first compact configuration, the transition portion can further include a release portion 2565 located within the cavity 2601 that is configured to move out of the cavity when the transition portion expands from the first compact configuration.

When the transfer member 2450 rotates to the second orientation shown in FIG. 5B, the transition portion 2567 expands to the second expandable configuration shown in FIG. 5B, which releases a length of the non-drive wire 2560 appropriate to avoid the non-drive wire from limiting the rotation. As shown in FIG. 5A as an example, the release portion 2565 can be located within the cavity 2601 at a distal end of the transition portion 2567 proximate an exit portion of the cavity. When the transfer member 2450 is rotated to the second orientation shown in FIG. 5B, the release portion 2565 can move at least partially out of the cavity 2601, such that it is located at the exit portion of the cavity and extends into the distal end portion 2458 of the guide path 2456 defined within the tool member 2462. As is further shown in FIG. 5B, the transition portion 2567 releases a length of the non-drive wire by extending to an expanded second configuration having, for example, fewer bends 2568 and/or the bends with less amplitude and frequency than in the compact first configuration. As such, a shorter length of the non-drive wire 2560 is retained by the transition portion 2567.

The transition portion 2567 further extends to the second expanded configuration shown in FIG. 5C as the tool member 2462 articulates again to translate distally away from the transfer member 2450 along the pinned connection 2680. The further extension of the transition portion releases an additional length of the non-drive wire 2560 that is appropriate to avoid the non-drive wire 2560 from limiting the distal translation. When the tool member 2462 is translated distally away from the transfer member 2450 to the third orientation shown in FIG. 5C, the release portion 2565 can move, for example, out of the cavity 2601 and distally along the guide path 2456 toward the tool member 2462. As is further shown in FIG. 5C, the transition portion 2567 releases the additional length of the non-drive wire by further extending to the expanded second configuration of FIG. 5C. In the expanded second configuration, the transition portion 2567 has fewer, if any, bends 2568 in comparison with the first expanded configuration of FIG. 5B, and any remaining bends have less amplitude with reduced frequency.

Figure 6A:
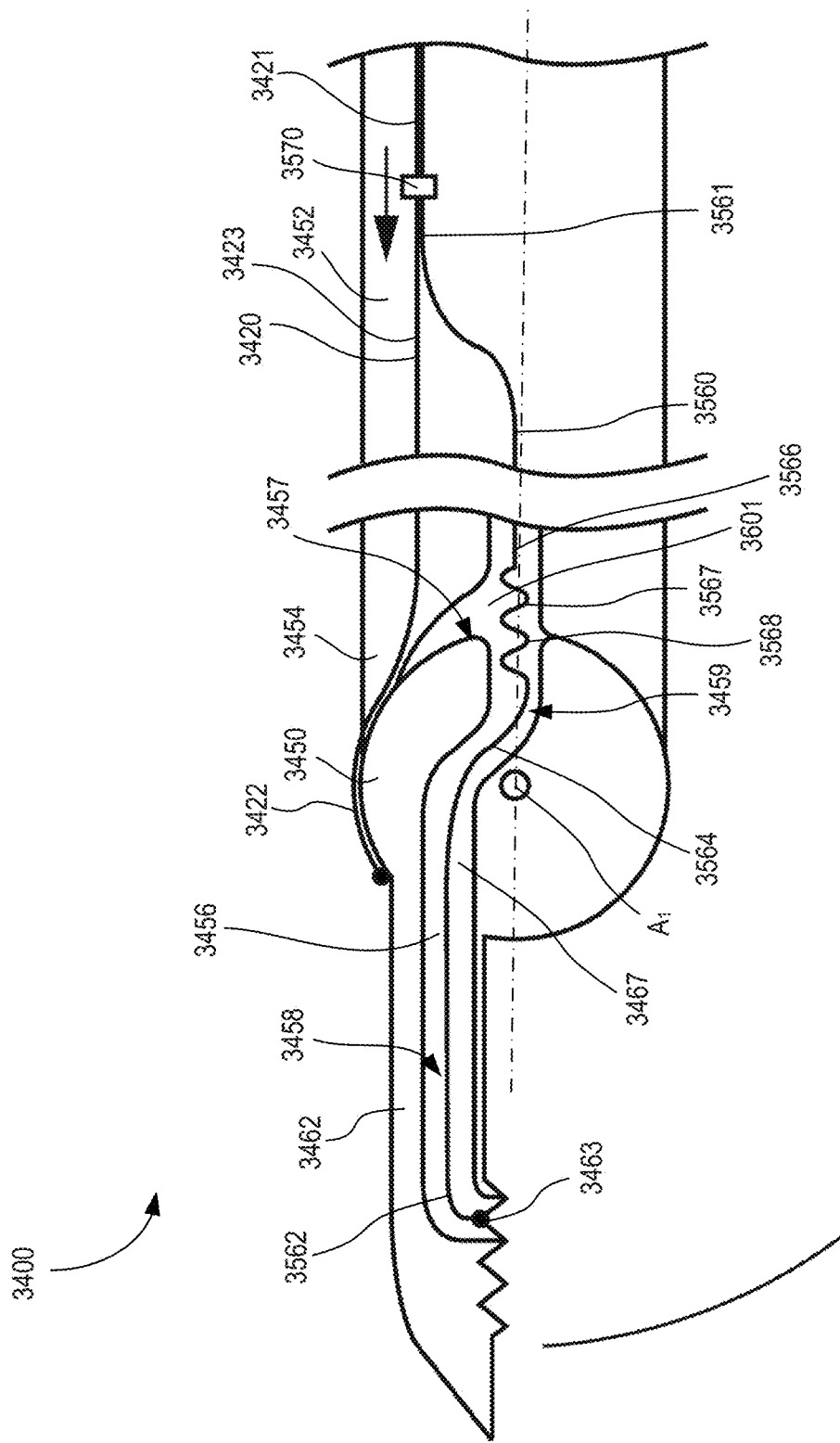
FIG. 6A is a diagrammatic side view of a portion of an instrument of a surgery system shown in a first orientation, according to an embodiment.
Figure 6B:
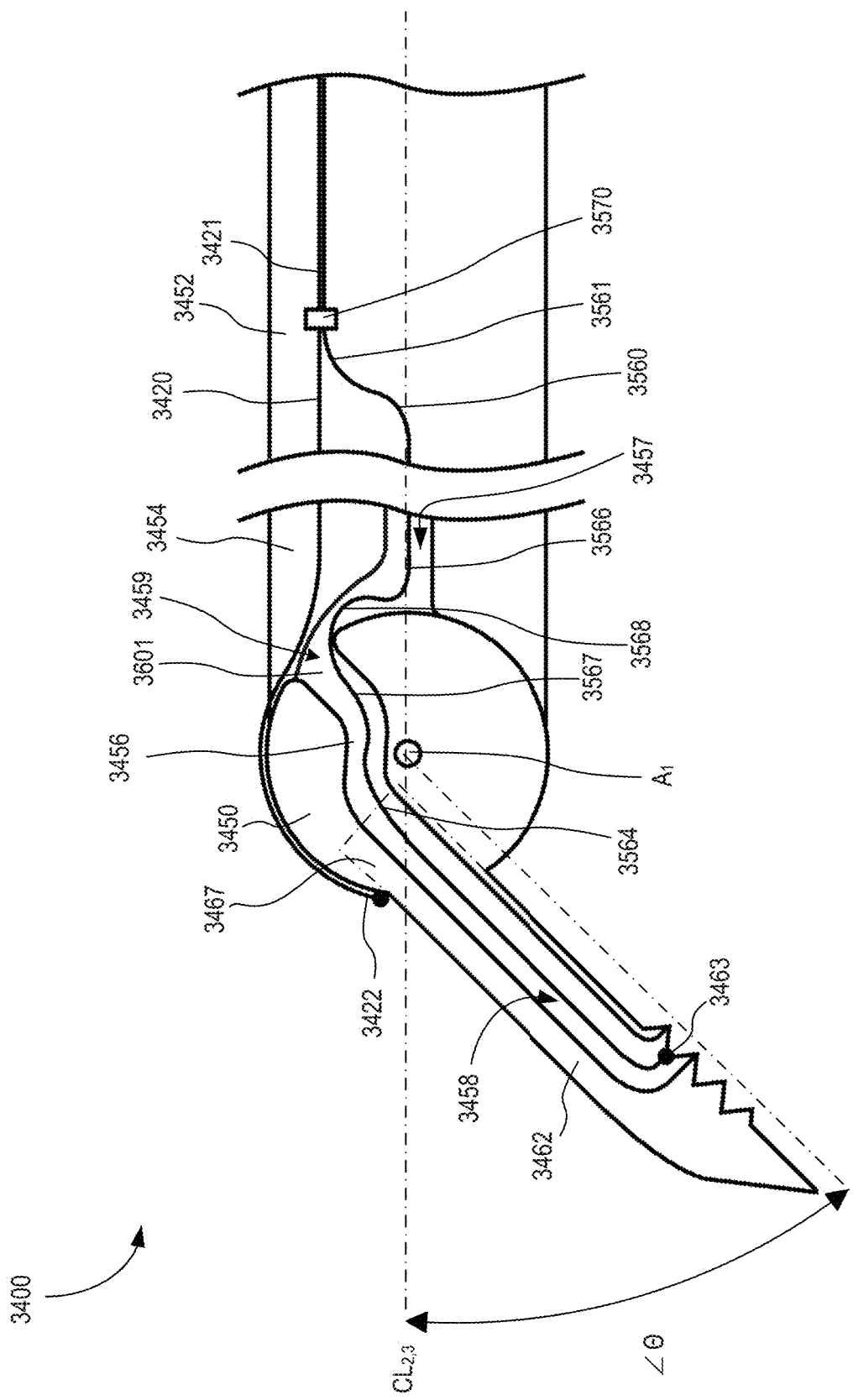
FIG. 6B is a diagrammatic side view of the portion of the instrument of FIG. 6A shown in a second orientation.
Figure 6B:
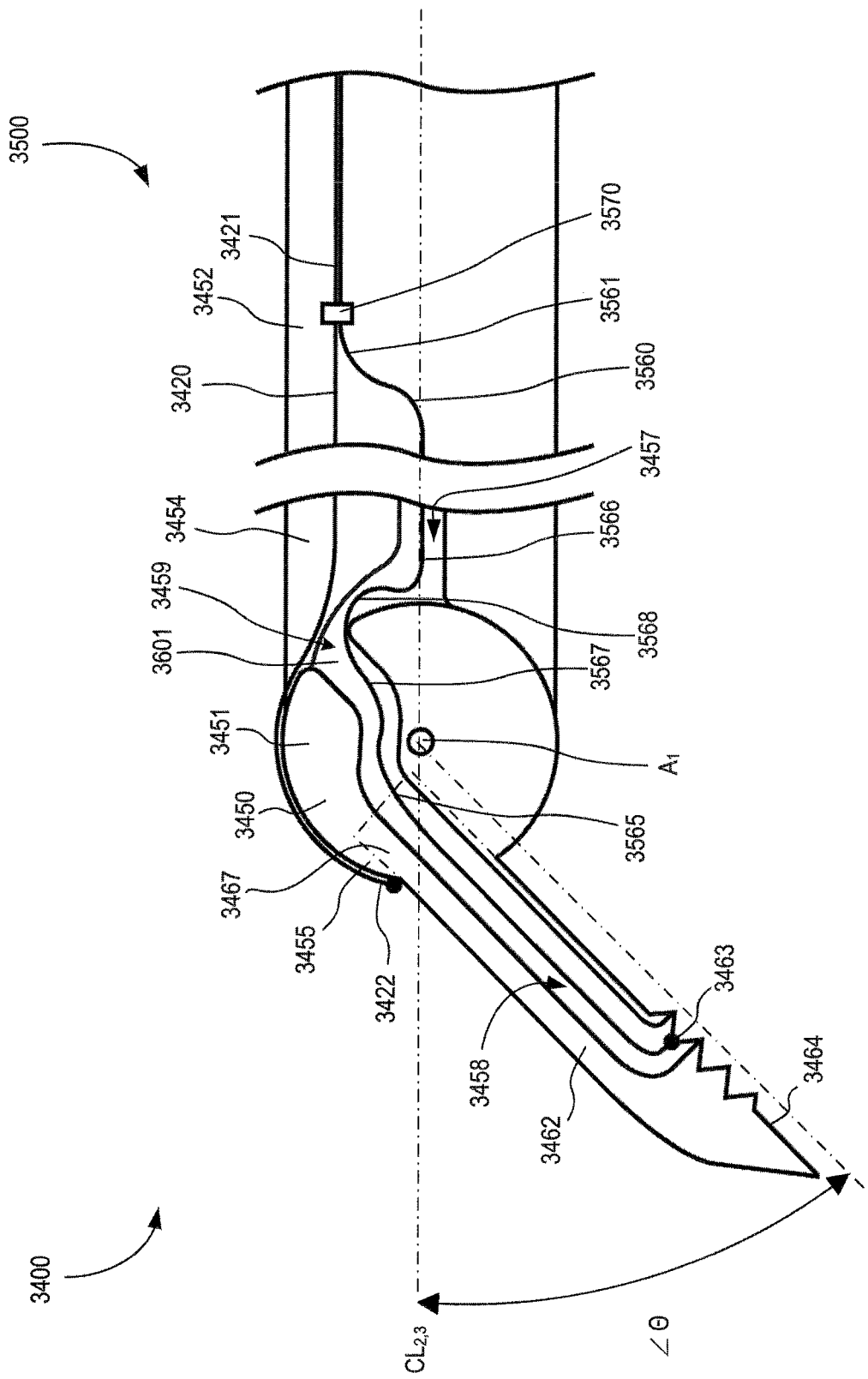

In addition to providing transition portions along the length of the non-drive wire, additional non-drive wire guide mechanisms can be provided to route the non-drive wire in an efficient curvilinear manner that closely follows its designated route through the instrument without having slack portions that can form bends. Such guide mechanisms can operate alone, or in combination with, the transition portions that are configured to provide flexibility for the non-drive wire when needed for articulable instrument movements. As an example, an articulable medical instrument can also include one or more feed mechanisms configured to assist with providing flexibility to the non-drive wire for the articulation movements of the medical instrument. The one or more feed mechanisms can push or urge additional portions of the non-drive wire to move distally along its route within the instrument to provide flexibility as needed for articulation movements of the instrument, as well as to avoid limiting the articulation movements. FIGS. 6A and 6B are schematic drawings showing an example instrument 3400 having a feed mechanism that operates in combination with one or more transition portions to provide efficient routing and articulation flexibility for a non-drive wire routed there through. Similar to instrument 2400, instrument 3400 or any of the components therein are optionally parts of a surgical system that performs minimally invasive surgical procedures and which can include a patient-side cart, a series of kinematic linkages, a series of cannulas, or the like. The instrument 3400 (and any of the instruments described herein) can be used in any suitable surgical system, such as the MIRS system 1000 shown and described above.

Referring to FIGS. 6A and 6B, the instrument 3400 is shown, which is similar to instrument 2400 and generally includes the same preferences and features as described above along with instrument 2400 except as described hereafter. Accordingly, like numbers refer to like features as described above. As with instrument 2400, instrument 3400 also includes a link 3452, a transfer member 3450, a tool member 3462, and a non-drive wire 3560, in which the non-drive wire 3560 is coupled to an energy source (not shown) of the surgical system, such as the MIRS system 1000 shown and described above. In addition, instrument 3400 includes at least one tension member 3420. The instrument 3400 is configured for controlled movement in response to movements by one or more tension members including the tension member 3420, and/or by one or more additional drive members (not shown) that are controlled by the surgical system, such as additional tension members, cables, pulleys, guide members and the like.

Instrument 3400 also differs from instrument 2400 in that the link 3452 and the tool member 3462 together define a guide path 3456 through the instrument for the non-drive wire 3560, and the transfer member 3450 can be configured, for example, as one or more portions thereof. As such, the transfer member 3450 can include articulable portions of the link 3452 and the tool member 3462 as appropriate to flexibly and efficiently transfer the non-drive wire 3560 through an articulable portion of the instrument as described in greater detail below. As such, the link 3452 defines therein a proximal end portion 3457 of the guide path 3456 for the non-drive wire 3560. Likewise, a distal portion of the guide path 3456 can be defined through the tool member 3462. Similar to instrument 2400, the tool member 3462 includes a distal contact portion 3463, which is electrically conductive and is configured to contact a target tissue (not shown). In addition, the tool member 3462 also includes a pulley portion 3467 at its proximal end portion. The pulley portion 3467 is rotatably coupled to the link 3452 in a similar manner as the rotatable connection along axis $A_1$ between the transfer member 2450 and the link 2452 of instrument 2400. For example, the pulley portion 3467 can be rotatably coupled to the link, such as via a pinned connection, a joint, a flexible connector, a rotatable assembly or other device or combination of devices. The tool member 3462 can define therein a distal end portion 3458 of the guide path 3456 for the non-drive wire 3560, which can couple with the central portion 3459 defined in the link 3452. A cavity 3601 is also defined within the pulley portion 3467 along a portion of the central portion 3459 of the guide path 3456. Although the instrument 3400 is described as including both a transfer member 3450 and a tool member 3462 having a pulley portion 3467, in some embodiments, the instrument 3400 can include only a pulley portion to accomplish the actuation of the tool member 3462 when the tension member 3420 is moved. Although the pulley portion 3467 is described as being separate from the transfer member, in some embodiments, the pulley portion 3467 can monolithically constructed as a part of the tool member, and can function as the transfer member.

The non-drive wire 3560 has a proximal end portion 3561, a distal end portion 3562, and a central portion 3564 disposed therebetween. The proximal end portion 3561 is coupled to an energy source (not shown), the distal end portion 3562 is coupled to the tool member 3462, and the central portion 3564 extends from the proximal end portion 3561 to the distal end portion 3562. Although only one non-drive wire 3560 is shown, one or more additional non-drive wires 3560 can be included. The non-drive wire 3560 can be coupled to any suitable energy source (not shown) of a surgical system, such as the MIRS system 1000 shown and described above. Similar to instrument 2400, the central portion 3564 of the non-drive wire 3560 includes a transition portion 3567, which is disposed within the cavity 3601 within the pulley portion 3467 of the tool member 3462. In addition, the central portion 3564 of the non-drive wire 3560 also includes a feed portion 3566 that is located outside of the cavity 3601 when the instrument 3400 is in the first orientation shown in FIG. 6A.

Referring now to FIGS. 6A and 6B, the instrument 3400 is configured such that the tool member 3462 can be controlled to articulate through at least one motion with respect to the link 3452 via the transfer member 3450. As discussed above, the pulley portion 3467 of the tool member 3462 is rotatably coupled to the distal end 3454 of the link 3452 to form a wrist joint that can rotate the tool member 3462 with respect to the link about axis $A_1$. The tool member 3462 can be rotated from a first orientation shown in FIG. 6A to a second orientation shown in FIG. 6B about the axis of rotation, $A_1$. Moreover, the tool member 3462 can be rotated relative to the link 3452 when tension member 3420 is moved, which in the embodiment shown is coupled to the tool member 3462. However, the tension member 3420 can optionally be coupled to a second tool member (not shown) in an alternative arrangement, and can also be coupled to the tool member 3462 and the second tool member. Additionally, in some embodiments, the tension member 3420 can be coupled to a separate transfer member 3450 that transfers the force from the tension member to the tool member 3462.

In some embodiments, the tension member 3420 (and any of the tension members described herein) can be formed as a cable made of Tungsten or stainless steel to provide sufficient strength, bendability, and durability. In some embodiments, cables can be constructed from multiple braids of fine wire, to provide strength and resiliency. In some embodiments, cables can be made from 150 to 350 braids of 0.0007-inch to 0.001-inch (0.01778 mm to 0.0254 mm) diameter tungsten wire providing cables with outer diameters of 0.014 inches to 0.018 inches (0.3556 mm to 0.4572 mm). In some embodiments the instrument 3400 (and any of the instruments described herein) can include a tension band, of the types shown and described in U.S. Patent Application No. 62/598,620 (filed Dec. 14, 2017), entitled "Medical Tools Having Tension Bands," which is incorporated herein by reference in its entirety. In some embodiments, such bands (and any of the tension members described herein) can have a trapezoidal shape. In other embodiments, such bands (and any of the tension members described herein) can include slightly curved surfaces. Moreover, such bands (and any of the tension members described herein) can be constructed from any suitable materials. For example, in some embodiments, such bands (and any of the tension members described herein) can be constructed from a series of laminates that are bonded together (e.g., via an adhesive). The laminates can be constructed from any suitable material, including tungsten, steel, or any suitable polymer. The tension member 3420 has a proximal end portion 3421, a distal end portion 3422 coupled to the tool member 3462, and a central portion 3423 between the proximal and distal end portions. The proximal end portion 3421 can be coupled to the surgical system at a first end thereof (not shown), such as the MIRS system 1000 shown and described above.

The tension member 3420 is coupled to the tool member 3462 to rotate the tool member 3462 when the tension member moves. Thus, the instrument 3400 can be configured, for example, such that when the tension member 3420 moves in the distal direction indicated by the arrows in FIGS. 6A and 6B, the tool member 3462 rotates from the first orientation shown in FIG. 6A to the second orientation shown in FIG. 6B. The tension member 3420 and the tool member 3462 are coupled to each other so that when the tension member moves in the distal direction of the instrument 3400, the tool member 3462 rotates from the first orientation to the second orientation.

Referring to FIGS. 6A and 6B, the articulable instrument 3400 is shown in FIG. 6A when in the non-rotated first orientation, and in FIG. 6B when in the rotated second orientation after the tool member 3462 has rotated counterclockwise by $\angle \theta$ about axis $A_1$ with respect to the link 3452. When in the first orientation of FIG. 6A, the transition portion 3567 of the non-drive wire 3560 is in a relaxed state and the feed portion 3566 is located outside of the cavity 3601. When the tool member 3462 rotates to the second orientation shown in FIG. 6B, the transition portion 3567 expands to the second expandable configuration shown in FIG. 6B, which releases a length of the non-drive wire 3560 appropriate to avoid the non-drive wire from limiting the rotation. As is further shown in FIG. 6B, the transition portion 3567 releases a length of the non-drive wire by extending to an extended second state having, for example, fewer bends 3568 and/or the bends with less amplitude and frequency than in the compact first configuration. As such, a shorter length of the non-drive wire 3560 is retained by the transition portion 3567.

In addition, movement of the tension member 3420 as shown in FIGS. 6A and 6B also causes the feed portion 3566 of the non-drive wire 3560 to move from a first position outside of the cavity 3601 as shown in FIG. 6A, to a second position inside of the cavity when the tension member 3420 moves to rotate the tool member 3462. Specifically, the tension member 3420 is coupled to the non-drive wire 3560 such that movement of the tension member 3420 causes the feed portion 3566 to move from its first position to its second position when the tension member 3420 moves. In this manner, the tension member 3420 can assist in moving the non-drive wire to avoid the non-drive wire from limiting the rotation or otherwise producing excess lengths that can become pinched. The tension member 3420 can be coupled to the non-drive wire 3560 in any suitable manner and at any suitable location. For example, in some embodiments, a proximal end 3421 of the tension member can be coupled to the proximal end portion 3561 or the central portion 3564 of the non-drive wire 3560. The tension member 3420 can be coupled to the non-drive wire via a connector 3570 that connects the tension member to the non-drive wire along a length of each. The connector 3570 can be any appropriate connector for sufficiently coupling the non-drive wire 3560 to the tension member 3420. Such a connector can be configured so that when the tension member moves to rotate the tool member 3462, the tension member additional moves (i.e., pulls) the non-drive wire via the connector 3570 to move the feed portion 3566 distally toward the cavity 3601. In some embodiments, the connector 3570 can include an elastomeric connector that can surround both the tension member and the non-drive wire, such as a shrink wrap type connector. As such, the movement of the tension member 3420 can push the non-drive wire 3560 to move the feed portion 3566 into the cavity 3601 when the tool member 3462 rotates from the first orientation to the second orientation.

Thus, the instrument 3400 can operate in a push-pull manner to provide flexibility for portions of the non-drive wire 3560 that are routed through articulable portion of the instrument 3400 during movements of the instrument. As such, the instrument 3400 can be configured to route the non-drive wire 3560 in an improved, curvilinear manner that can more closely follow its designated route through the instrument via the guide path 3456 compared with configurations providing only push or pull functionality to help improve the flexibility of the non-drive wire routed therethrough with respect to articulation movements of the instrument. Thus, excess slack material along the non-drive wire can be avoided more effectively, while also providing sufficient flexibility when needed during articulation movements based on the combination of the expandable transition portion 3567 located within the cavity 3601, and the tension member 3420 moving an additional length of the non-drive wire into the cavity during such movements including moving the feed portion 3566.

In some embodiments, beneficial arrangements of a transfer member that effectively and flexibly routes a non-drive wire through an articulable portion of an instrument can be provided for more complex instruments and drive arrangements. For example, beneficial aspects and features pertaining to a transfer member described above can be used for routing a non-drive wire through a complex, amplified force drive arrangement for an instrument 4400 having a relatively complex amplified force driving arrangement for a pair of tool members to which a corresponding pair of non-drive wires are attached. As described in greater detail below, the instrument 4400 includes a transfer member that effectively routes the non-drive wires through the articulation portions of the amplified force drive mechanism along with providing appropriate flexibility for the non-drive wires during articulation movements of drive mechanism.

FIGS. 7-13 show various views of an instrument 4400, according to an embodiment, which generally includes the same preferences and features as described above along with instruments 2400 and 3400 except as described hereafter. Accordingly, like numbers refer to like features as described above. In some embodiments, the instrument 4400 or any of the components therein are optionally parts of a surgical assembly that performs minimally invasive surgical procedures, and which can include a manipulator unit, a series of kinematic linkages, a series of cannulas, or the like. The instrument 4400 (and any of the instruments described herein) can be used in any suitable surgical system, such as the MIRS system 1000 shown and described above. The instrument 4400 includes a transmission assembly 4700 (that can function as an actuator mechanism), an instrument shaft 4410, a wrist assembly 4500, and an end effector 4460.

As with instruments 2400 and 3400, instrument 4400 also includes a link configured as a proximal first link 4510, a pulley 4660 (that functions as a transfer member), a tool member 4462 formed as part of an end effector 4460, and a non-drive wire 4560 that is coupled to an energy source (not shown) of the surgical system, such as the MIRS system 1000 shown and described above. In addition, instrument 4400 further includes a second tool member 4482 that is also part of the end effector 4460. Each of the pair of tool members are coupled to the second link 4610 in an opposing relationship with each other, so that the pair of tool members can cooperate with each other to clamp, grasp, or otherwise interface with a target tissue (not shown). In addition, the instrument 4400 also includes a second non-drive wire 4580 that corresponds with the second tool member 4482, which is similarly coupled to the second tool member 4482 at one end portion and to an energy source (not shown) at another end portion. Thus, the pair of tool members 4462, 4482 can each make contact with the target tissue (not shown), and become energized while each are in contact with the target tissue such that an electrical current can flow through the tissue to cauterize or otherwise affect the tissue.

The instrument 4400 further includes one or more tension members (not shown), which have been omitted in FIGS. 7-13 to more clearly show features pertaining to the non-drive wires 4560 and 4580 and routing of the same via the pulley 4660. However, the instrument 4400 generally includes multiple tension members (not shown) that couple the transmission mechanism 4700 to the wrist assembly 4500. The instrument 4400 is configured such that movement of the tension members can produce rotation of the wrist assembly 4500 (i.e., pitch rotation) about a first axis of rotation, $A_1$, yaw rotation of the end effector 4460 about a second axis of rotation, grip rotation of the tool members of the end effector 4460 about the yaw axis $A_2$, or any combination of these movements. Thus, the instrument 4400 is configured to perform a variety of articulation movements along portions of the wrist assembly 4500 and the end effector 4460. As such, it can be challenging to route the one or more non-drive wires 4560, 4580 through the articulable portions of the wrist assembly 4500 to the tool members 4462, 4482 located at the distal end of the instrument. Moreover, it can be even more difficult to route the non-drive wires in a manner that avoids adversely affecting the articulation movements of the instrument 4400, and that avoids excess slack portions of the non-drive wire gathering within the instrument 4400.

As described below along with FIG. 10, the instrument 4400 also includes a force-amplification arrangement within the wrist assembly 4500 that employs mechanical advantage principles to amplify the forces applied to the end effector 4460. Although beneficial for increasing the applied force at the end effector 4460 while maintaining a small form factor for the instrument 4400, such an arrangement can add complexity to the drive and the linkage components located within the wrist assembly 4500 and the end effector 4460. In addition, the use of more complex articulation components can reduce available space within the instrument 4400 that could be used for routing the non-drive wires and other components, and can also increase the likelihood of interference between internal components and the non-drive wires during articulation movements involving additional components moving in a tighter space. Thus, the pulley 4660 and the pulley 4665 can be highly beneficial for desired operation and movements of the instrument 4400. In particular, as described above along with instruments 2400 and 3400, and as discussed in greater detail below, the pulleys 4660, 4665 are configured to efficiently route the non-drive wires 4560, 4580 through the articulation portions of the instrument 4400, as well as to maintain the non-drive wires within their guide paths during articulation movements. Doing so can avoid interfering contact between the non-drive wires and moving components, and can further provide flexibility for the non-drive wires during articulation movements such that the non-drive wires avoid limiting the ranges and types of movements that can be performed by the instrument 4400. These features can be particularly beneficial for articulable portions of an instrument that include complex linkages and drive members, such as force amplification features as described below along with FIG. 10.

The transmission mechanism 4700 produces movement of the plurality of tension members (not shown), which operate to produce the desired articulation movements (pitch, yaw, or grip) at the wrist assembly 4500. Specifically, the transmission mechanism 4700 includes components and controls to move some of the tension members in a proximal direction (i.e., to pull in certain tension members) while simultaneously allowing the distal movement (i.e., releasing or "paying out") of other of the tension members in equal lengths. In this manner, the transmission mechanism 4700 can maintain the desired tension within the tension members, and can ensure that the lengths of the tension members are conserved (i.e., moved in equal amounts) during the entire range of motion of the wrist assembly 4500. In some embodiments, for example, the transmission assembly 4700 can be any of the transmission assemblies shown and described in International Patent Application No. PCT/US2017/062258, (filed Nov. 14, 2017), entitled "Cable Length Conserving Medical Instrument," which is incorporated herein by reference in its entirety. In other embodiments however, conservation of the lengths of the tension members is not required.

Figure 7:
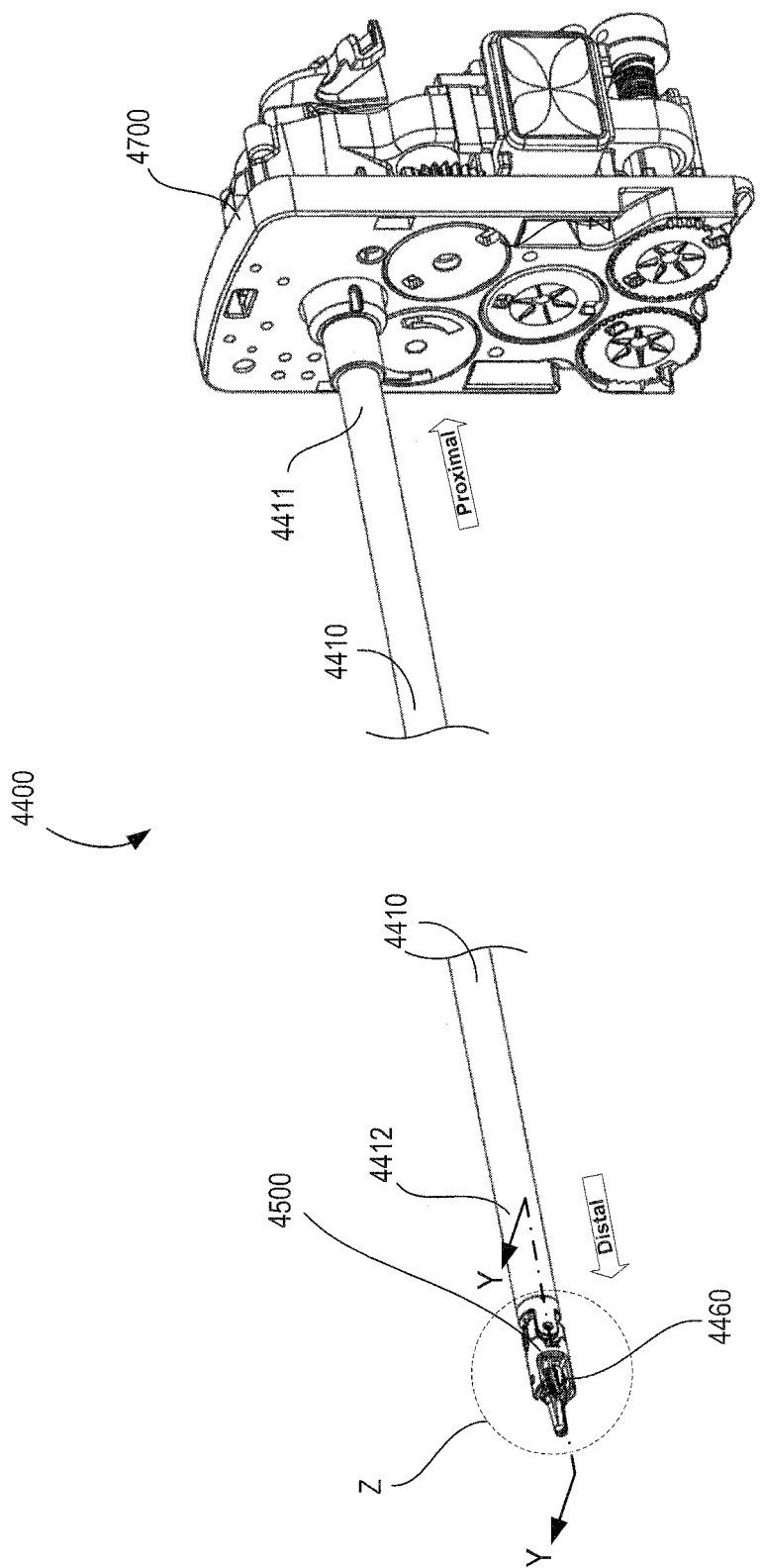
FIG. 7 is a perspective view of an instrument of a surgery system in a first orientation, according to an embodiment.

Referring now to FIG. 7, the articulable wrist mechanism 4500 of the instrument 4400 is coupled to the shaft 4410, which can be any suitable elongated shaft that couples the wrist assembly 4500 to the transmission mechanism 4700. Specifically, the instrument shaft 4410 includes a proximal end portion 4411 that is coupled to a housing of the transmission mechanism 4700, and a distal end portion 4412 that is coupled to the wrist assembly 4500. The instrument shaft 4410 defines a passageway or series of passageways through which the tension members, the non-drive wires 4560, 4580 and other components (e.g., electrical wires, ground wires, or the like) can be routed from the transmission mechanism 4700 to the wrist assembly 4500. These passageways or series of passageways include portions of the guide paths for routing the non-drive wires 4560 and 4580 as discussed in more detail below. Although shown as being cylindrical, in other embodiments the instrument shaft 4410 can have any suitable shape.

Figure 8:
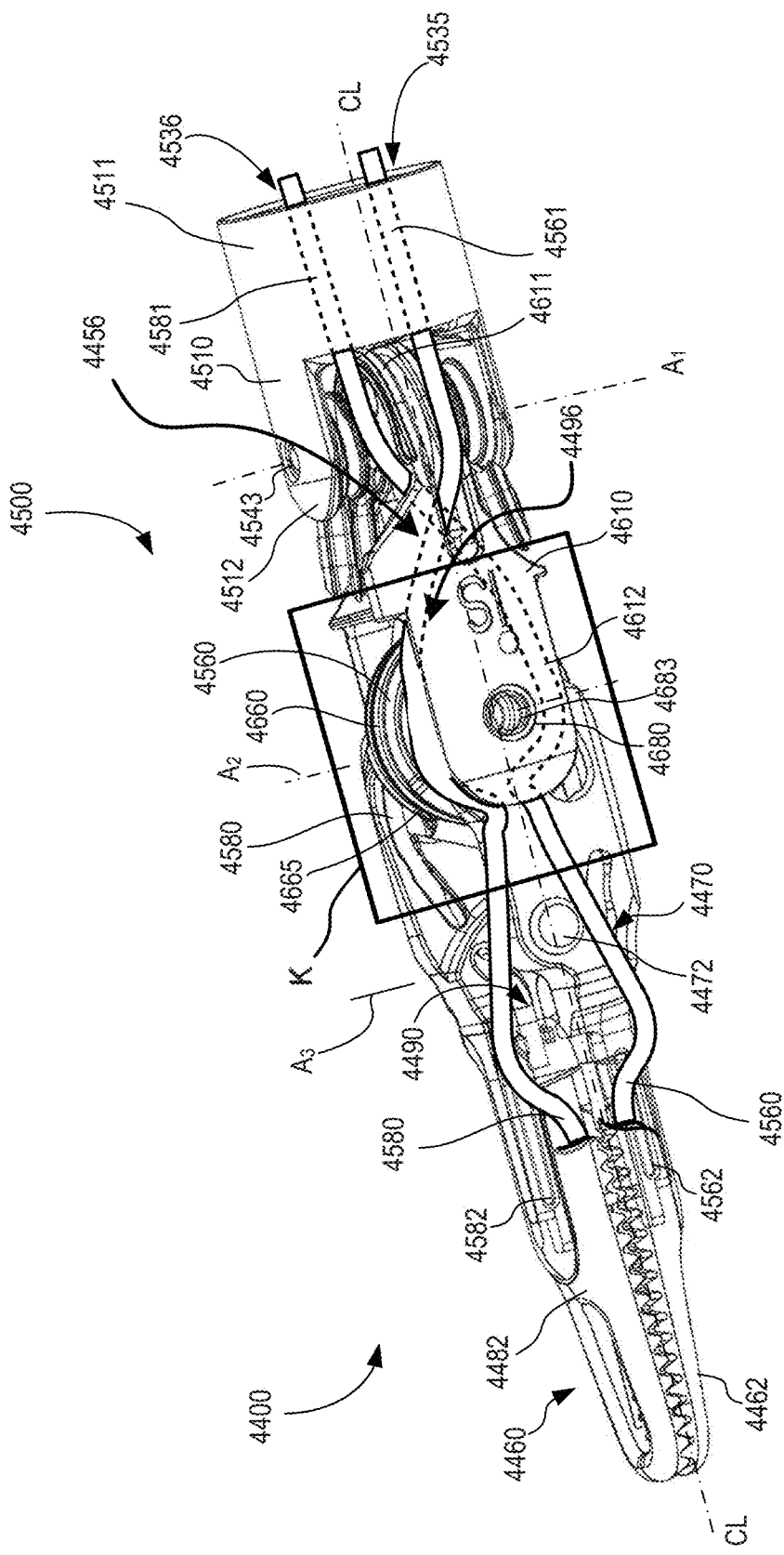
FIG. 8 is an enlarged perspective view of a distal end portion of the instrument in the first orientation indicated by the region Z shown in FIG. 7, according to an embodiment.
Figure 9:
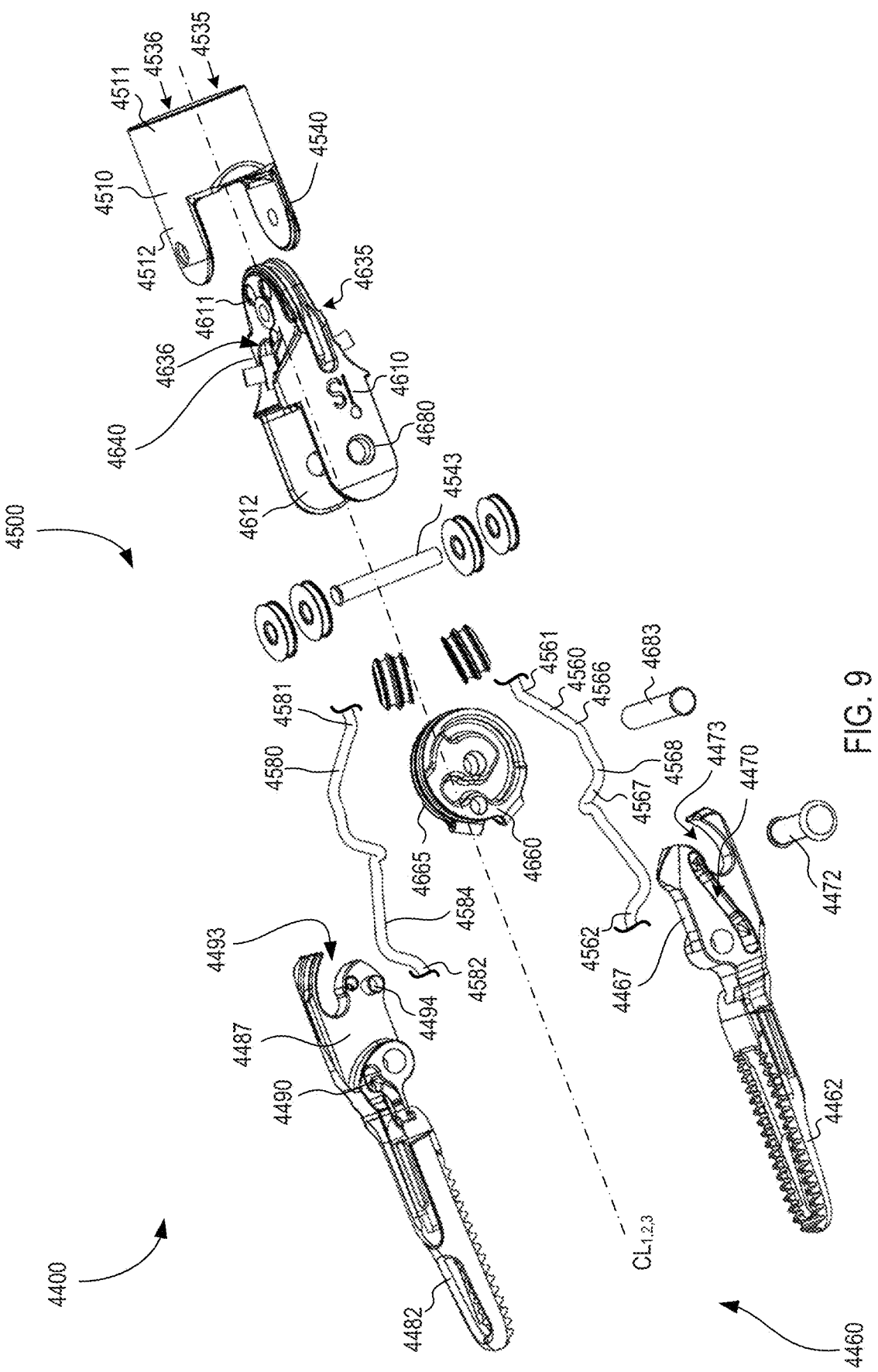
FIG. 9 is a perspective view of the distal end portion of the instrument of FIG. 8 shown in an exploded view.

Referring now to FIGS. 8 and 9, the wrist assembly 4500 includes a proximal first link 4510 and a distal second link 4610, which is articulably coupled to an end effector 4460. The first link 4510 has a proximal end portion 4511 and a distal end portion 4512. The proximal end portion 4511 is coupled to the distal end portion 4412 of the instrument shaft 4410. The distal end portion 4512 includes a joint portion 4540 that is rotatably coupled to a mating joint portion 4640 of the second link 4610. In this manner, the first link 4510 and the second link 4610 form the wrist assembly 4500 having a first axis of rotation $A_1$ (also referred to as the pitch axis) about which the second link 4610 can rotate relative to the first link 4510. A pin 4543 extends through the distal end joint portion and the second link joint portion to rotatably couple the second link 4610 to the first link 4510. As shown in FIG. 8, the first link 4510 and the second link 4610 define a longitudinal centerline CL that intersects the pitch axis $A_1$ when the instrument is in an initial (or "straight" configuration). The first link 4510 defines various bores and/or guide paths that can contain (or allow passage of) various components of the wrist assembly including the non-drive wires as discussed below, as well as, for example, bores and guide paths for the tension members (not shown) and various electrical components and connections.

The distal second link 4610 has a proximal end portion 4611 and a distal end portion 4612. The proximal end portion 4611 includes a joint portion 4640 that is rotatably coupled to the joint portion 4540 of the first link 4510. The distal end portion 4612 of the second link 4610 includes a connector 4680 that is coupled to the end effector 4460. In this manner, the first tool member 4462 and the second tool member 4482 of the end effector 4460 can rotate relative to the second link 4610 about a second axis of rotation (also referred to as the yaw axis). The connector 4680 is a pin-type connector and includes the pin 4683 which is supported by (and placed within) the pin openings. In some embodiments, the connector 4680 can include any of the structure and features of the pinned joints shown and described in U.S. Pat. No. 9,204,923 B2 (filed Jul. 16, 2008), entitled "Medical Instrument Electronically Energized Using Drive Cables," which is incorporated herein by reference in its entirety. As shown in FIG. 8, the second axis of rotation (also referred to as the yaw axis) is non-parallel to the pitch axis $A_1$. Thus, the instrument 4400 provides for up to three degrees of freedom (i.e., a pitch motion about the first axis of rotation $A_1$, a yaw rotation about a second axis of rotation, and a grip motion about the second axis of rotation).

Referring now to FIG. 9, the first and second tool members 4462 and 4482 of the end effector 4460 each include a contact portion 4463, 4483 and a proximal portion 4467, 4487 coupled to a respective pulley 4660, 4665. The contact portions 4463, 4483 are each configured to engage or manipulate a target tissue (not shown) during a surgical procedure. Although shown as being a gripping surface, in other embodiments, the contact portions 4463, 4483 can be any suitable surface of the types shown and described herein (e.g., a cutter, a tissue manipulator, a cauterizing surface, or the like). The pulleys 4660, 4665 are each rotatably coupled to the second link 4610 via the pin 4683. As described along with FIG. 10, each pulley 4660, 4665 functions as a transfer member to drive movement of a corresponding one of the tool members 4462, 4482 when rotated, such as when a tension member (not shown) applies a tensile force along a perimeter portion of a pulley. In this manner, the first and second tool members 4462, 4482 can each rotate about the pin 4683 and relative to the second link 4610 via a second axis of rotation as described in further detail below along with FIG. 10. As such, application of a force by the corresponding tension members (not shown) to each of the pulleys 4660, 4665 can produce a torque on the first tool member 4462 and the second tool member 4482 about a yaw axis, which can result in rotation of the first tool member 4462 and the second tool member 4482, or the application of a gripping force between the tool members.

Figure 13:
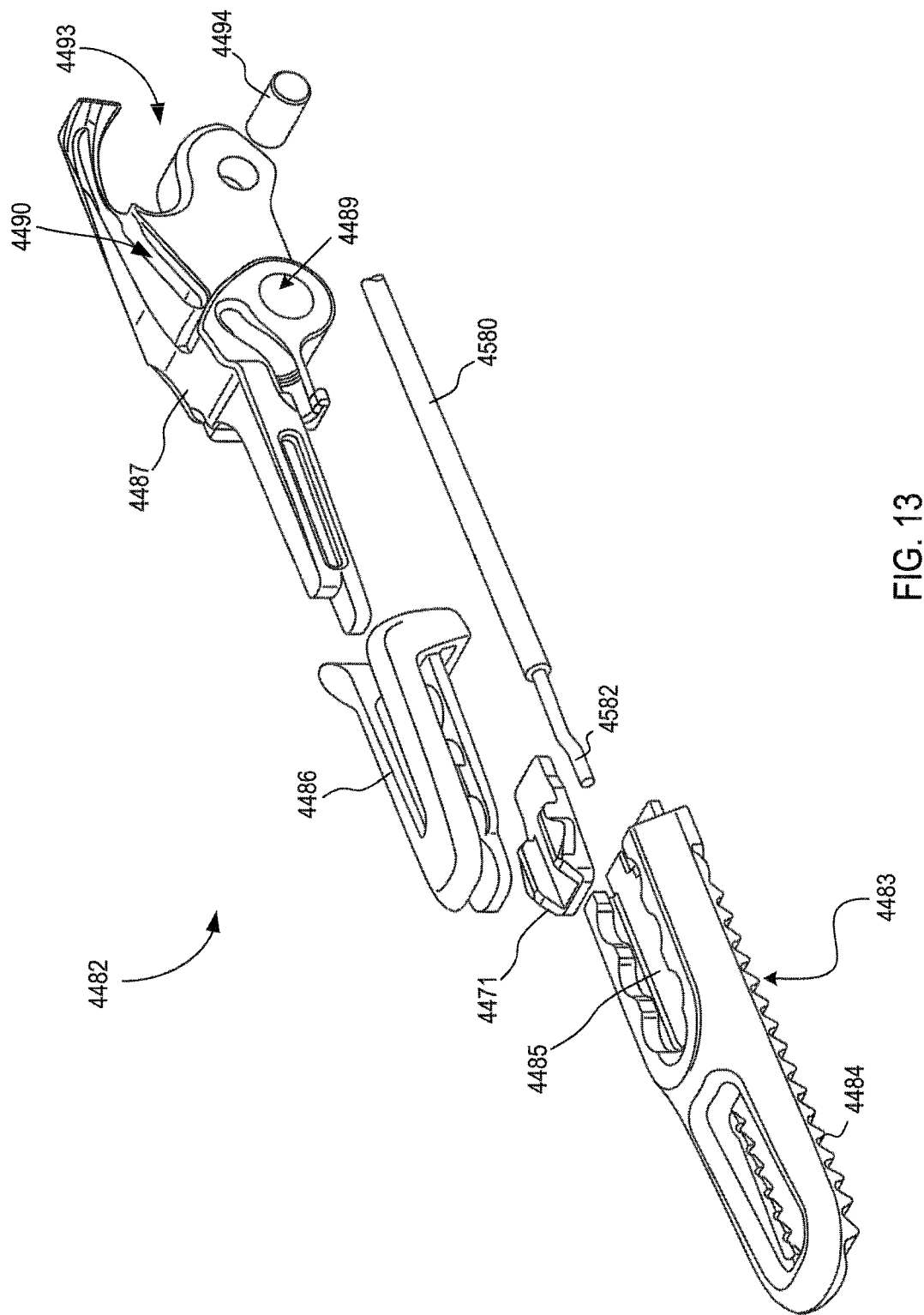
FIG. 13 is a side perspective view of the end effector of FIG. 12A, shown in an exploded view.

Referring to FIG. 8, each of the non-drive wires 4560, 4580 are highlighted in FIG. 8 to show the route of each of the non-drive wires within the instrument 4400. The non-drive wires are shown as overlays on the wrist mechanism 4500 and the end effector 4460 for clarity purposes. However, it is understood that each of the non-drive wires 4560, 4580 are routed within the guide paths defined therein as discussed in below. As shown in FIG. 8, each of the non-drive wires 4560, 4580 includes a corresponding proximal end portion 4561, 4581 at one end that is coupled to an energy source (not shown), and which extends through one or more guide pathways (not shown) defined within the shaft 4410 to the articulable wrist mechanism 4500. Further, as shown in FIG. 13 for the tool member 4482 (which is similar for the tool member 4462) each of the non-drive wires 4560, 4580 are coupled at an opposite distal end portion 4562, 4582 to the contact portion 4463, 4483 of the engagement surface 4484 of a corresponding one of the tool members 4462, 4482. Each of the non-drive wires 4560, 4580 further includes a central portion 4564, 4584 that is located between the corresponding distal end portion and the proximal end portion for the particular non-drive wire as it extends through the instrument 4400.

Figure 10:
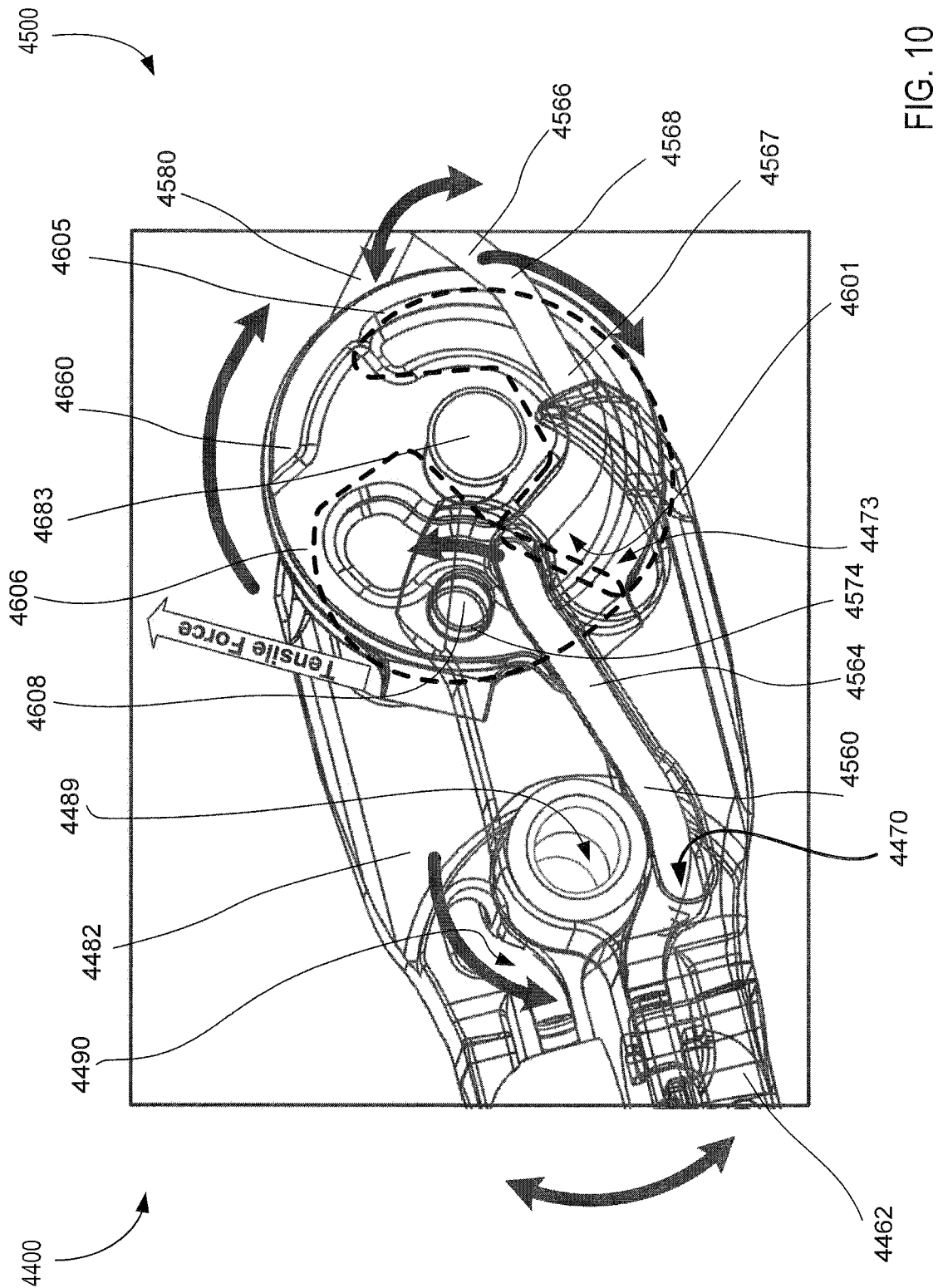
FIG. 10 is an enlarged side view of a portion of the distal end portion indicated by the region K shown in FIG. 8, shown with a first link removed and a first tool member transparent to expose routing of a first non-drive wire.

Referring to FIGS. 8-10, a guide path 4456, 4496 is defined through the instrument 4400 for each of the non-drive wires 4560, 4580 to guide the wires along a desired route through within the instrument. Each wire extends distally along the corresponding guide path from its proximal end portion 4561, 4581 coupled to the energy source (not shown) to the distal end portion 4562, 4582 coupled to a corresponding contact portion 4463, 4483. A first guide path 4456 for the first non-drive wire 4560 and a second guide path 4496 for the second non-drive wire 4580 are each defined in the instrument 4400 including within the wrist mechanism 4500 and the end effector 4460. Each of the guide paths 4456, 4496 guide the corresponding non-drive wire 4560, 4580 to extend through the instrument 4400 along the designated route, which helps avoid interfering contact between the non-drive wires 4560, 4560 and components of the instrument 4400 during articulation movements of the instrument.

Each of the guide paths 4456, 4496 includes smaller guide pathways that together form the route provided by the guide paths 4456, 4496. For example, a first and second guide pathway 4535, 4536 are defined through the first link 4510 of the wrist mechanism 4500 for each of the non-drive wires 4560, 4580. The proximal end portions 4561, 4581 of the non-drive wires extend distally along a corresponding one of the guide paths 4456, 4496 from being coupled to an energy source (not shown) at their proximal end, along one or more pathways defined in the shaft 4410, to the pathways 4535, 4536 defined through the first link 4510 of the wrist mechanism 4500. The guide paths 4456, 4496 continue to guide the non-drive wires from within the first link into through similar corresponding pathways 4635, 4636 defined in the second link 4610 that guide each of the non-drive wires 4560, 4580 to the corresponding one of the pulleys 4660, 4665 that function as transfer members. The guide paths 4456, 4496 further include guide pathways 4470, 4490 defined within the tool members 4462, 4482, which guide the non-drive wires 4560, 4580 along the guide paths 4456, 4496 from each of the corresponding pulleys 4660, 4665, through the openings 4473, 4493, and into the corresponding guide pathway 4470, 4490 defined within the tool members 4462, 4482. The tool member guide pathways guide the non-drive wires 4560, 4580 within the corresponding tool member to the contact portion 4463, 4483 located a distal end portion of each tool member. Each of the non-drive wires are coupled to a corresponding one of the contact portions at their distal end portions, which completes their route within and through the instrument along the guide paths 4456, 4496.

Referring to FIGS. 9 and 10, the central portions 4564, 4584 of each of the non-drive wires 4560, 4580 are routed through the first and second pulleys 4660, 4665 according to the transfer member functionality provided by the pulleys, such that the non-drive wires 4560, 4580 avoid making interfering contact with any of the components during articulation movements. Further, as discussed below along with FIGS. 10, 11A and 11B, the transfer member functions provided by the first and second pulleys 4660, 4665 provide flexibility during articulation movements to the non-drive wires 4560, 4580, so that the non-drive wires do not limit the range of articulation movements that the instrument 4400 can perform. In particular, each of the pulleys 4660, 4665 are configured to effectively guide the central portions of the non-drive wires through the force transmission linkages discussed below along with FIG. 10 with respect to force amplification mechanisms of the instrument, which can provide clamping forces or other applied forces to the tool members 4462, 4482 while also performing transfer member functions for the non-drive wires.

Referring to FIG. 10, an example force amplification arrangement is shown for the instrument 4400, which can be used with other articulable instruments along with providing similar transfer member functions. The force amplification arrangement between the components shown in FIG. 10 operate to provide high forces at the contact portions 4463, 4483 of the tool members without increasing the driving force transmitted to the instrument 4400 and without increasing the size or envelope (e.g., the overall diameter) of the instrument wrist assembly 4500. It is understood that the example force amplification mechanisms described herein along with FIG. 10 are provided for illustration purposes along with describing advantageous aspects and features pertaining to the transfer member functions of the pulleys 4660, 4665 and the non-drive wires 4560, 4580 routed therein. As such, it is understood that many different drive mechanisms and other force transmission options can be used with the instrument 4400.

The example force amplification mechanism shown in FIG. 10 includes multiple tension members (not shown) including at least one tension member (not shown) that is coupled at a distal end portion thereof to pulley 4660. For instance, the tension member coupled to the pulley 4660 can be located within an outer groove 4661 defined in a perimeter portion of the pulley 4660, which is configured to apply a tensile force to the rotatable pulley 4660 to rotate the pulley. In a direct force transmission mechanism (non force amplification mechanism), the pulley 4660 can be directly connected to the corresponding articulable tool member 4462 such that the tool member rotates along with the pulley about a rotation axis 4683 of the pulley. As such, the tensile force applied by the tension member (not shown) to a perimeter portion of the pulley 4660 in such a direct rotation arrangement provides a torque about the rotary axis of the pulley 4660. The torque applied to the pulley urges the pulley to rotate about its axis, as well as the tool member to likewise rotate about the same axis.

The applied force transmitted to the contact portion 4463 of the tool member would be a function of the tensile force transmitted by the tension member to the pulley in accordance with a ratio of the radial distance from the rotary axis 4683 of the pulley at which the tension member transmitted the tensile force to the perimeter portion of the pulley (i.e. the moment arm of the tensile force applied to rotate the pulley) vs. the rotation distance that the contact portion 4463 extends from the same rotary axis (i.e., the moment arm of the contact portion along the tool member). In order to increase the force applied to the tool member at the contact portion as a result of the tensile force applied to the pulley by the tension member (not shown) in such a direct transmission arrangement (not shown). Alternatively, the tensile force transmitted to the pulley by the tension member could also be increased. In addition, the size (radius) of the pulley could also be increased to provide a longer moment arm at the pulley and thus a larger applied drive torque at the pulley. Further, the length (moment arm) of the tool member could be decreased to thereby increase the driven force provided at the contact portion of the tool member from the rotational drive torque transmitted to the pulley about its rotary axis. However, it can be desirable to avoid increasing the amount of tensile force transmitted by the tension member (not shown) along with avoiding increasing the radial size of the pulley 4660 in order to provide a higher force at the contact portion 4463 of the tool member 4462. It can further be desirable to avoid decreasing the length of the tool member to reduce the radial distance of the contact portion from the rotary axis.

Thus, the force amplification arrangement shown in FIG. 10 can operate to transmit higher forces at the contact portion 4463 of the tool member 4462 without increasing the radius of the pulley 4660, the tensile force transmitted to the pulley by the tension member (not shown), and/or the envelope (overall diameter) of the instrument 4400. Further, such higher forces can likewise be provided by the force amplification arrangement of FIG. 10 without decreasing the overall length of the tool member that extends distally from the wrist assembly or the relative distal location of the contact portion 4463. Rather, the force amplification arrangement shown in FIG. 10 increases the force applied to the tool member 4462 by separating the pivot about which the pulley 4660 rotates from the pivot about which the tool member 4462 rotates. In particular, the pivot openings 4469, 4489 and the pivot pin 4472 about which the tool members rotates is offset distally along the instrument 4400 from the pulley pivot. As such, a force transmitting pin 4494 within the opening 4608 couples the pulley 4660 to the tool member 4462 at a position behind the pivot 4489 of the tool member and at a greater distance (i.e., moment arm) from the tool member pivot compared with the radial distance from the pulley pivot 4683.

Thus, the moment arm for the drive torque that is applied to the tool member 4462 is greater in the force amplification arrangement shown in FIG. 10 (i.e., the drive torque is increased for the same tensile force transmitted by the tension member) than the drive torque that would be provided by the same tensile force applied to the pulley in a direct rotary force transmission mechanism. Further, the moment arm for the tool member 4462 is decreased for the force amplification arrangement shown in FIG. 10. As such, even if the drive torque was not increased due to the offset of the tool member pivot from the pulley pivot, the driven force transmitted to the end of the tool member is increased based on the decreased distance from the tool member to its pivot point (i.e., the reduced moment arm for the driven/received torque at the tool member).

Despite such force amplification benefits being provided to the tool member 4462 by the force amplification arrangement shown in FIG. 10, such an arrangement can increase challenges for avoiding interference between components during articulation movements if the overall diameter of the instrument is not increased. In addition, such an arrangement increases the number of movable components within the instrument, which further reduces available space within the instrument for routing additional components, such as non-drive wires. Further, the force amplification arrangement increases the complexity of articulation movements due to a reverse torque arrangement that rotates the pulley 4660 in an opposite rotation direction than the tool member when a tensile force is applied to the pulley, as well as due to additional linkage provided by coupling the pulley 4660 to the tool member 4462. Thus, the force amplification arrangement shown in FIG. 10 reduces available space for routing a non-drive member therein, increases the likelihood of any excess slack in the non-drive member interfering or being caught by the articulation linkages and components, and eliminates portions of space within the instrument in which slack or flexible portions of the non-drive wire could be located to avoid limiting articulation movements. Further, the additional linkages in the force amplification arrangement shown in FIG. 10 can increase the amount of flexibility needed for routing a non-drive wire through the instrument.

Referring to FIGS. 10, 11A and 11B, the first and second pulleys 4660, 4665 are shown that function as transfer members that provide efficient, tightly controlled routing of the non-drive wires 4560, 4580 within the instrument 4400 and through the force amplification mechanism such that the non-drive wires avoid contact with the movable linkages and components during articulation movements, while also providing appropriate flexibility for the non-drive wires 4560, 4580 to avoid limiting the articulation movements. As such, the cavity 4601 is defined within an outer portion of each of the tensile force drive pulleys 4660, 4665, which closely guides the route of the non-drive wires 4560, 4580 proximate the force amplification linkages for the tool members 4462, 4482. It further provides flexibility for the non-drive wires 4560, 4580 during articulation movements including movements for the force amplification components and linkages. The description for each of the pulleys 4660, 4665 applies to both of the pulleys 4660 and 4665, but in a mirror image arrangement. As such, only one pulley 4660 will be described in detail herein. However, the description applies to both pulleys 4660, 4665.

As shown in FIGS. 11A and 11B, an outer side of the pulleys 4660 defines a cavity 4601 therein. The cavity can extend around the pivot 4669 about which the pulley 4660 rotates without encompassing or including the pivot 4669, which is shown in FIGS. 11A and 11B as an opening for a pivot pin. Thus, for instrument 4400, the cavity 4601 can be defined as a cavity within the pulley that extends around a portion of a perimeter region of the pulley without fully extending around the pivot 4669. Stated differently, the cavity 4601 is defined within the pulley 4660 about the pivot 4669 extending less than 360 degrees around the pivot 4669. The cavity includes a deep guide portion 4606 and a shallow wire entry sector 4605, which can partially overlap as shown in FIGS. 11A and 11B. The deep guide portion 4606 is defined between a pair of high walls 4602, which can extend the full thickness of the pulley 4660. Although the pair of high walls can be described as being high and the corresponding guide portion 4606 can be described as being deep, it is understood that the pulley 4660 can be oriented in a lateral position such that the cavity 4601 and deep guide portion 4606 can be defined within lateral portions of the pulley as arranged within the instrument 4400.

As illustrated in FIGS. 10, 11A and 11B, the deep guide portion 4606 of the pulley 4660 extends around a portion of the pulley along which a proximal end of the guide path 4470 that is defined within the tool member 4462 moves with respect to the pulley 4660 for the range of articulation movements between the pulley 4660 and the tool member 4462. Stated differently, the deep guide portion 4606 outlines a range of positions for the entrance portion of the tool member guide path 4470 that receives the non-drive wire 4560 as it exits the cavity 4601 of the pulley 4660 along its distal route extending from the pulley 4660 to the contact portion 4463 of the tool member 4462. As such, a pair of walls having a height H2 as shown in FIGS. 11A and 11B extend around the deep guide portion 4606 including a tall outer perimeter wall 4602 that forms a boundary along with the inner wall for the non-drive wire 4560, which maintains the non-drive wire 4560 within the deep guide portion 4606 except for guiding the non-drive wire to continue along its route within the guide path 4456. Thus, the deep guide portion 4606 guides the non-drive wire 4560 to stay within the portion of the cavity within the deep guide portion other than to follow the route of its guide path and extend into the guide path 4470 defined within the tool member. The remainder of the cavity 4601 is outlined along the outer perimeter portion of the pulley 4660 by a comparatively short outer wall 4604 having a shorter height, $H_1$, which forms a low, outer perimeter boundary along a portion of the cavity 4601. In contrast with the outer wall of the deep guide portion 4606, the short outer wall 4604 has a height, $H_1$, that is less than the thickness of the pulley 4660.

The short outer wall 4604 outlines a wire entry sector 4605 of the pulley, which operates to provide additional flexibility for the non-drive wires as needed during articulation movements. Referring to FIG. 10, an enlarged view of the region "K" indicated in FIG. 8 is shown for the instrument 4400 in a first orientation, in which the end effector 4462 is a non-rotated orientation and the tool members 4462 and 4482 are in a closed position. The highlighted non-drive wires 4560 and 4580 shown in FIG. 8 for discussion purposes are not reproduced in the enlarged view of region K shown in FIG. 10. Further, the second link 4610 has been removed to expose the pulley 4660 and the path of the central portion 4564 of the non-drive wire 4560 extending through guide path portions of the pulley 4660 as part of the transfer member functionality provided by the pulley. As such, the cavity 4601 formed within the pulley is shown, as well as a transition portion 4567 of the non-drive wire 4560 that is located within the cavity 4601.

When in the non-rotated first orientation of FIGS. 8 and 10, in which the end effector 4460 is oriented in a straight orientation in alignment with the second link 4610, and further when the tool members 4462 and 4482 are in a closed position, the transition portion 4567 is in a first compact configuration within the cavity 4601. Further, the transition portion 4567 includes at least one bend 4568 while in the first compact configuration and includes a feed portion 4566 of the non-drive wire that is located outside of the cavity 4601. Similar in many respect to the instrument 3400 described above, the pulley 4660 is rotatable relative to the first and second link members 4510 and 4610 between a first orientation shown in FIGS. 8 and 10 and a second orientation in which the first tool member 4462 is rotatable in a yaw direction with respect to the first and second link members, as well as rotatable in a jaw opening direction that likewise rotates each of the tool members with respect to the first and second link. In addition, the pulley is configured to be coupled to at least one tension member (not shown) that can be located within an outer groove of the pulley and coupled to the pulley such that, when the tension member (not shown) is moved, the first tool member 4462 is rotated with respect to the first link member 4510 and/or the second link member 4610.

For example, the tension member (not shown) can be coupled to the pulley 4660 in a force amplification arrangement in which the tension member is located within an outer groove of the pulley and connected to a perimeter portion of the pulley to apply a tensile force to the perimeter portion of the pulley. In accordance with force amplification arrangement described above, when the tension member (not shown) is moved away from the pulley, it applies a tensile force to the pulley 4660 at its perimeter portion that imparts a torque to the pulley that rotates the pulley in the clockwise direction shown in FIG. 10. In accordance with operation of the force amplification arrangement, rotation of the pulley 4660 in the clockwise direction due to movement of the tension member causes the first tool member 4462 to rotate in a counterclockwise direction about the distally offset pivot 4489 of the end effector 4460.

As such, the first tool member 4462 rotates from the non-rotated, closed end effector, first orientation of FIG. 8 to an open end effector orientation in which the tool member 4462 is rotated with respect to the first link 4510 and the second link 4610. When the pulley rotates clockwise from the first orientation shown in FIGS. 8 and 10 responsive to movement of the tension member (not shown) that is coupled to a perimeter portion of the pulley, the feed portion 4566 rotates from a position outside of the cavity 4601 to a position within the cavity due to the shallow wire entry sector 4605 of the pulley 4660, which permits flexible rotational movement of the transition portion 4567 into and out of the cavity 4601 along the span of the wire entry second 4605. Further, the deep guide portion 4606 of the pulley tightly controls the route of the non-drive wire 4560 including path of the non-drive wire 4560 extending from the pulley to the guide path 4470 defined within the tool member 4462. As such, the pulley 4660 of the instrument 4400 operates as a transfer member to tightly control the route of the non-drive wire 4560 proximate articulable components and linkages of the instrument for rotational movements of the tool member 4462 including yaw rotations and opening and closing clamp rotations.

Thus, the instrument 4400 provides transfer member functionality that tightly controls the route of the non-drive wires 4560, 4580 at locations close to articulable components of the instrument, as well as provides flexible for the non-drive wires as needed during articulation movements. Further, the instrument 4400 provides such transfer member functionality via the configuration of the pulleys 4660, 4665, and does so for along with a force amplification mechanism. In addition, the instrument 4400 provides such transfer member functions in a different manner from the operations of the transfer member described above along with instruments 2400 and 3400. Also, the instrument 4400 provides such transfer member functions including moving a feed portion of the non-drive wire into the cavity in a passive manner without needing to push or urge the non-drive wire to move, such as based on movement of the non-drive wire based on movement of a tension member as described in instrument 3400. Moreover, the instrument 4400 provides transfer member functions without biasing the transition portion toward a compact, unextended configuration or imparting curvilinear shapes in the transition portion of the non-drive wire.

Referring to FIGS. 12A, 12B and 13, the second tool member 4482 and the end effector 4460 of the instrument 4400 are shown in greater detail and with greater contrast between portions of the tool members to more clearly show the configuration of the tool members 4462 and 4482 including the guide paths 4470, 4490 defined therein for the non-drive wires 4560 and 4580, as well as the route of the non-drive wires within the guide paths formed therein. Although FIGS. 12B and 13 only show the second tool member 4482, the first tool member 4462 is configured in a similar mirror-image arrangement with respect to the second tool member. In addition, FIGS. 12A, 12B and 13 more clearly shows an electrically insulated arrangement of the tool member 4462, 4482 to electrically isolate each of the contact portions 4463, 4483 from other portions of the instrument. Electrically isolating each of the contact portions can be desirable for instruments including those described herein, in which non-drive wires 4560, 4580 are routed therein to be electrically coupled to the contact portions 4463, 4483 of each of the tool members 4462, 4482 at a distal end portion of the non-drive wire that is coupled at its opposite end to an energy source (not shown). In particular, as best shown in FIG. 13, tool members 4462 and 4482 include an electrical insulator 4486 disposed between an electrically conductive distal contact portion 4463, 4483 that is coupled to the non-drive wire 4560, 4580 and a proximal base portion 4467, 4487 that can be formed from as a rigid support structure that can formed from an electrically conductive structural material, such as a surgical grade stainless steel material. medical grade steel material. As shown in FIG. 13, a spacer 4471 that fits within the opening 4485 or other retention member can be used to electrically couple the distal end portion of the non-drive wire 4560, 4580 to the contact portion of 4463, 4483 of the tool member.

Referring now to FIGS. 14, 15, 16A and 16B, an instrument 5400 is shown, which is similar to instrument 4400 described above and that generally includes the same preferences and features as described above along with instrument 4400 except as described hereafter. Accordingly, like numbers refer to like features described above. As with instrument 4400, instrument 5400 also includes a wrist assembly 5500 having a proximal first link 5510 and a distal second link 5610. The proximal first link 5510 has a proximal end portion 5511 and a distal end portion 5512. The distal second link 5610 has a proximal end portion 5611 and a distal end portion 5612. The wrist assembly 5500 includes a force amplification mechanism for providing high force movements to the pair of tool member 5462, 5482 along with routing a non-drive wire within the instrument that is coupled to an energy source at a proximal end portion and is electrically coupled to a contact portion 5463, 5483 of the tool member at its distal end portion. In addition, instrument 5400 includes at least one tension member (not shown), and is configured for controlled movement in response to movements by one or more tension members (not shown) that are controlled by the surgical system.

Instrument 5400 differs from instrument 4400 based primarily on the use of a different option for the pulleys 5660, 5680 that also provide transfer member functionality, as well as including a correspondingly different configuration for the transition portion of the non-drive wires 5560, 5580 in accordance with the different configuration of the pulleys 5660, 5680. In particular, an outer side of the pulleys 5660, 5680 defines a cavity 5601 therein that extends completely around the pivot 5669 about which the pulley 5660 rotates, which encompasses the pivot 5669 by defining the cavity 5601 as a circular path formed in the pulley 5660 that surround the pulley pivot. Thus, for instrument 5400, the cavity 5601 can be defined as a cavity within the pulley that extends around a perimeter region of the pulley including fully extending around the pivot 5669. Stated differently, the cavity 5601 is defined within the pulley 5660 about the pivot 5669 and extending 360 degrees around the pivot 5669.

Similar to pulley 4660, the pulley 5660 also includes an outer groove 5661 (within which the tension member can be attached), a pin opening 5608 (to couple the pulley 5660 to the tool member 5462, a deep guide portion 5606 and a shallow wire entry sector 5605. The deep guide portion 5606 and the shallow wire entry sector 5605 can partially overlap as shown in FIGS. 16A and 16B. The deep guide portion 5606 is defined between a pair of high walls 5602, which can extend the full thickness of the pulley 5660. Although the pair of high walls can be described as being high and the corresponding guide portion 5606 can be described as being deep, it is understood that the pulley 5660 can be oriented in a lateral position such that the cavity 5601 and deep guide portion 5606 can be defined within lateral portions of the pulley as arranged within the instrument 5400.

Similar to instrument 4400, the deep guide portion 5606 of each pulley corresponds with the range of positions for the proximal end portion of the guide paths 5470, 5490 defined within the tool members 5462, 5482 into which the non-drive wire 5560 extends distally along the guide path moving from the pulley 5660 along the tool member guide path 5470. As such, a pair of tall walls having a height H2 as shown in FIGS. 16A-16C extend around the deep guide portion 5606 including a tall outer perimeter wall 5602 that forms a boundary along with the inner wall for the non-drive wire 5560, which maintains the non-drive wire 5560 within the deep guide portion 5606 except for guiding the non-drive wire to continue along its route within the guide path to extend from the pulley cavity through the opening 5473 and into the tool member guide path 5470. Similar to instrument 4400, the remainder of the cavity 5601 is outlined along the outer perimeter portion of the pulley 5660 by a comparatively short outer wall 5604 having a shorter height, $H_1$, which forms a low, outer perimeter boundary along a portion of the cavity 5601. In contrast with the outer wall of the deep guide portion 5606, the short outer wall 5604 has a height, $H_1$, that is less than the thickness of the pulley 5660.

Figure 15:
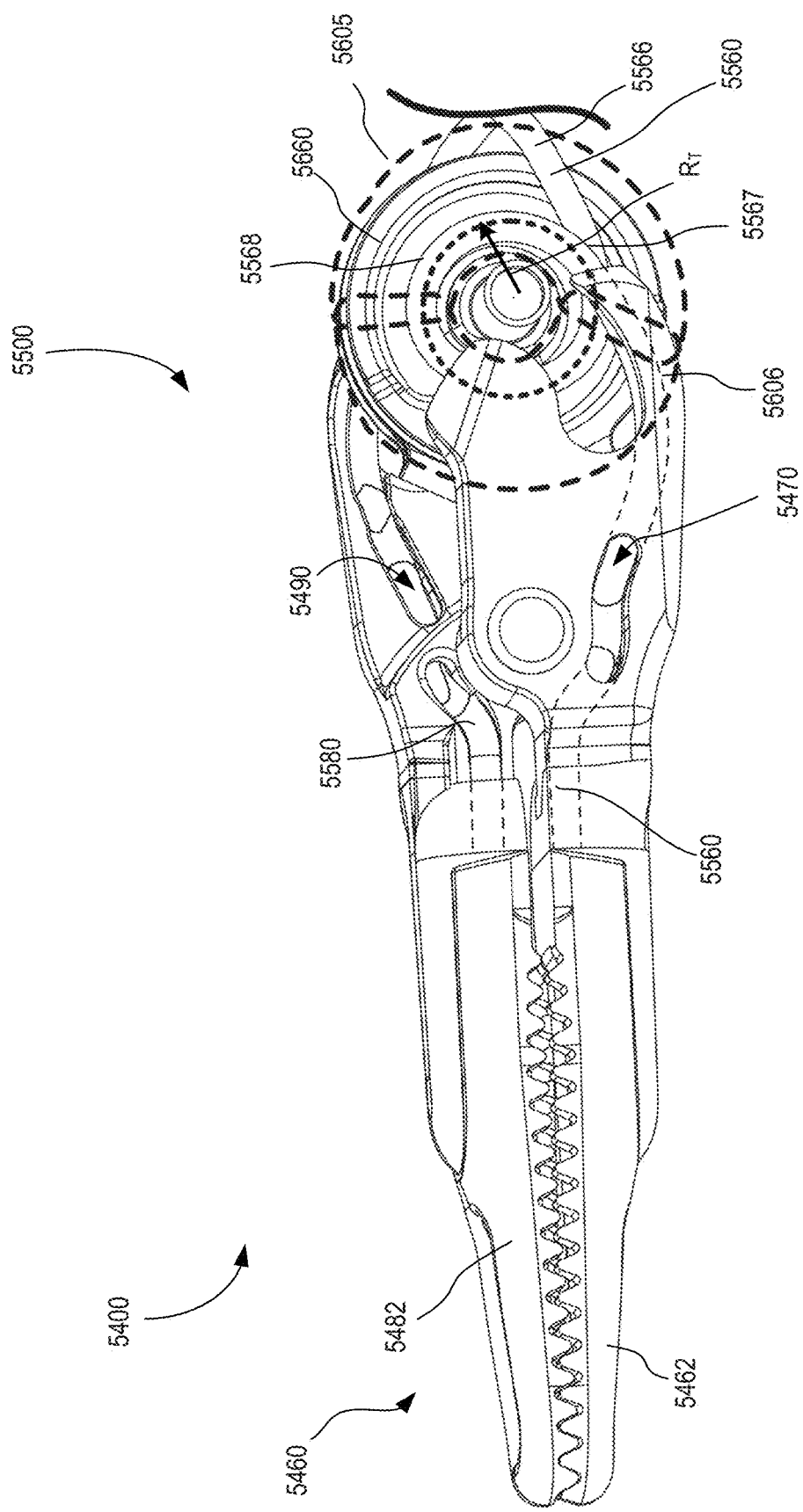
FIG. 15 is an enlarged side view of the distal end portion of the instrument of FIG. 14 shown with the first link removed and the first tool member transparent to expose routing of the first non-drive wire.

Also similar to instrument 4400, the short outer wall 5604 outlines a wire entry sector 5605 of the pulley, which operates to provide additional flexibility for the non-drive wires as needed during articulation movements. Referring to FIG. 15, the wrist assembly 5500 of the instrument 5400 is shown with the second link 5610 removed and the tool member 5462 partially transparent to expose the cavity 5601 defined in the pulley 5660, the path of the central portion 5564 of the non-drive wire 5560 that extends through guide path portions of the pulley 5660 as part of the transfer member functionality provided by the pulley. As such, the cavity 5601 formed within the pulley is shown, as well as a transition portion 5567 of the non-drive wire 5560 that is located within the cavity 5601.

Figure 14:
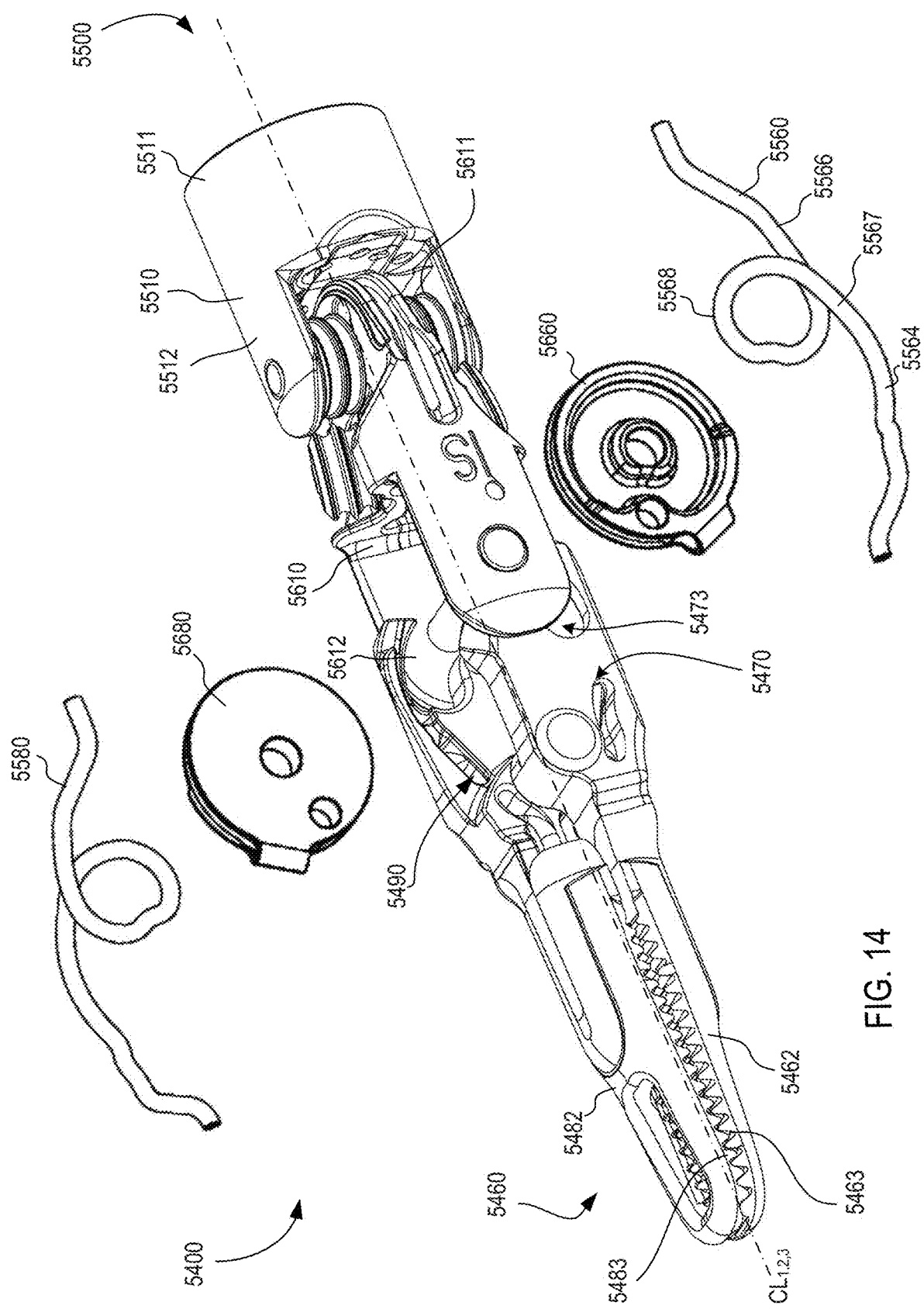
FIG. 14 is an enlarged perspective view of a distal end portion of an instrument in a first orientation, according to an embodiment, shown in a partially exploded view.

When in the non-rotated first orientation of FIGS. 14 and 15, in which the end effector 5460 is oriented in a straight orientation in alignment with the second link 5610, and further when the tool members 5462 and 5482 are in a closed position, the transition portion 5567 is in a first compact configuration within the cavity 5601. Further, the transition portion 5567 likewise includes a feed portion 5566 of the non-drive wire that is located outside of the cavity 5601 while in the first orientation shown in FIGS. 14 and 15 and is configured to move into the cavity 5601 when the tool member 5462 rotates to a second orientation. However, as opposed to the instrument 4400, the transition portion 5567 includes a curvilinear shape in the form of a loop 5568 that extends around the pivot of the pulley within the cavity 5601. As the cavity 5601 formed completely around a pivot of the pulley 5660 allow the transition portion 5567 to be formed into one or more curvilinear paths that can provide greater flexibility for the non-drive wire 5560 during articulation movements compared with the cavity 4601 formed in the pulleys of instrument 4400.

In addition, defining the cavity 5601 as a 360 degree path within the pulley 5660 can permit the transition portion to be formed into a loop around the pulley pivot, which can provide a high degree of flexibility to the non-drive wire 5560 including both expanding and contracting compared with the default radius of the loop when the instrument is in the first orientation. In addition, defining the cavity within the pulley as shown for cavity 5601 can also allow for a wire entry sector 5605 to be formed along one or more sectors of the cavity 5601 based on forming the outer wall 5602 of the cavity to have a shorter height $H_1$ in comparison with the outer wall height H2 forming the outer boundary along the deep guide portion 5606 of the cavity. As such, a feed portion 5566 of the non-drive wire 5560 that is located outside of the cavity 5601 when in the first orientation shown in FIGS. 14 and 15 can enter flexibly enter the cavity 5601 as needed via the wire entry sector 5605 when the first tool member 5462 rotates to another orientation. Thus, instrument 5400 can provide flexibility for the non-drive wire 5560 based on the loop arrangement of the transition portion along with tightly controlling the routing of the non-drive wire proximate articulation components, such as the transition from the cavity 5601 to the guide path 5470 defined in the first tool member 5462. In addition, instrument can also take advantage of the passive feed portion functionality described above along with instrument 4400 due to the option for including a wire entry sector along portions of the cavity that can be more flexibly controlled.

Referring now to FIGS. 17-22, an instrument 6400 is shown that combines many of the desirable features described above for other instruments described herein, such as most of the benefits described along with instrument 5400 that can be provided via a loop-type transition portion, as well as benefits of the wire feed functionality that can provide greater flexibility for the non-drive wire and the tight routing controls for the non-drive wire. Instrument 6400 provides a transfer member arrangement that maintains these desirable aspects features described above along with instrument 5400 and further adds an active feed portion feature based on movement of a tension member as described above along with instrument 3400. Thus, instrument 6400 includes the same aspects and features described above along with instruments 4400 and 5400 except as described hereafter. Accordingly, like numbers refer to like features described above.

As with instrument 4400 and 5400, instrument 6400 also includes a wrist assembly 6500 having a proximal first link 6510 and a distal second link 6610. The proximal first link 6510 has a proximal end portion 6511 and a distal end portion 6512. The distal second link 6610 has a proximal end portion 6611 and a distal end portion 6612. The wrist assembly 6500 includes a force amplification mechanism for providing high force movements to the pair of tool members 6462, 6482 along with routing a pair of non-drive wires 6560, 6580 within the instrument. The non-drive wires 6560, 6580 are coupled to an energy source at a proximal end portion 6561, 6581 and is electrically coupled to a contact portion 6463, 6483 of the tool member at a distal end portion 6562, 6582. In addition, instrument 6400 includes at least one tension member (not shown), and is configured for controlled movement in response to movements by one or more tension members (not shown) that are controlled by the surgical system.

Referring to FIGS. 18A-18C, instrument 6400 includes an extended pulley arrangement for the pulleys 6660, 6680 that each extend laterally outward to form the inner guide surface to support and guide the transition portion of 6567 along a curvilinear path along the inner guide surface 6691. In addition, the inner guide surface 6691 is configured to form an external groove along the inner guide surface 6691 that also defines a cavity 6601 around the inner guide surface 6691 at an outer lateral side of the pulley 6660 within which the transition portion 6567 is located. The pulley 6660 also includes an outer groove 6661 (within which the tension member can be attached), a pin opening 6608 (to couple the pulley 6660 to the tool member 6462) and a pivot opening 6669.

Instrument 6400 differs from instrument 5400 based primarily on the use of an inner guide surface 6691 in the form of a groove 6691 on the outer perimeter of a sectored pulley portion 6690 that guides the transition portion 6567 of the non-drive wire 6560 during rotations of the end effector 6460 from the first orientation, and also based on the addition of a guide pin 6692 that guides the non-drive wire 6560 into the guide path 6470 of the tool member 6462 during opening and closing articulation movements of the end effector. Descriptions for one side of the instrument 6400 apply to both sides of the instrument for corresponding components, such as for the tool members, the non-drive wires and the pulleys that also function as transfer members.

Figure 19A:
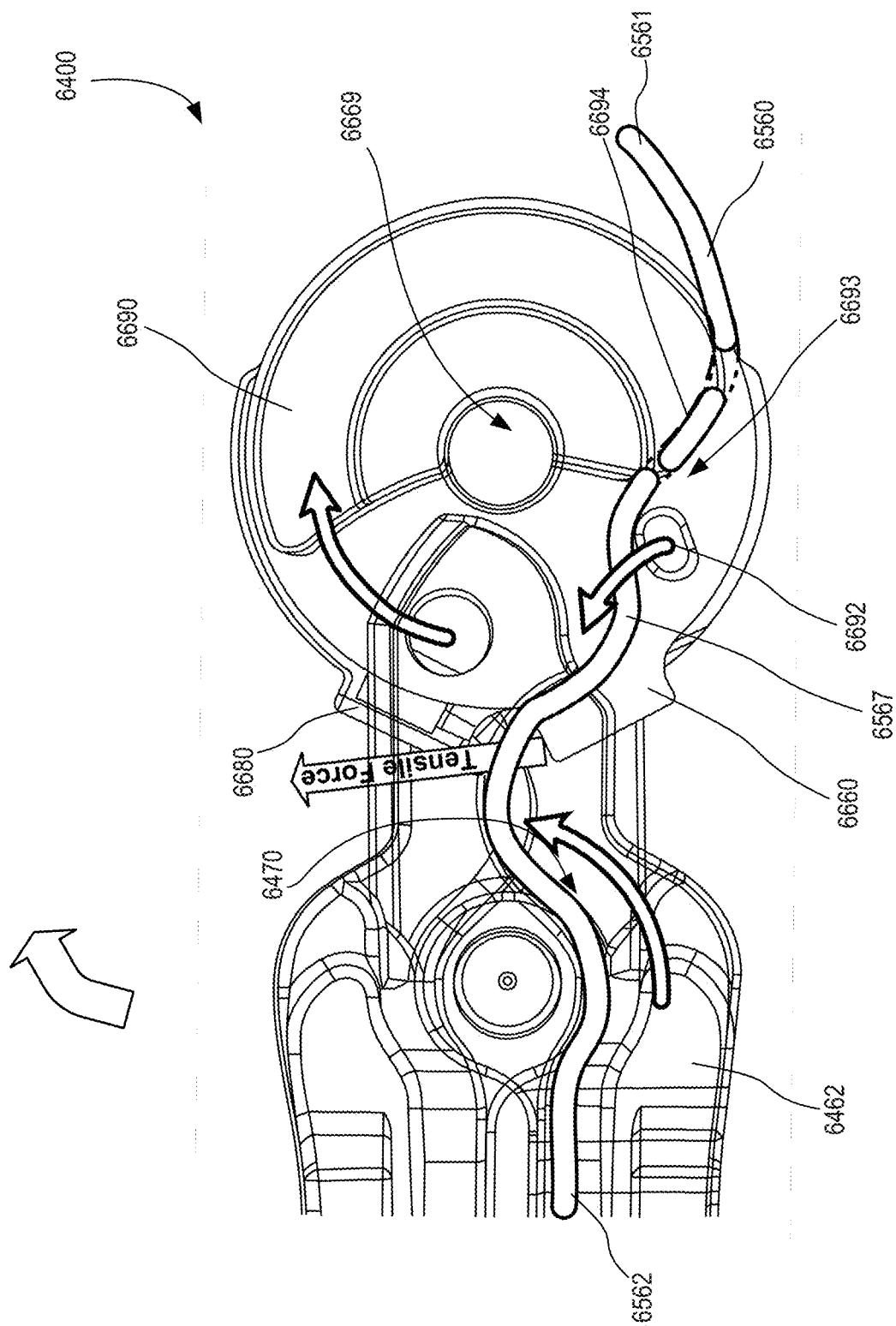
FIG. 19A is an enlarged side view of a portion of the distal end portion indicated by the region L shown in FIG. 17 in the first orientation, shown with a first link removed and a first tool member transparent to expose routing of a first non-drive wire.
Figure 19B:
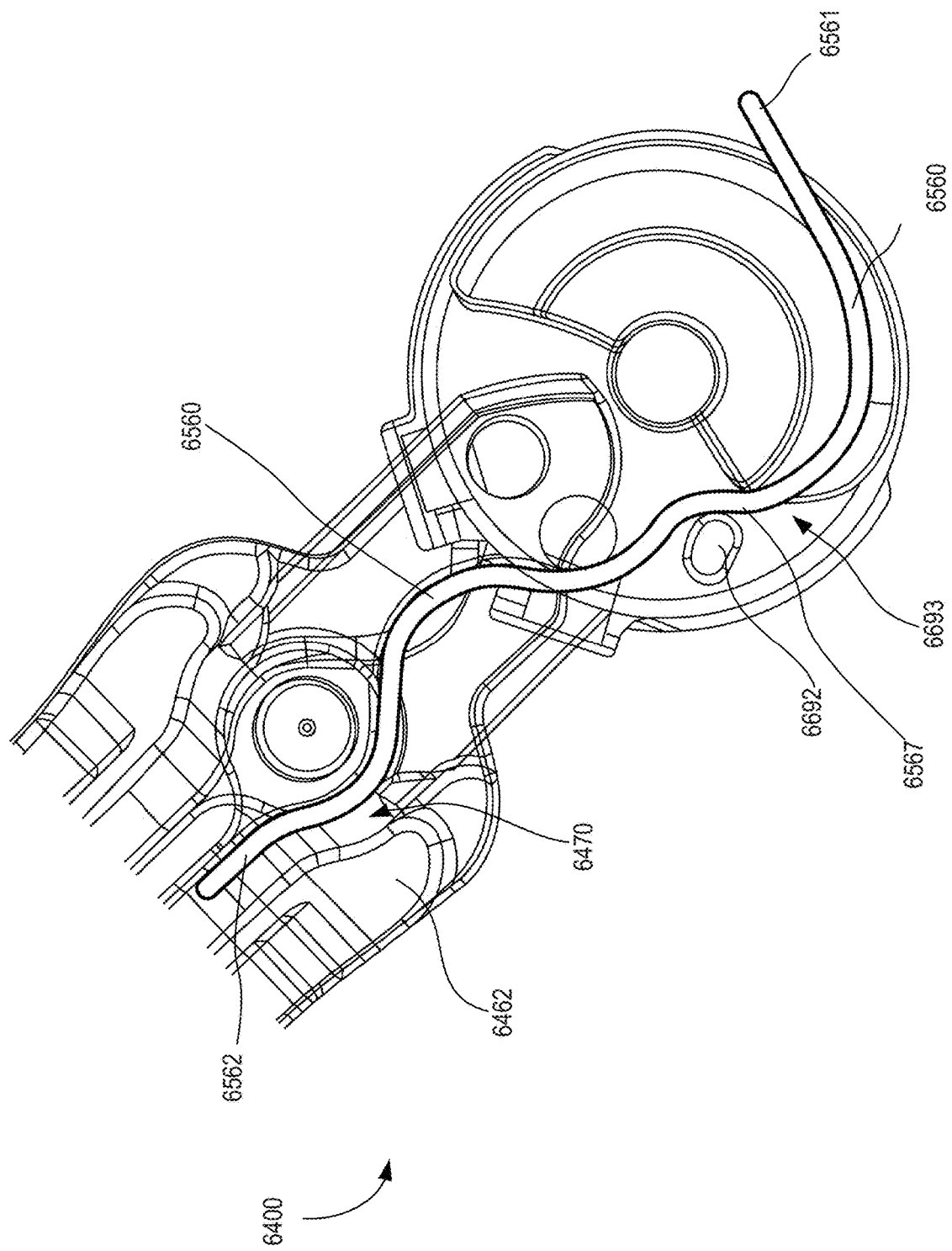
FIG. 19B is an enlarged side view of a portion of the distal end portion indicated by the region L shown in FIG. 17, in a second orientation, shown with the first link removed and the first tool member transparent to expose routing of the first non-drive wire.

With respect to the inner guide surface 6691, each of the pulleys 6660, 6680 that provides transfer member functionality is configured to define the cavity 6601 at an outer side portion of the pulleys that extends around the inner guide surface 6691 in the form of a groove 6691 that can take up and release the corresponding non-drive wire 6560, 6580 during rotations as is shown in FIGS. 19A and 19B. The instrument 6400 is shown while in the non-rotated first orientation in FIG. 19A, and in a rotated second orientation in FIG. 19B in which the end effector 6460 has been rotated in a clockwise direction with respect to the first link 6510. As can be seen in FIG. 19B, a greater length of the non-drive wire 6560 is guided around the inner guide surface 6691 when the instrument 6400 is in the rotated second orientation. An inward curve 6694 is formed at an exit portion of the inner guide surface 6691 that defines a groove guide path 6693 between the inner guide surface and the guide pin 6692.

The groove guide path 6693 and the guide pin 6692 together guide the transition portion 6567 of the non-drive wire 6560 to move into the guide path 6470 of the tool member 6462 during opening articulation movements. Referring to FIG. 19A, in order to open the tool members 6462, 6482, a tensile force can be applied to the first pulley 6660 in the direction shown to impart a clockwise rotation to the first pulley, and a reverse tensile force (not shown) can be applied to the second pulley 6680 at the same time to impart counterclockwise rotation to the second pulley. During such opening articulation movements, the guide pin 6692 urges the non-drive wire of the transition portion 6587 that is located in the groove guide path 6693 to move into the guide path 6470 of the tool member 6462 by pushing a length of the non-drive wire into the guide path of the tool member. As such, the instrument 6400 is configured to actively urge the non-drive wires to move as needed from the pulleys 6660, 6680 that also function as transfer members into the guide paths 6470, 6490 of the tool members during opening articulation movements.

Figure 20C:
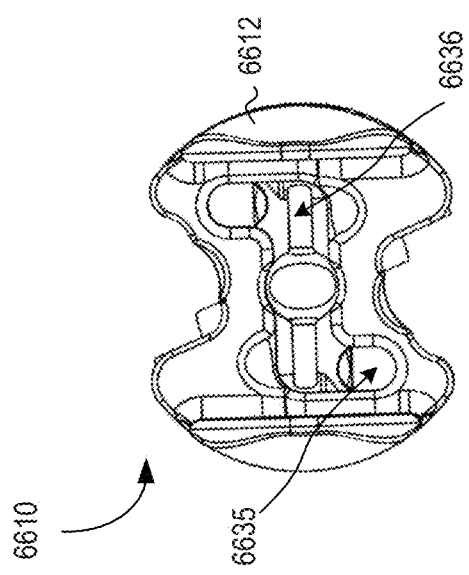
FIG. 20C is a top view of the second link of FIG. 20A.
Figure 20B:
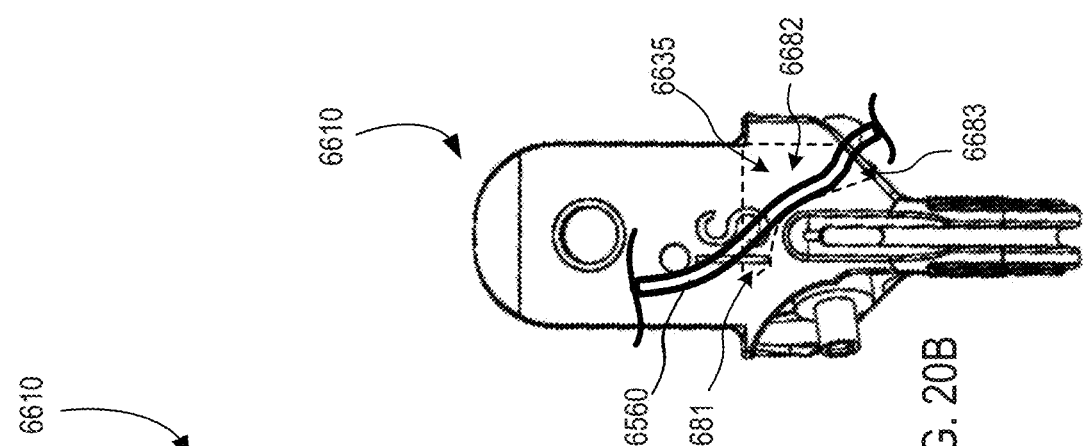
FIG. 20B is a side view of the second link of FIG. 20A.
Figure 20A:
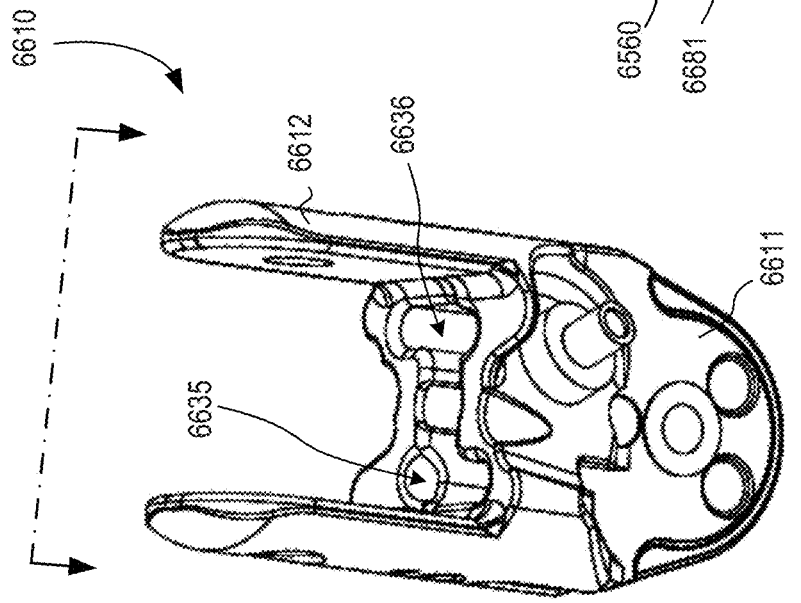
FIG. 20A is a perspective view of the second link of the instrument of FIG. 17.

Further, instrument 6400 is also configured to provide an active, tension member-driven feed functionality that is similar to what is described along with instrument 3400 rather than including a passive feed portion function as described above along with instrument 5400. Referring to FIGS. 20A-20C, 21 and 22, aspects and features of the instrument 6400 are shown for moving a feed portion of the non-drive wire into the cavity when a tension member is moved to impart rotation of the tool member 6462. As shown in FIGS. 20A-20C, the second link defines curved guide paths therein at the distal end portion of the second link 6610, which guides the non-drive wire 6560, 6580 to change its route from a first lateral side of the second link 6610 to the opposite second lateral side of the second link. As shown in FIG. 20B, the guide pathway 6635 defined in the second link includes a first guide portion 6683 at a proximal end of the guide pathway 6635, a second guide portion 6681 at a distal end of the guide pathway, and a curved central portion 6682 between the first and second guide portions. The curved central portion 6682 guides the non-drive wire 6560 extending therethrough to change its route from a first lateral side of the second link to an opposite second lateral side of the second link. The guide pathway 6636 that corresponds to the second non-drive wire 6580 is similarly configured to change the route of the non-drive wire from one lateral side of the instrument to the other.

Figure 21:
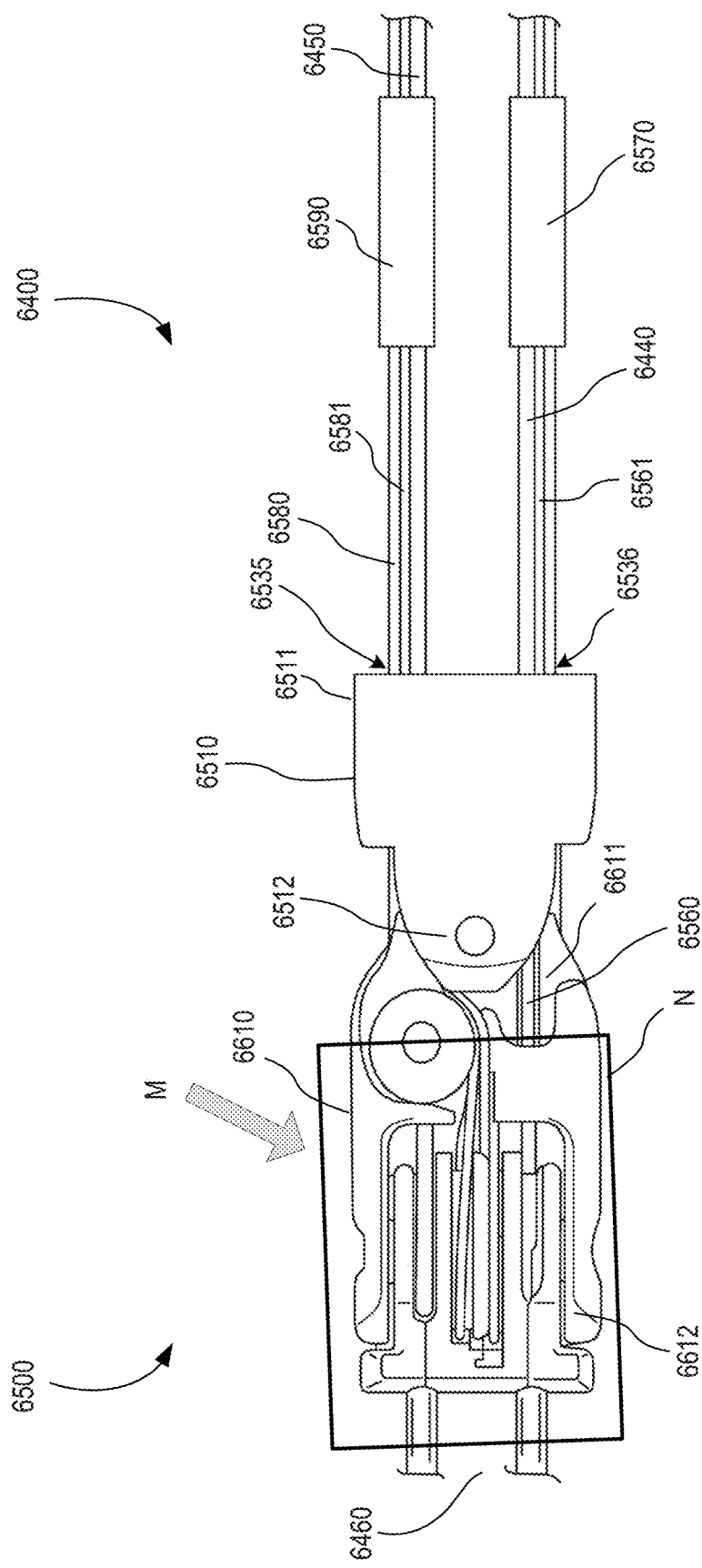
FIG. 21 is a side view of a portion of the distal end portion of the instrument of FIG. 17 in the first orientation.
Figure 22:
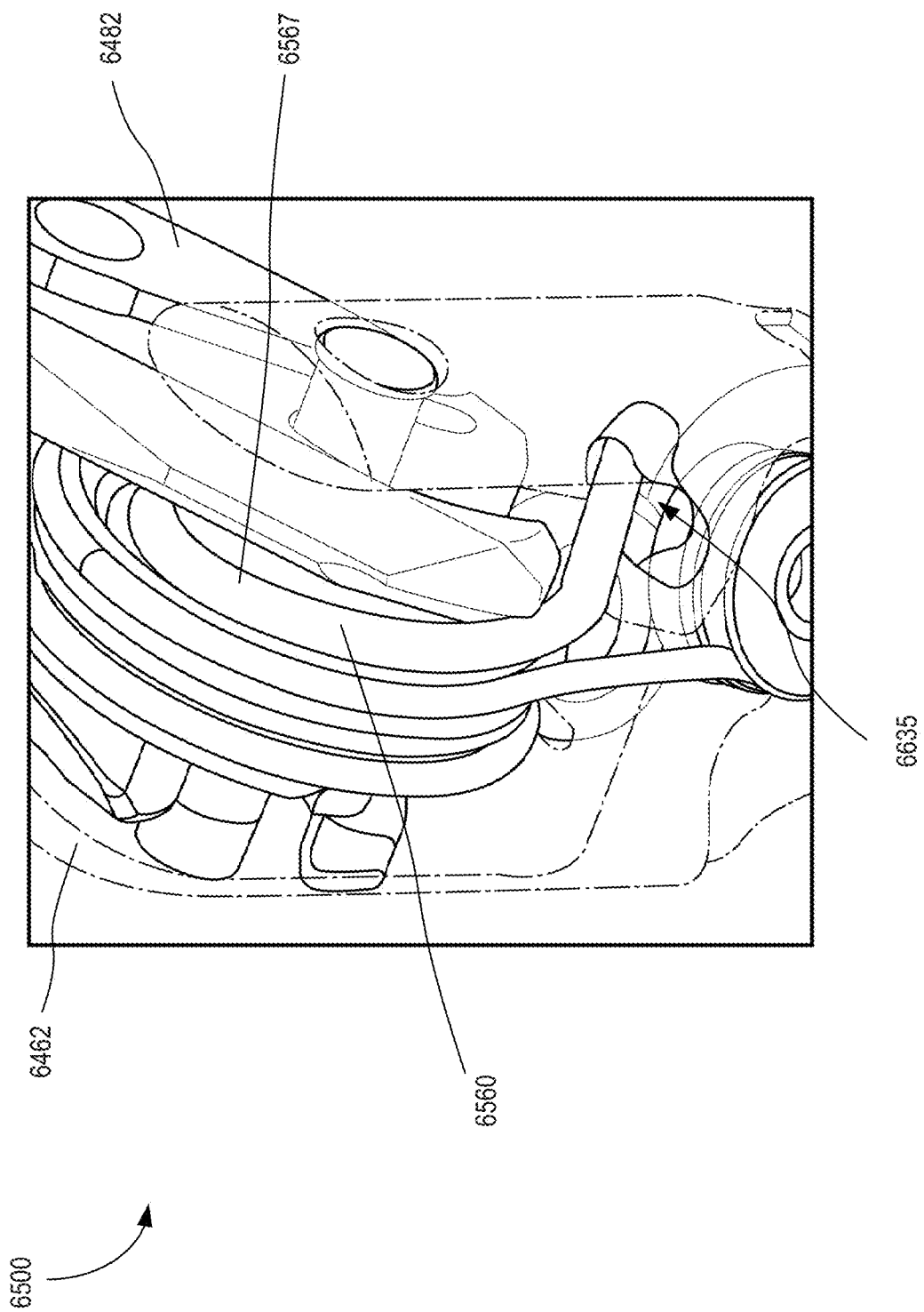
FIG. 22 is a perspective view of a portion of the distal end portion of the instrument of FIG. 21 indicated by the region N shown in FIG. 21, shown in a third orientation.

Switching the route of the non-drive wire from one lateral side to the other allows the distal end portions of each non-drive wire 6560, 6580 to be routed parallel with and close to a tension member 6440, 6450 that moves to rotate the end effector 6460 with respect to the first and second links. Thus, as shown in FIG. 21, a connector 6570 and 6590 connects each of the non-drive wires 6560, 6580 to a tension member 6440, 6450 that moves in the distal direction to rotate the end effector 6460 for rotary movements in which additional flexibility would be provided to the transition portion along with urging the non-drive wire to move a feed portion into the cavity along with the distal movement of the adjacent tension member. Thus, the switch routing that is provided by the guide pathways 6635, 6636 through the second link allow tension member assisted flexibility to be provided to the non-drive wire in a manner similar to what is provided for instrument 3400.

Figure 23:
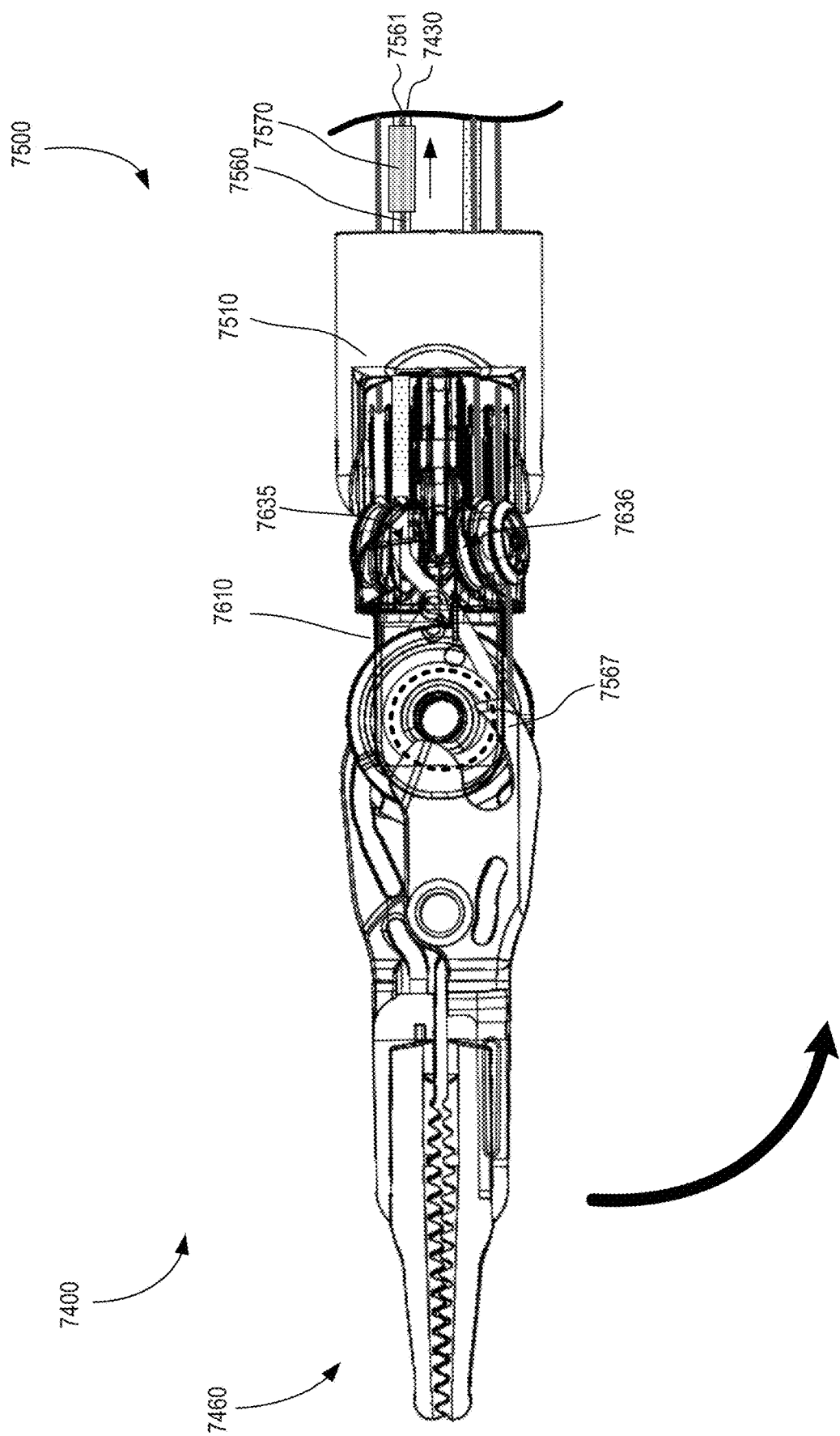
FIG. 23 is an enlarged side view of a distal end portion of an instrument in a first orientation, according to an embodiment.
Figure 24:
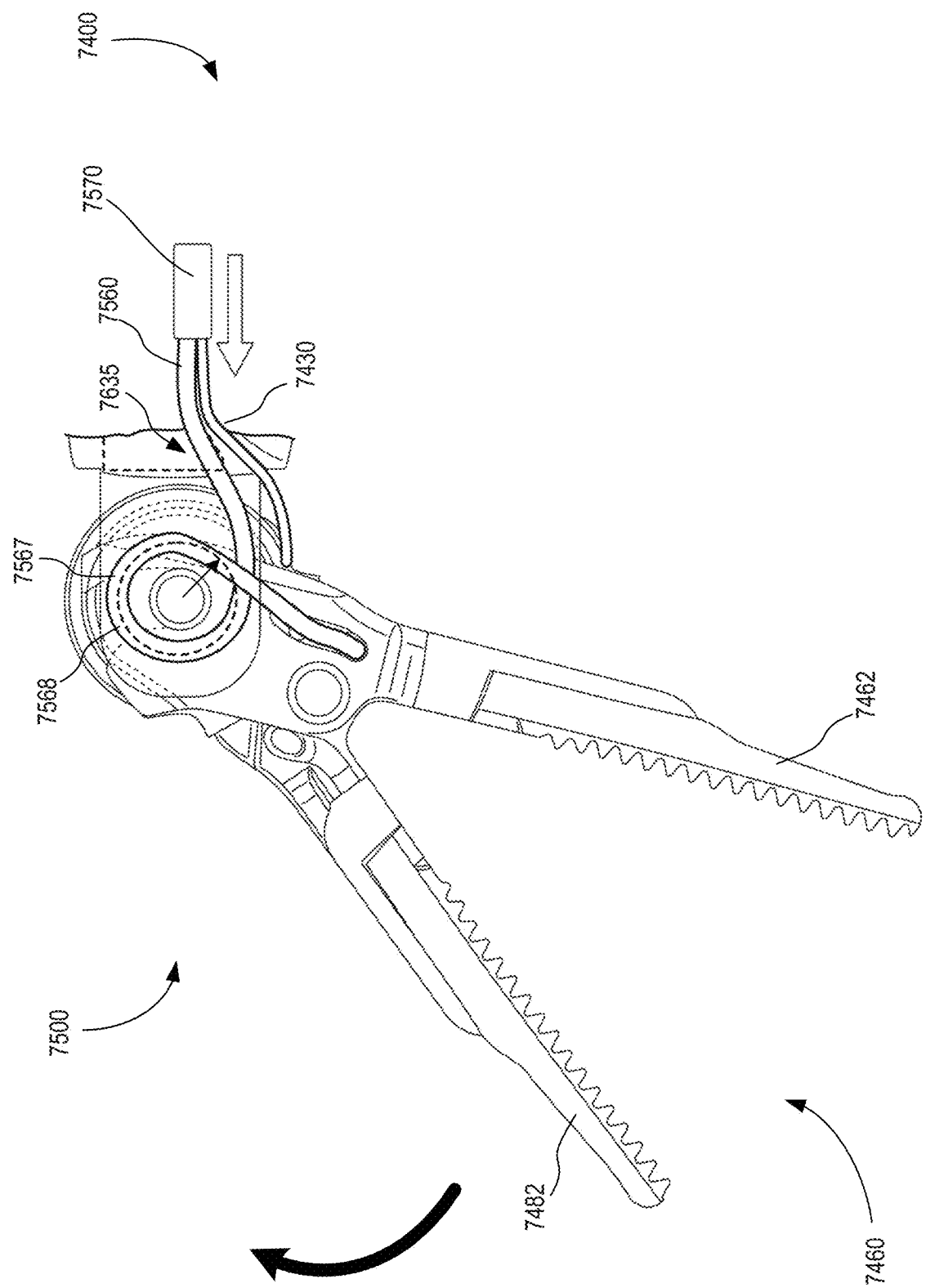
FIG. 24 is an enlarged side view of a distal end portion of the instrument of FIG. 23, shown in a second orientation.
Figure 25:
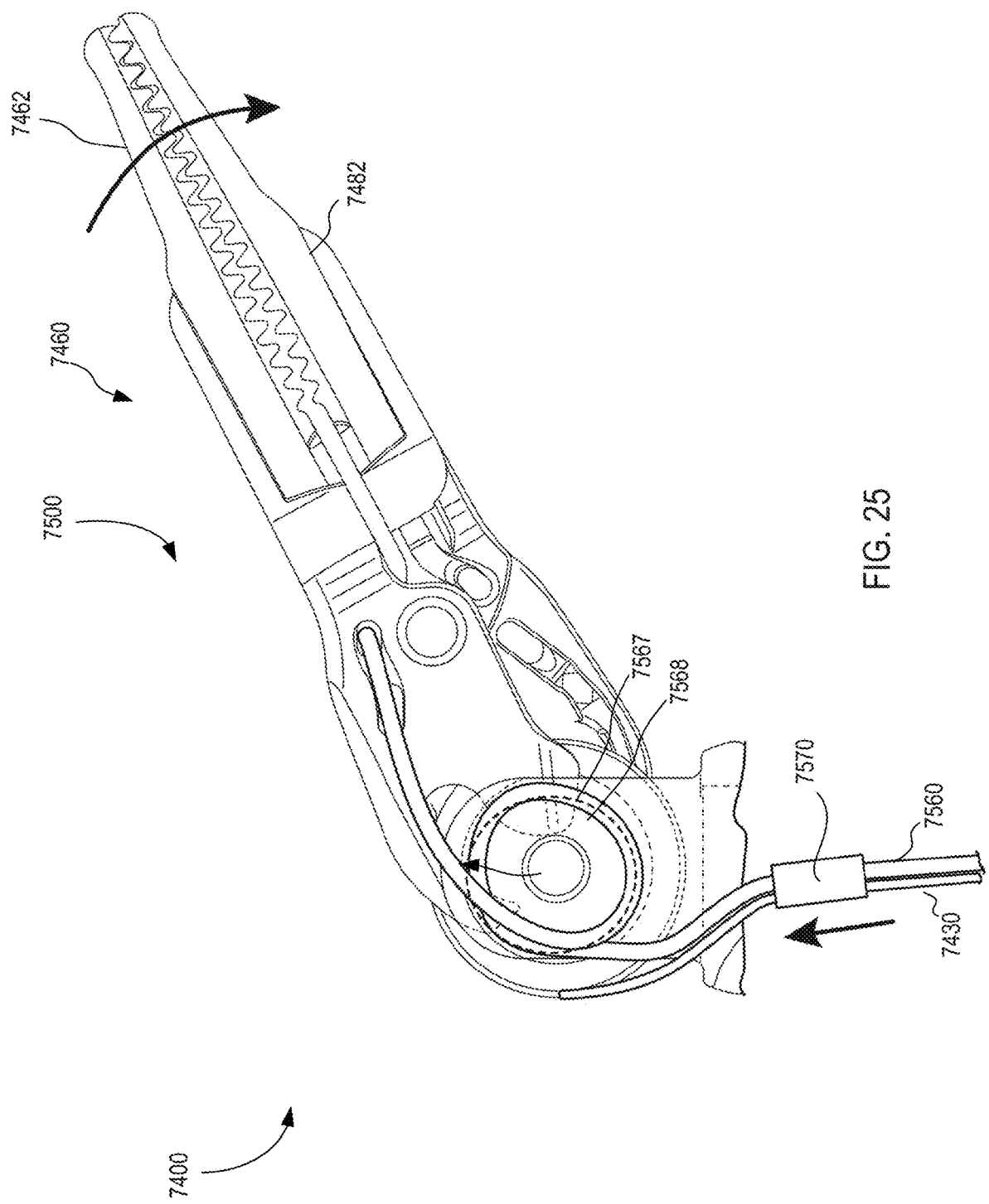
FIG. 25 is an enlarged side view of a distal end portion of the instrument of FIG. 23, shown in a third orientation.

Referring to FIGS. 23-25, the switching guide paths 7635 and 7636 are included in an instrument 7400 that is similar to the instrument 5400. As with instrument 5400, instrument 7400 also includes a wrist assembly 7500 having a proximal first link 7510 and a distal second link 7610. The instrument 7400 includes an end effector 7460 having a pair of tool members 7462, 7482. Switching the route of the non-drive wire 7560 from one lateral side to the other allows the distal end portions of the non-drive wire 7560 to be routed parallel with and close to a tension member 7430 that moves to rotate the end effector 7460 with respect to the first and second links. A connector 7570 connects the non-drive wire 7560 to a tension member 7430. The non-drive wire 7560 has proximal end portion 7561 and a transition portion 7567 (that can form a loop 7568). As such, tension member assisted flexibility functionality can be combined with the transfer member functions described along with instrument 5400. The rotations and orientations shown in FIGS. 23-25 demonstrate the tension member assisted functionality.

While various embodiments have been described above, it should be understood that they have been presented by way of example only, and not limitation. Where methods and/or schematics described above indicate certain events and/or flow patterns occurring in certain order, the ordering of certain events and/or operations may be modified. While the embodiments have been particularly shown and described, it will be understood that various changes in form and details may be made.

For example, any of the instruments described herein (and the components therein) are optionally parts of a surgical assembly that performs minimally invasive surgical procedures, and which can include a patient-side cart, a series of kinematic linkages, a series of cannulas, or the like. Thus, any of the instruments described herein can be used in any suitable surgical system, such as the MIRS system 1000 shown and described above. Moreover, any of the instruments shown and described herein can be used to manipulate target tissue during a surgical procedure. Such target tissue can be cancer cells, tumor cells, lesions, vascular occlusions, thrombosis, calculi, uterine fibroids, bone metastases, adenomyosis, or any other bodily tissue. The presented examples of target tissue are not an exhaustive list. Moreover, a target structure can also include an artificial substance (or non-tissue) within or associated with a body, such as for example, a stent, a portion of an artificial tube, a fastener within the body or the like.

For example, any of the tool members can be constructed from any material, such as medical grade stainless steel, nickel alloys, titanium alloys, or the like. Further, any of the links, tool members, tension members, or components described herein can be constructed from multiple pieces that are later joined together. For example, in some embodiments, a link can be constructed by joining together separately constructed components. In other embodiments, however, any of the links, tool members, tension members, or components described herein can be monolithically constructed.

Although various embodiments have been described as having particular features and/or combinations of components, other embodiments are possible having a combination of any features and/or components from any of embodiments as discussed above. Aspects have been described in the general context of medical devices, and more specifically surgical instruments, but inventive aspects are not necessarily limited to use in medical devices.

What is claimed is:

1. An apparatus, comprising:
   a tension member, a link comprising a distal portion, a transfer member, a tool member, and a non-drive wire;
   the transfer member being coupled to the distal portion of the link and coupled to the tension member such that the transfer member rotates relative to the link when the tension member is moved, the transfer member including a rotatable pulley;

the tool member comprising a base portion movably coupled to the transfer member, the tool member comprising a contact portion configured to engage a target tissue, and movement of the tension member urges the tool member to move relative to the link between a first orientation and a second orientation; and the non-drive wire comprising a first end portion, a second end portion, and a central portion between the first end portion and the second end portion, the first end portion being coupled to an energy source, the second end portion being coupled to the contact portion of the tool member, the central portion comprising a transition portion within a cavity defined within a portion of the rotatable pulley of the transfer member, the rotatable pulley including a guide portion defined by an outer wall, the outer wall having a first wall portion with a first height and a second wall portion with a second height, the first height being shorter than the second height, the first wall portion defining a wire entry sector at which the non-drive wire enters the cavity, and the transition portion having a compact first configuration when the tool member is in the first orientation and an expanded second configuration when the tool member is in the second orientation.

2. The apparatus of claim 1, wherein:
a force biases the transition portion toward the compact first configuration; and
the transition portion expands against the force when the tool member rotates from the first orientation to the second orientation.

3. The apparatus of claim 1, wherein the contact portion of the tool member is electrically conductive and is configured to contact the target tissue.

4. The apparatus of claim 1, wherein:
the transition portion comprises a pre-set non-linear arrangement of the non-drive wire when the transition portion is in the compact first configuration; and
the transition portion is configured to return to the pre-set non-linear arrangement in the absence of tension in a longitudinal direction of the non-drive wire.

5. The apparatus of claim 4, wherein the pre-set non-linear arrangement comprises a bight formed in the non-drive wire.

6. The apparatus of claim 5, wherein the bight includes a coil, a loop, a fold, or a bend formed in the non-drive wire.

7. The apparatus of claim 1, wherein:
the transfer member is rotatably coupled to the distal portion of the link about a rotation axis; and
the cavity is formed within the transfer member around a portion of the rotation axis.

8. The apparatus of claim 1, wherein:
the rotatable pulley comprises an outer surface about which the tension member is at least partially wrapped such that movement of the tension member urges the rotatable pulley to rotate relative to the link; and
the cavity is defined by an outer surface of the rotatable pulley.

9. The apparatus of claim 1, wherein:
the apparatus further comprises a first pin defining a first axis of rotation and a second pin defining a second axis of rotation;

the rotatable pulley is coupled to the link by the first pin, the rotatable pulley being configured to rotate relative to the link about the first pin;

the tool member is rotatably coupled to the rotatable pulley by the second pin, the tool member being configured to rotate relative to the rotatable pulley about the second pin; and the transition portion of the non-drive wire at least partially surrounds the first pin.

10. The apparatus of claim 1, wherein:
the central portion of the non-drive wire comprises a release portion between the transition portion and the second end portion of the non-drive wire;
the release portion is in the cavity when the tool member is in the first orientation and the transition portion is in the compact first configuration; and
the release portion is out of the cavity when the tool member is in the second orientation and the transition portion is in the expanded second configuration.

11. The apparatus of claim 10, wherein:
the central portion of the non-drive wire comprises a feed portion between the transition portion and the first end portion of the non-drive wire;
the feed portion is out of the cavity when the tool member is in the first orientation; and
the feed portion is in the cavity when the tool member is in the second orientation.

12. An apparatus, comprising:
a link, a first tool member, a first transfer member, a non-drive wire, and a first tension member;
the first transfer member being rotatably coupled to the link;
the first tool member comprising a first contact portion and a first base portion movably coupled to the first transfer member about a first rotation axis,
the first contact portion being electrically conductive and configured to contact a target tissue,
the first base portion being rotatably coupled to the link about a second rotation axis via the first transfer member, the first tool member being rotatable relative to the link between a first orientation and a second orientation, and
a cavity being defined within the first transfer member;
the non-drive wire comprising a first end portion, a second end portion, and a central portion between the first end portion and the second end portion,
the first end portion being coupled to an energy source,
the second end portion being coupled to the first contact portion of the first tool member,
the central portion comprising a transition portion and a feed portion, the transition portion being within the cavity of the first transfer member, the first transfer member including a guide portion defined by an outer wall, the outer wall having a first wall portion with a first height and a second wall portion with a second height, the first height being shorter than the second height, the first wall portion defining a wire entry sector at which the non-drive wire enters the cavity, and
the transition portion expanding from a relaxed first state to an extended second state when the first tool member rotates from the first orientation to the second orientation; and
the first tension member being coupled to rotate at least one of the first tool member or a second tool member when the first tension member is moved, the non-drive wire being coupled to the first contact portion of the first tool member such that movement of the first tool member rotates the first tool member and causes the feed portion to move from a first position outside of the cavity to a second position inside the cavity.

13. The apparatus of claim 12, wherein:

the apparatus further comprises the second tool member, a second transfer member, and a second tension member;

the second transfer member being rotatably coupled to the link;

the second tool member being coupled to the link, the second tool member comprising a second contact portion and a second base portion movably coupled to the second transfer member about a third rotation axis, the second contact portion being electrically conductive and configured to contact the target tissue, the second base portion being rotatably coupled to the link via the second transfer member, and the second tool member being rotatable relative to the link about the second rotation axis;

the first tension member is coupled to the second base portion, the second tool member being configured to rotate relative to the link when the first tension member is moved; and the second tension member is coupled to the first base portion, the first tool member being configured to rotate relative to the link when the second tension member is moved.

14. The apparatus of claim 12, wherein:

the central portion of the non-drive wire comprises a release portion between the transition portion and the second end portion;

the release portion is in the cavity when the first tool member is in the first orientation and the transition portion is in the relaxed first state; and the release portion is out of the cavity when the first tool member is in the second orientation and the transition portion is expanded to the extended second state.

15. The apparatus claim 12, wherein:

the cavity is defined within the first transfer member around a portion of the second rotation axis.

16. An apparatus, comprising:

a shaft, a tension member, a first tool member, a second tool member, a non-drive wire, a transfer member, and a link coupled to the shaft;

the transfer member coupled to the tension member and including a rotatable pulley;

the first tool member comprising a first contact portion and a first base portion, the first base portion movably coupled to the transfer member about a first rotation axis, and the first contact portion being electrically conductive and configured to contact a target tissue;

the second tool member comprising a second contact portion and a second base portion, the second contact portion being electrically conductive and configured to contact the target tissue;

the non-drive wire comprising a first end portion, a second end portion, and a central portion between the first end portion and the second end portion, the central portion comprising a transition portion disposed within a cavity defined within a portion of the rotatable pulley of the transfer member, the rotatable pulley including a guide portion defined by an outer wall, the outer wall having a first wall portion with a first height and a second wall portion with a second height, the first height being shorter than the second height, the first wall portion defining a wire entry sector at which the non-drive wire enters the cavity; and the link comprising a first guide path;

wherein the first base portion is rotatably coupled to the link via the transfer member such that the first tool member is rotatable relative to the link about a second rotation axis between a first orientation and a second orientation;

wherein the second base portion is rotatably coupled to the link such that the second tool member is rotatable relative to the link about the second rotation axis;

wherein the second end portion of the non-drive wire is coupled to the first contact portion;

wherein the central portion of the non-drive wire is configured to transition between a compact first configuration and an expanded second configuration, the central portion being in the compact first configuration when the first tool member is in the first orientation, the central portion being in the expanded second configuration when the first tool member is in the second orientation;

wherein the tension member is coupled to the first base portion;

wherein movement of the tension member urges the first tool member to rotate relative to the link about the second rotation axis; and wherein the non-drive wire is coupled to the first contact portion such that movement of the first tool member causes a feed portion of the non-drive wire to be conveyed between the shaft and the first guide path.

17. The apparatus of claim 16, wherein:

a cavity is defined within the transfer member around a portion of the second rotation axis; and a portion of the central portion of the non-drive wire is disposed within the cavity around the portion of the second rotation axis.

* * * * *